United States Patent
Yabu et al.

(10) Patent No.: US 10,442,886 B2
(45) Date of Patent: Oct. 15, 2019

(54) MECHANOCHROMIC LUMINESCENT MATERIAL, MECHANOCHROMIC RESIN OBTAINED BY CROSSLINKING MECHANOCHROMIC LUMINESCENT MATERIAL, METHOD FOR PRODUCING MECHANOCHROMIC LUMINESCENT MATERIAL, AND METHOD FOR PRODUCING MECHANOCHROMIC

(71) Applicant: JAPAN SCIENCE AND TECHNOLOGY AGENCY, Kawaguchi-shi, Saitama (JP)

(72) Inventors: Hiroshi Yabu, Sendai (JP); Yuta Saito, Sendai (JP); Shohei Saito, Nagoya (JP); Shigehiro Yamaguchi, Nagoya (JP); Shunpei Nobusue, Nagoya (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 184 days.

(21) Appl. No.: 15/527,639

(22) PCT Filed: Nov. 16, 2015

(86) PCT No.: PCT/JP2015/082143
§ 371 (c)(1),
(2) Date: May 17, 2017

(87) PCT Pub. No.: WO2016/080358
PCT Pub. Date: May 26, 2016

(65) Prior Publication Data
US 2019/0031820 A1 Jan. 31, 2019

(30) Foreign Application Priority Data
Nov. 18, 2014 (JP) .................................. 2014-233309

(51) Int. Cl.
*C08G 61/00* (2006.01)
*C08G 61/08* (2006.01)
(Continued)

(52) U.S. Cl.
CPC ........... *C08G 61/08* (2013.01); *C07D 209/70* (2013.01); *C09K 9/02* (2013.01); *C09K 11/06* (2013.01);
(Continued)

(58) Field of Classification Search
CPC .... C07C 13/263; C07D 209/56; C07D 209/94
See application file for complete search history.

(56) References Cited

FOREIGN PATENT DOCUMENTS

JP 2014-58606 A 4/2014

OTHER PUBLICATIONS

Yuan, C.; Saito, S.; Camacho, C.; Kowalczyk, T.; Irle, S.; Yamaguchi, S. Chem. Eur. J. 2014, 20, 2193-2200. (Year: 2014).*

(Continued)

*Primary Examiner* — Rip A Lee
(74) *Attorney, Agent, or Firm* — Amster, Rothstein & Ebenstein LLP

(57) ABSTRACT

Provided is a mechanochromic resin by which a stress applied to a material can be visualized in real time, and a mechanochromic luminescent material that is used in the synthesis of the mechanochromic resin. Stress can be visualized in real time by means of a mechanochromic luminescent material represented by formula (1) or formula (2) and a mechanochromic resin obtained by crosslinking the mechanochromic luminescent material. [Chemical formula 1] (In the formula, $Y_1$ and $Y_2$ each denote a substituent group that inhibits aggregation of the mechanochromic luminescent material represented by formula (1), and $Y_1$ and $Y_2$ may be same as or different from each other. $Z_1$ and $Z_2$ each (Continued)

denote a polymerizable group, and may be same as or different from each other.) [Chemical formula 2] (In the formula, $Y_1$ and $Y_2$ each denote a substituent group that inhibits aggregation of the mechanochromic luminescent material represented by formula (2), and $Y_1$ and $Y_2$ may be same as or different from each other. $Z_1$ and $Z_2$ each denote a polymerizable group, and may be same as or different from each other).

[Chemical formula 1]

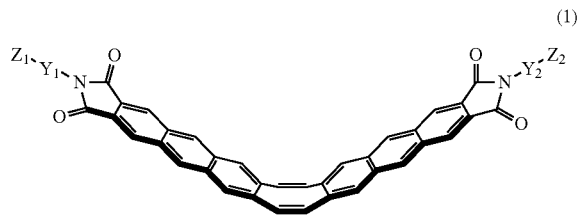

(1)

[Chemical formula 2]

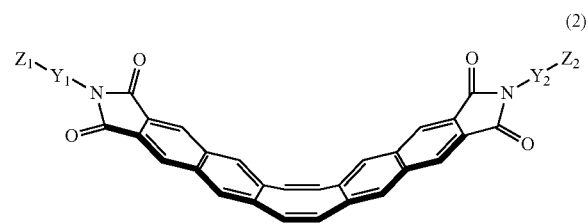

(2)

8 Claims, 6 Drawing Sheets

(51) Int. Cl.
    *C07D 209/70*     (2006.01)
    *G01L 1/24*     (2006.01)
    *C09K 9/02*     (2006.01)
    *C09K 11/06*     (2006.01)
(52) U.S. Cl.
    CPC .......... *G01L 1/24* (2013.01); *C08G 2261/122* (2013.01); *C08G 2261/135* (2013.01); *C08G 2261/3324* (2013.01); *C08G 2261/418* (2013.01); *C08G 2261/522* (2013.01); *C08G 2261/62* (2013.01); *C08G 2261/76* (2013.01)

(56) References Cited

OTHER PUBLICATIONS

Brent R. Crenshaw and Christoph Weder, "Deformation-Induced Color Changes in Melt-Processed Photoluminescent Polymer Blends," Chemistry of Materials, vol. 15, pp. 4717-4724 (2003).
Douglas A. Davis et al., "Force-induced activation of covalent bonds in mechanoresponsive polymeric materials," Nature, vol. 459, pp. 68-72 (May 2009).
Yulan Chen et al., "Mechanically induced chemiluminescence from polymers incorporating a 1,2-dioxetane unit in the main chain," Nature Chemistry, vol. 4, pp. 559-562 (Jul. 2012).
Gregory R. Gossweiler et al., "Mechanochemical Activation of Covalent Bonds in Polymers with Full and Repeatable Macroscopic Shape Recovery," ACS Macro Letters, vol. 3, pp. 216-219 (2014).
Chunxue Yuan et al., "A π-Conjugated System with Flexibility and Rigidity That Shows Environment-Dependent RGB Luminescence," Journal of the American Chemical Society, vol. 135, pp. 8842-8845 (2013).
Chunxue Yuan et al., "Hybridization of a Flexible Cyclooctatetraene Core and Rigid Aceneimide Wings for Multiluminescent Flapping π Systems," Chemistry—A European Journal, vol. 20, pp. 2193-2200 (2014).
Shohei Saito and Shigehiro Yamaguchi, "Move the π-conjugated skeleton to develop function," Chemistry, vol. 69, No. 5, pp. 32-37 (May 2014).
International Searching Authority, "Written Opinion", received for PCT Patent Application No. PCT/JP2015/082143 dated Feb. 16, 2016, 4 pages.
European Patent Office, "Extended European Search Report," issued in European Patent Application No. 15 860 298.7, which is a European counterpart of U.S. Appl. No. 15/527,639, dated Oct. 20, 2017, 9 pages.
The State Intellectual Property Office of People's Republic of China, "The First Office Action," issued in Chinese Patent Application No. 201580061377.0, which is a Chinese counterpart of U.S. Appl. No. 15/527,639, dated Nov. 13, 2018, 11 pages (7 pages of English Translation of Office Action and 4 pages of Original Office Action).

\* cited by examiner

MECHANOCHROMIC LUMINESCENT MATERIAL, MECHANOCHROMIC RESIN OBTAINED BY CROSSLINKING MECHANOCHROMIC LUMINESCENT MATERIAL, METHOD FOR PRODUCING MECHANOCHROMIC LUMINESCENT MATERIAL, AND METHOD FOR PRODUCING MECHANOCHROMIC

CROSS REFERENCE TO RELATED APPLICATIONS

This application is a § 371 US national stage of International Application No. PCT/JP2015/082143 filed on Nov. 16, 2015 and claims the benefit of and priority to Japanese Patent Application No. 2014-233309 filed on Nov. 18, 2014, the contents of which are hereby incorporated by reference in their entirety.

FIELD OF THE INVENTION

The present invention relates to a mechanochromic luminescent material and a mechanochromic resin obtained by crosslinking the mechanochromic luminescent material, a method for producing a mechanochromic luminescent material, and a method for producing a mechanochromic resin, in particular to a mechanochromic resin that rapidly changes its luminescent color due to stretching/contraction and a method for producing the same, and to a mechanochromic luminescent material for synthesizing a mechanochromic resin and a method for producing the same.

DESCRIPTION OF THE RELATED ART

Various uses for functional materials are being developed in accordance with their characteristics. One example is an attempt to visualize mechanical stresses such as compression, stretching, and bending experienced by a material.

Visualization by excimer dispersion (see Non-patent Document 1), visualization by the cleaving of bonds of dye molecules (see Non-patent Document 2), visualization by energy transfer via chemiluminescence (see Non-patent Document 3), visualization by small molecule release (see Non-patent Document 4), and the like are known as methods of visualizing mechanical stresses.

Mechanochromic materials comprising polymers having a urethane structure or ester structure in which a diarylbibenzofuranone structure is urethane bonded or ester bonded as a repeating unit are also known (see Patent Document 1).

Synthetic π-conjugated molecules have been used for a long time as dyes and pigments, aromatic polymers, and compositions of optical recording materials, and have been popularized in recent years in the form of organic EL photodynamic therapy agents, fluorescent probes, and the like. Since synthetic π-conjugated molecules are typically constructed from rigid aromatic rings and multiple bonds (primarily $sp^2$ carbons), the vast majority inherently have a rigid structure.

A rigid structure has many advantages in terms of physical properties, such as permitting the synthesis of a targeted molecular skeleton, and slow nonradioactive decay and high luminous efficiency since the structural changes are slight. On the other hand, the fact that the basic molecular skeleton is rigid is similar to inorganic materials, and one can also conceive that the transformation of physical properties derived from the flexibility of the structure is difficult and limited to the expression of static physical properties. The present inventors therefore created a compound having luminescent anthraceneimide fused as two rigid "wings" on opposite sides of a flexible conjugated eight-membered ring (cyclooctatetraene), as shown in FIG. 1(1). This compound exhibits inversion behavior between a V shape and a Λ shape in conjunction with movement of the eight-membered ring, as shown in FIG. 1(2), and emits blue when in the V shape and green when planar due to changes in the electronic structure associated with movement of the three-dimensional structure (see Non-patent Documents 5 and 6).

By using this compound, the degree of mechanical stimulation and damage location can be visualized by visually indicating the extent of mechanical stimulation (mechanical stress) undergone by a material by a change in luminescent color. As a visualization technique using this compound, for example, the present inventors discovered that the course of curing of an adhesive can be visualized by dispersing this compound in an adhesive, and also that sites of insufficient curing can be distinguished in a contactless manner (see Non-patent Document 7).

PRIOR ART DOCUMENTS

Patent Documents

Patent Document 1: Japanese Unexamined Patent Application Publication 2014-58606

Non-Patent Documents

Non-patent Document 1: Christoph Weder et al., "Deformation-Induced Color Changes in Melt-Processed Photoluminescent Polymer Blends", Chem Mater, 2003, 15, p 4717-4724

Non-patent Document 2: N. R. Sottos et al., "Force-induced activation of covalent bonds in mechanoresponsive polymeric materials", Nature, 2009, Vol. 459, p 68-72

Non-patent Document 3: R. P. Sijbesma et al., "Mechanically induced chemiluminescence from polymers incorporating a 1,2-dioxetane unit in the main chain", Nature Chem, 2012, Vol. 4, p 559-562

Non-patent Document 4: Stephen L. Craig et al., "Mechanochemical Activation of Covalent Bonds in Polymers with Full and Repeatable Macroscopic Shape Recovery", ACS Macro Lett, 2014, 3, p 216-219

Non-patent Document 5: S. Saito et al., "A π-Conjugated System with Flexibility and Rigidity That Shows Environment-Dependent RGB Luminescence", Journal of the American Chemical Society, 2013, 135, p 8842-8845

Non-patent Document 6: S. Saito et al., "Hybridization of a Flexible Cyclooctatetraene Core and Rigid Aceneimide Wings for Multiluminescent Flapping π Systems", Chemistry—A European Journal, 2014, 20, p 2193-2200 Non-patent Document 7: S. Saito, S. Yamaguchi, "Expression of function through movement of a π-conjugated skeleton," Kagaku, Vol. 69, No. 5 (2014), p. 32-37

SUMMARY OF THE INVENTION

Problems Solved by the Invention

However, the problem with the visualization methods described in Non-patent Documents 1-3 is that all are irreversible and cannot be used repeatedly. Of the two visualization methods described in Non-patent Document 4, the problem with one is that a reversible color change occurs only when mechanical stress is applied after the second time, and the functional material produced cannot be used without further modification. The problem with the other is that heat must be applied when releasing small molecules and that there is only a difference of several percentage points in the brightness of the fluorescence before and after pulling. The problem, therefore, is that the visualization methods described in Non-patent Documents 1-4 do not make it possible to visualize mechanical stress quickly and reversibly.

Meanwhile, the method described in Patent Document 1 makes it possible to visualize mechanical stress reversibly. However, the mechanochromic luminescent material described in Patent Document 1 provides visualization by radical species generated by cleavage of the carbon-carbon bonds of the diarylbibenzofuranone structure due to mechanical stimulation. Consequently, it takes approximately two hours after release of the mechanical stimulation for the radical species to rebond and return to the original color, and the stress applied to a material cannot be confirmed in real time.

The compound described in Non-patent Document 7 permits visualization of the course of curing of an adhesive, but the problem is that changes in the degree of stress undergone by a material cannot be visualized in real time.

The present invention is intended to solve the above problems. It was newly discovered as a result of in-depth studies that (i) a mechanochromic resin obtained by cross-linking a mechanochromic luminescent material represented by formula (1) or formula (2) below to a polymer chain makes it possible to visualize the stress undergone by a material in real time since the luminescent color changes rapidly and reversibly due to stretching/contraction, and (ii) synthesis of a mechanochromic resin is difficult even when a polymerizable group is merely introduced into an anthraceneimide dimer or naphthaleneimide dimer described in Non-patent Documents 5-7, but a mechanochromic resin obtained by crosslinking a mechanochromic luminescent material can be synthesized by introducing a substituent that inhibits aggregation between the anthraceneimide dimer or naphthaleneimide dimer and the polymerizable group.

[Chemical formula 1]

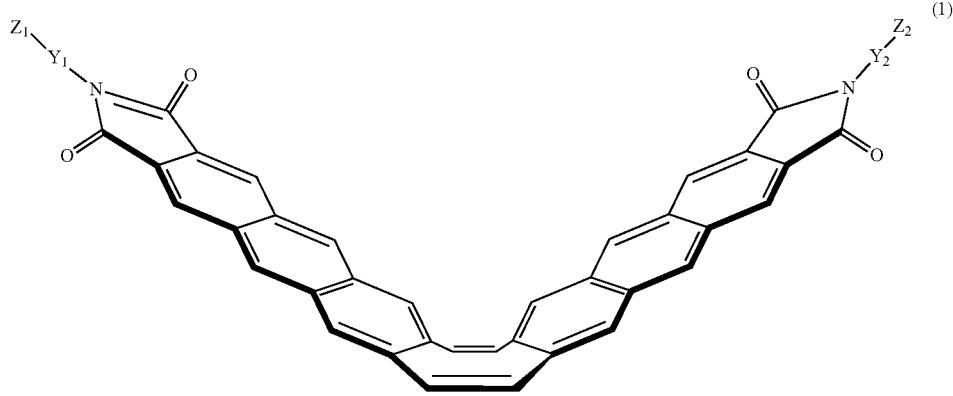

(In the formula, $Y_1$ and $Y_2$ represent substituents that inhibit aggregation of a mechanochromic luminescent material represented by formula (1), and may be the same or different. $Z_1$ and $Z_2$ represent polymerizable groups, and may be the same or different.)

[Chemical formula 2]

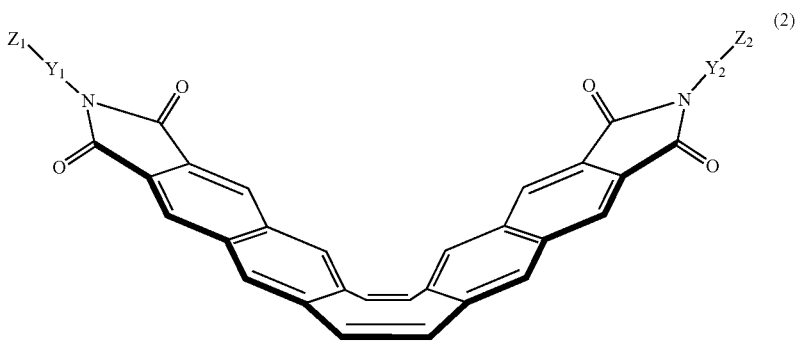

(In the formula, $Y_1$ and $Y_2$ represent substituents that inhibit aggregation of a mechanochromic luminescent material represented by formula (2), and may be the same or different. $Z_1$ and $Z_2$ represent polymerizable groups, and may be the same or different.)

Specifically, it is an object of the present invention to provide a mechanochromic luminescent material, a mechanochromic resin obtained by crosslinking the mechanochromic luminescent material, a method for producing a mechanochromic luminescent material, and a method for producing a mechanochromic resin.

Means for Solving the Above-Mentioned Problems

The present invention, as indicated hereunder, is a mechanochromic luminescent material, a mechanochromic resin obtained by crosslinking the mechanochromic luminescent material, a method for producing a mechanochromic luminescent material, and a method for producing a mechanochromic resin.

(1) A mechanochromic luminescent material represented by formula (1) or formula (2) below.

[Chemical formula 3]

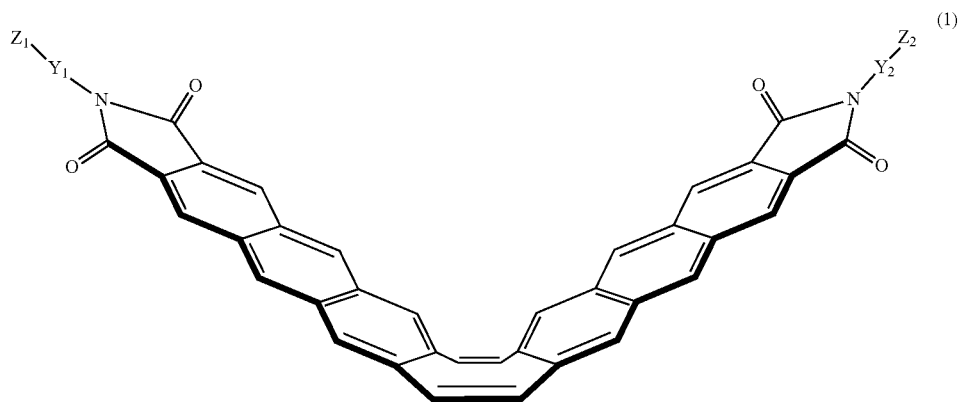

(1)

(In the formula, $Y_1$ and $Y_2$ represent substituents that inhibit aggregation of a mechanochromic luminescent material represented by formula (1), and may be the same or different. $Z_1$ and $Z_2$ represent polymerizable groups, and may be the same or different.)

[Chemical formula 4]

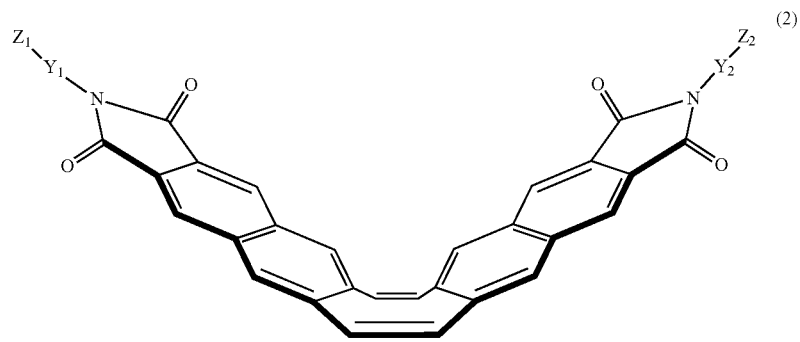

(2)

(In the formula, $Y_1$ and $Y_2$ represent substituents that inhibit aggregation of a mechanochromic luminescent material represented by formula (2), and may be the same or different. $Z_1$ and $Z_2$ represent polymerizable groups, and may be the same or different.)

(2) The mechanochromic luminescent material according to (1) above, wherein $Y_1$ and $Y_2$ are selected from the following substituents.

[Chemical formula 5]

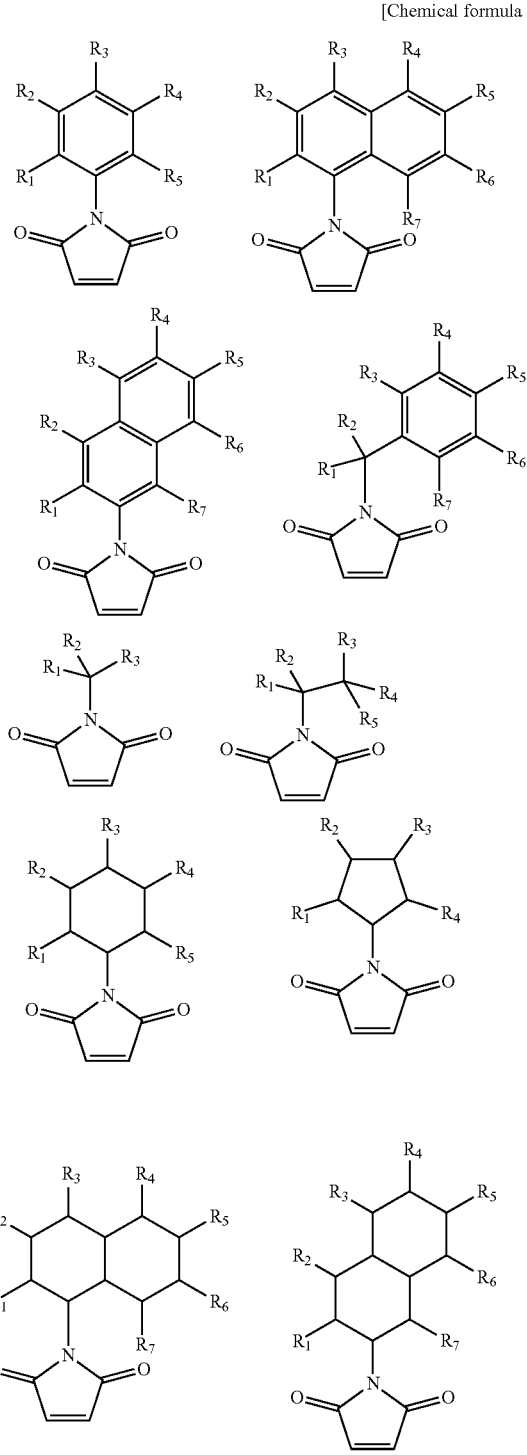

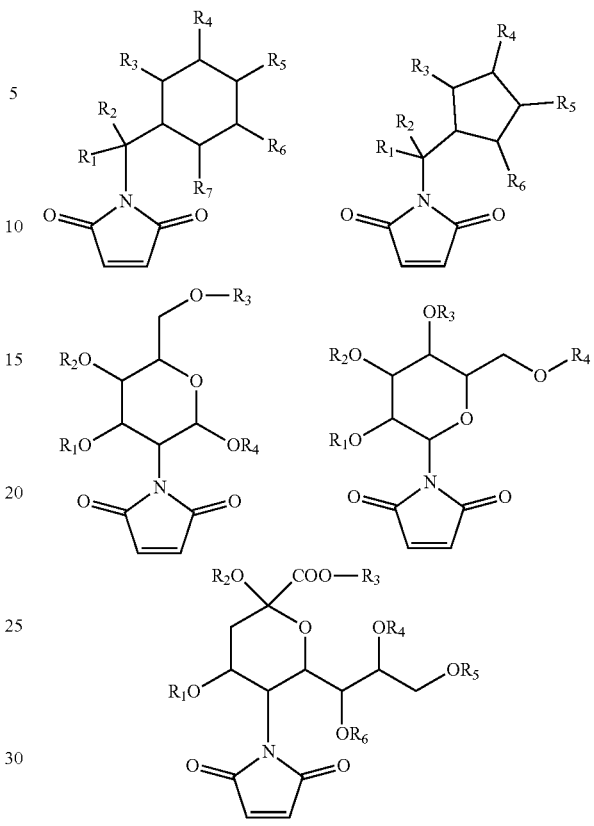

(Any one of the substituents $R_1$-$R_7$ represents a polymerizable group $Z_1$ or $Z_2$; $R_1$-$R_7$ other than the polymerizable group $Z_1$ or $Z_2$ represent H, a C1-20 linear, branched, or cyclic alkyl group, C6-20 aryl group, F, Cl, Br, I, $CF_3$, $CCl_3$, or $OCH_3$; and $R_1$-$R_7$ other than the polymerizable group $Z_1$ or $Z_2$ may be the same or different.)

(3) The mechanochromic luminescent material according to (1) or (2) above, wherein the polymerizable groups $Z_1$ and $Z_2$ are selected from the following substituents.

[Chemical formula 6]

(3)

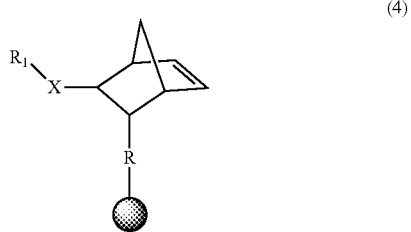

(4)

-continued (5) 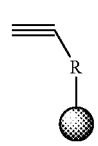

(6) 

(7) 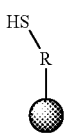

(8) 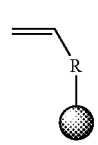

(9) 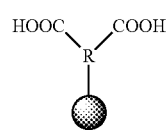

(10) 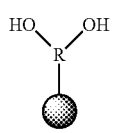

-continued

(11) 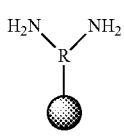

(12) 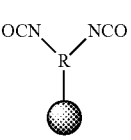

(13) 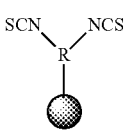

(In the above formulas (3) and (4), X represents an amide or ester, but may be absent; in the above formulas (3) and (4), $R_1$ is the same as $R_1$ in (2) above; in the above formulas (3) to (13), R represents a C1-20 linear, branched, or cyclic alkyl group or a C6-20 aryl group, but R may be absent; and ● represents $Y_1$ or $Y_2$.)

(4) A mechanochromic resin in which the mechanochromic luminescent material according to any of (1) to (3) above is crosslinked to a polymer chain.

(5) The mechanochromic resin according to (4) above, wherein the mechanochromic resin is in the form of a film or a fiber.

(6) A tension sensor including the mechanochromic resin according to (4) or (5) above.

(7) A method for producing a mechanochromic luminescent material represented by formula (26) below, including a step for reacting a compound represented by formula (16) below and a compound represented by formula (25) below.

[Chemical formula 7]

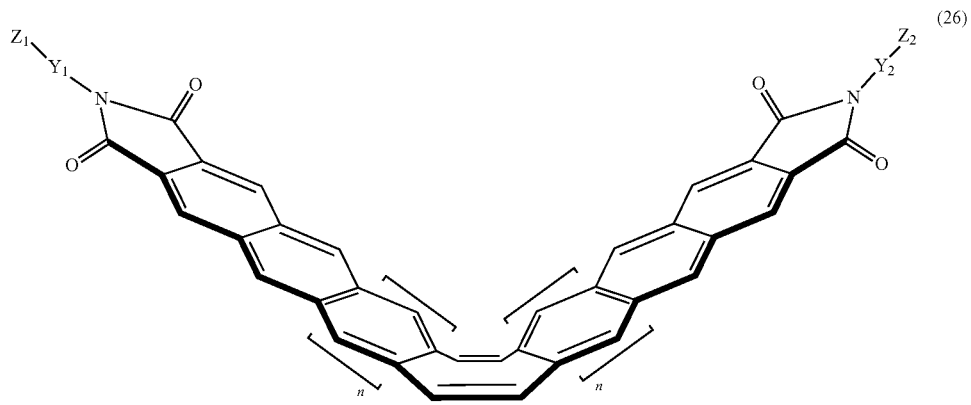

(26)

(In the formula, $Y_1$ and $Y_2$ represent substituents that inhibit aggregation of a mechanochromic luminescent material represented by formula (26), and may be the same or different. $Z_1$ and $Z_2$ represent polymerizable groups, and may be the same or different. n represents an integer of 0-3.)

[Chemical formula 8]

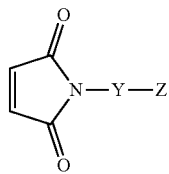

(16)

(In the formula, Y is the same as $Y_1$ or $Y_2$; and Z is the same as $Z_1$ or $Z_2$.)

[Chemical formula 9]

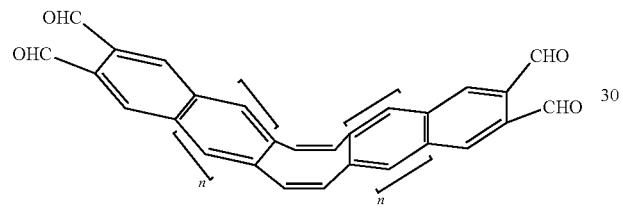

(25)

(In the formula, n represents an integer of 0-3.)

(8) The method for producing a mechanochromic luminescent material according to (7) above, wherein $Y_1$ and $Y_2$ are selected from the following substituents.

[Chemical formula 10]

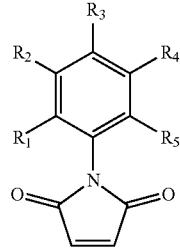
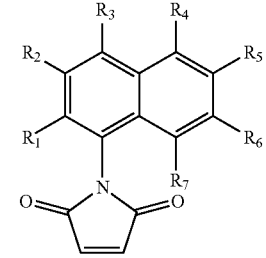

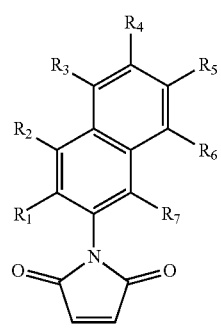
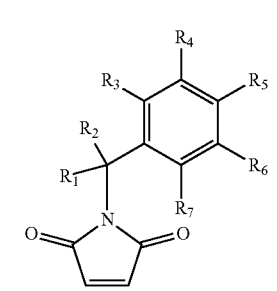

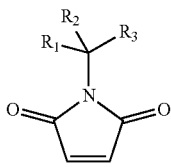
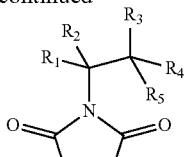

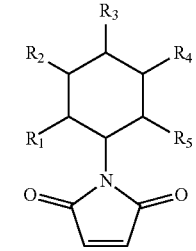
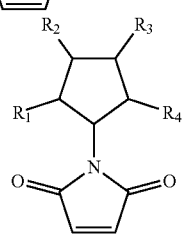

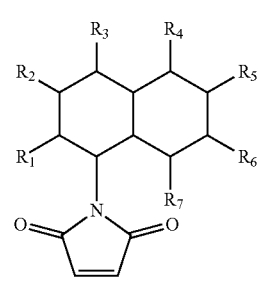
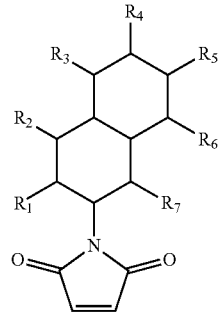

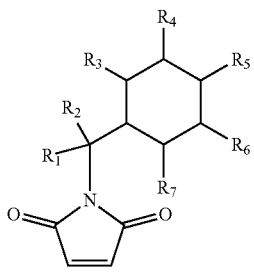
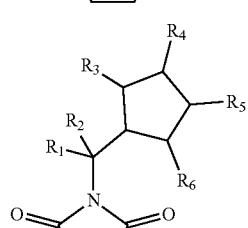

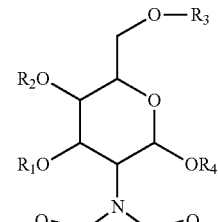
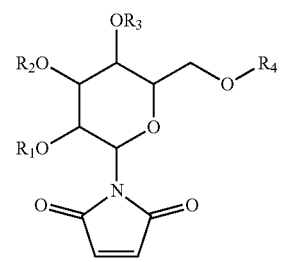

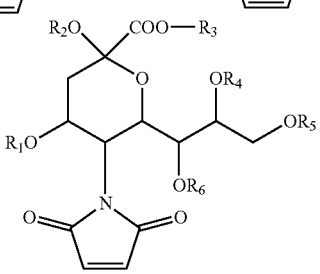

(Any one of the substituents $R_1$-$R_7$ represents a polymerizable group $Z_1$ or $Z_2$; $R_1$-$R_7$ other than the polymerizable group $Z_1$ or $Z_2$ represent H, a C1-20 linear, branched, or cyclic alkyl group, C6-20 aryl group, F, Cl, Br, I, $CF_3$, $CCl_3$, or $OCH_3$; and $R_1$-$R_7$ other than the polymerizable group $Z_1$ or $Z_2$ may be the same or different.)

(9) The method for producing a mechanochromic luminescent material according to (7) or (8) above, wherein the polymerizable groups $Z_1$ and $Z_2$ are selected from the following substituents.

[Chemical formula 11]

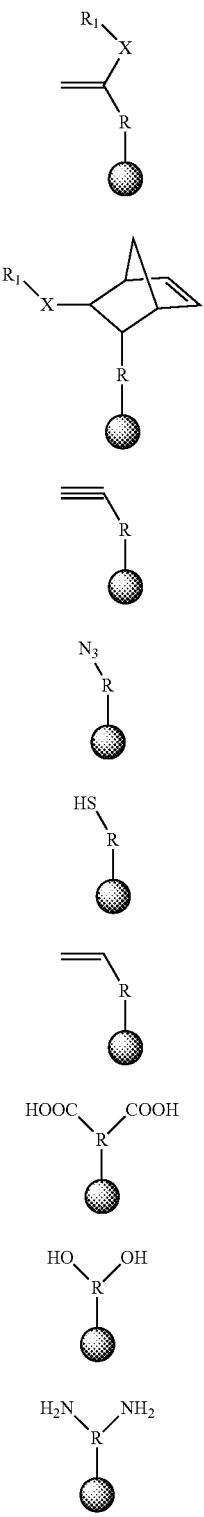

(3)
(4)
(5)
(6)
(7)
(8)
(9)
(10)
(11)

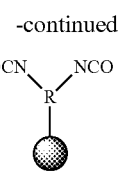
(12)

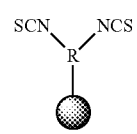
(13)

(In the above formulas (3) and (4), X represents an amide or ester, but may be absent; in the above formulas (3) and (4), $R_1$ is the same as $R_1$ in (8) above; in the above formulas (3) to (13), R represents a C1-20 linear, branched, or cyclic alkyl group or a C6-20 aryl group, but R may be absent; and ● represents $Y_1$ or $Y_2$.)

(10) The method for producing a mechanochromic luminescent material according to any of (7) to (9) above, wherein n is 0 or 1.

(11) A method for producing a mechanochromic resin including a step for mixing a mechanochromic luminescent material represented by formula (26) below, a polymerizable monomer, and a catalyst or initiator in an organic solvent.

[Chemical formula 12]

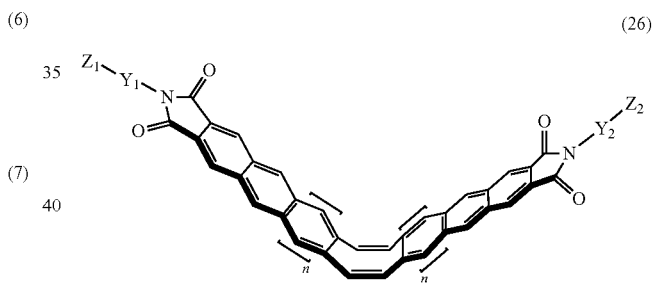
(26)

(In the formula, $Y_1$ and $Y_2$ represent substituents that inhibit aggregation of a mechanochromic luminescent material represented by formula (26), and may be the same or different. $Z_1$ and $Z_2$ represent polymerizable groups, and may be the same or different. n represents an integer of 0-3.)

(12) The method for producing a mechanochromic resin according to (11) above, wherein $Y_1$ and $Y_2$ are selected from the following substituents.

[Chemical formula 13]

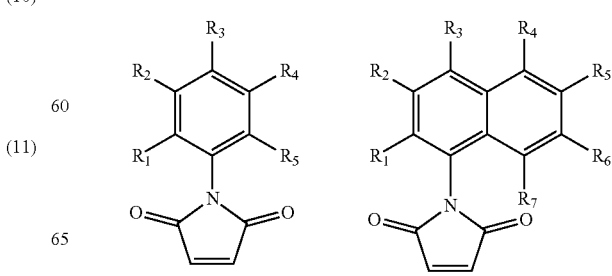

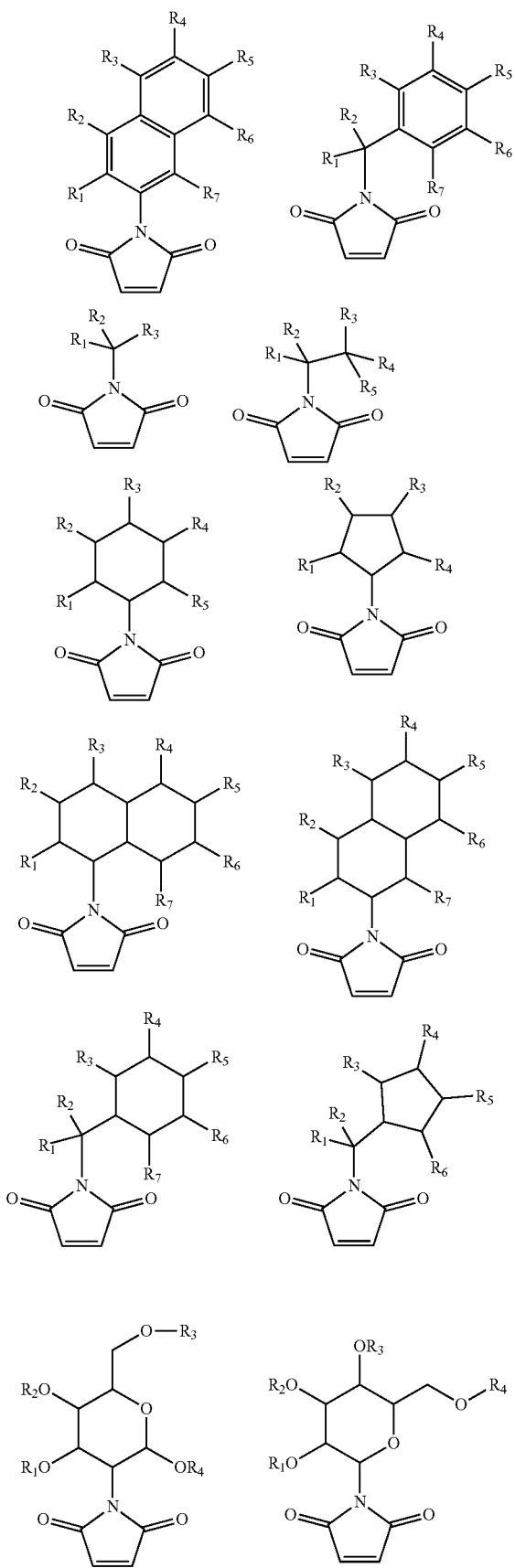

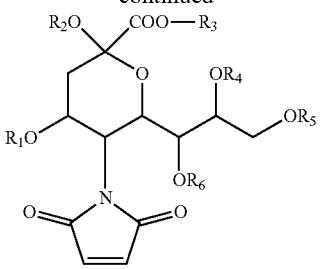

(Any one of the substituents $R_1$-$R_7$ represents a polymerizable group $Z_1$ or $Z_2$; $R_1$-$R_7$ other than the polymerizable group $Z_1$ or $Z_2$ represent H, a C1-20 linear, branched, or cyclic alkyl group, C6-20 aryl group, F, Cl, Br, I, $CF_3$, $CCl_3$, or $OCH_3$; and $R_1$-$R_7$ other than the polymerizable group $Z_1$ or $Z_2$ may be the same or different.)

(13) The method for producing a mechanochromic resin according to (11) or (12) above, wherein the polymerizable groups $Z_1$ and $Z_2$ are selected from the following substituents.

[Chemical formula 14]

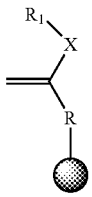

(3)

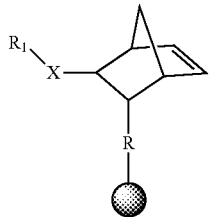

(4)

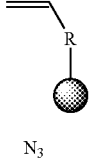

(5)

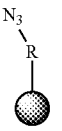

(6)

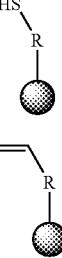

(7)

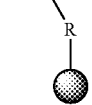

(8)

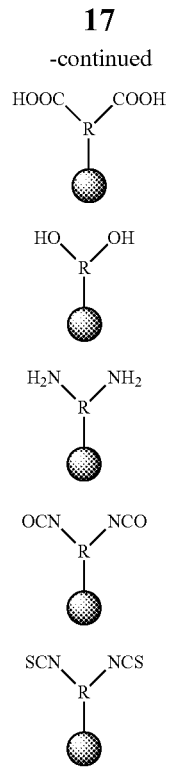

(9)
(10)
(11)
(12)
(13)

(In the above formulas (3) and (4), X represents an amide or ester, but may be absent; in the above formulas (3) and (4), $R_1$ is the same as $R_1$ in (12) above; in the above formulas (3) to (13), R represents a C1-20 linear, branched, or cyclic alkyl group or a C6-20 aryl group, but R may be absent; and ● represents $Y_1$ or $Y_2$.)

(14) The method for producing a mechanochromic resin according to any of (11) to (13) above, wherein n is 0 or 1.

Effect of the Invention

The mechanochromic resin of the present invention differs from the mechanochromic materials described in Non-patent Documents 1-7 and Patent Document 1 and makes it possible to visualize in real time the stress applied to a material since the luminescent color changes rapidly and reversibly due to stretching/contraction.

In addition, the mechanochromic luminescent material does not aggregate in the course of polymerization of the mechanochromic resin since a substituent that inhibits aggregation between the raw material, such as an anthraceneimide dimer, naphthaleneimide dimer, or the like, and the polymerizable group is introduced.

BRIEF DESCRIPTION OF THE DRAWINGS

FIG. 2(1) is a photograph of the compound A1 synthesized in Example 1 dissolved in chloroform; FIG. 2(2) is a photograph of the compound A2 synthesized in Comparative Example 1 suspended in chloroform;

FIG. 4(2) is a photograph substituted for a drawing and is a photograph of a gel-form solid of a film synthesized in Example 4 swollen by chloroform; FIG. 4(3) is a graph showing the emission spectra of each;

DESCRIPTION OF THE PREFERRED EMBODIMENTS

Figure 1:
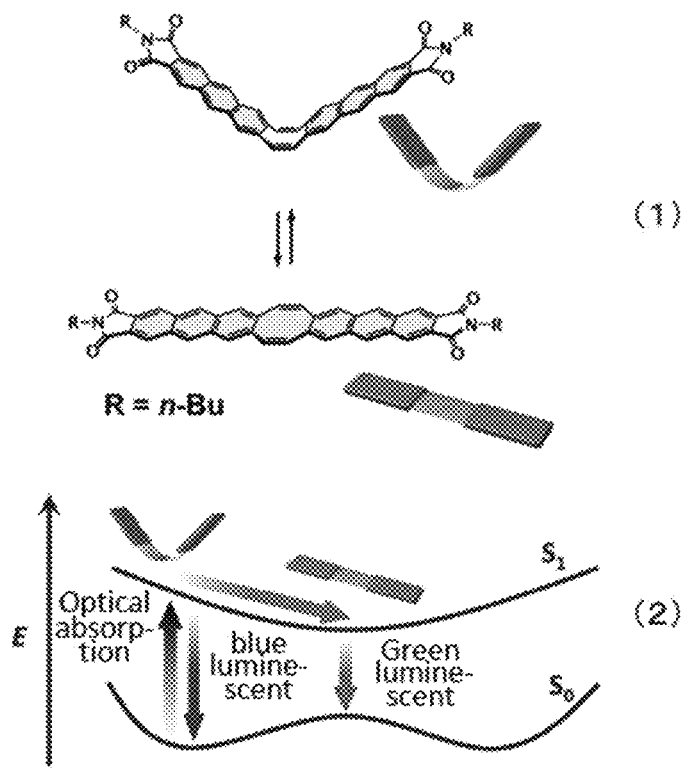
FIG. 1(1) and (2) show a compound obtained by fusing luminescent anthraceneimide as two rigid "wings" to opposite sides of a flexible conjugated eight-membered ring (cyclooctatetraene), described in Non-patent Document 5.

The mechanochromic luminescent material and mechanochromic resin obtained by crosslinking the mechanochromic luminescent material of the present invention are described in greater detail below.

First, in the present invention, the term "mechanochromic luminescent material" means a material that, due to mechanical stress, the wavelength at which light is emitted changes and the luminescent color changes. The term "mechanochromic resin" means a resin obtained by crosslinking a mechanochromic luminescent material to a polymer chain and is a resin for which the luminescent color changes due to expansion and contraction of the resin.

The mechanochromic resin of the present invention can be synthesized by crosslinking a mechanochromic luminescent material represented by formula (1) or formula (2) below to a polymer chain.

[Chemical formula 15]

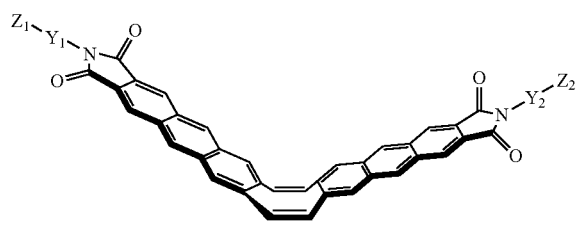

(1)

[Chemical formula 16]

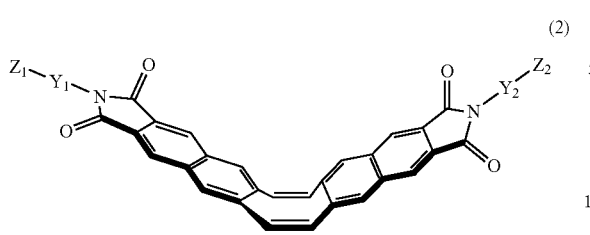

(2)

Y₁ and Y₂ in the above formula (1) or formula (2) represent substituents for inhibiting aggregation of the mechanochromic luminescent material represented by formula (1) or formula (2), and may be the same or different. Anthraceneimide dimers or naphthaleneimide dimers to which $Y_1$ and $Y_2$ of formula (1) or formula (2) and $Z_1$ and $Z_2$ are not bonded luminesce red or green, respectively, upon aggregation, as described in Non-patent Documents 5 and 6. However, due to this aggregation ability, they aggregate even in solvents used for a crosslinking reaction to a polymer chain, and a mechanochromic resin is difficult to obtain. The crosslinking reaction to a polymer chain is facilitated by introducing polymerizable groups $Z_1$ and $Z_2$ via the substituents for inhibiting aggregation shown by $Y_1$ and $Y_2$.

As mentioned above, $Y_1$ and $Y_2$ are not particularly restricted as long as they are substituents that can inhibit aggregation of a mechanochromic luminescent material represented by formula (1) or formula (2) in a solvent for a crosslinking reaction and can introduce a polymerizable group for crosslinking with a polymer chain. For example, the following substituents can be given as examples.

[Chemical formula 17]

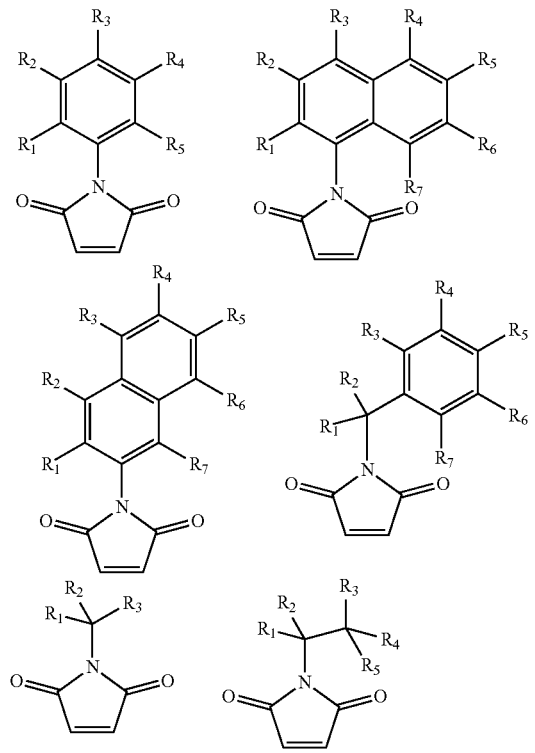

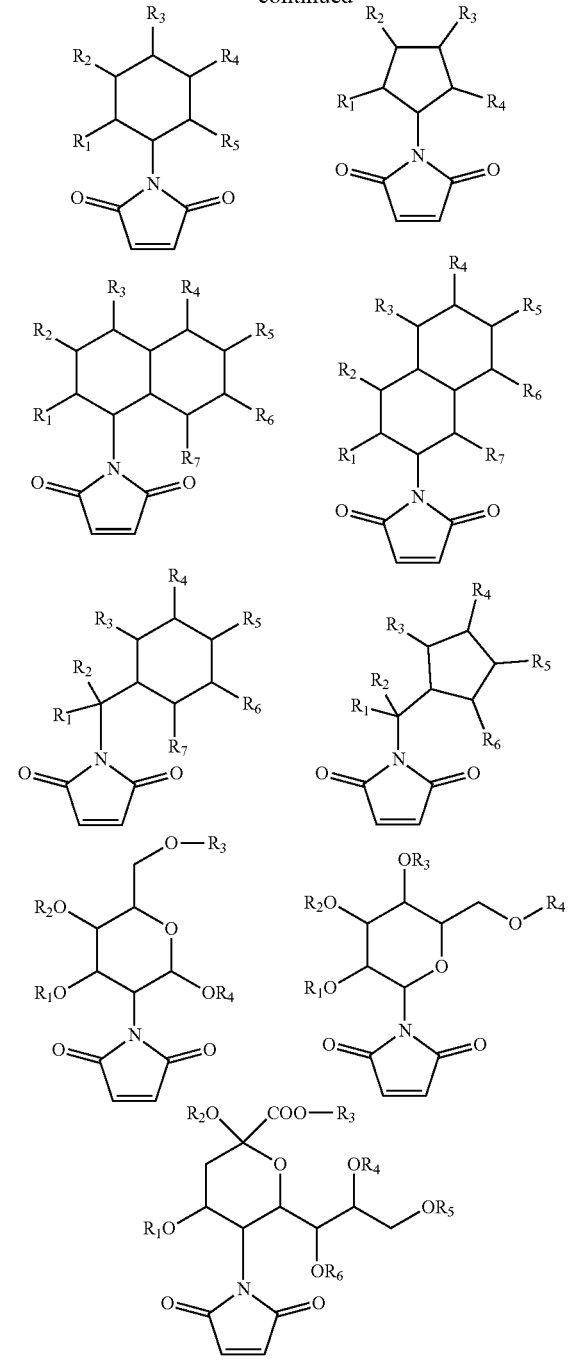

Any one of the substituents $R_1$-$R_7$ given as examples above represents a polymerizable group $Z_1$ or $Z_2$ to be described later. $R_1$-$R_7$, other than the polymerizable group $Z_1$ or $Z_2$-represent H, a C1-20 linear, branched, or cyclic alkyl group, C6-20 aryl group, F, Cl, Br, I, $CF_3$, $CCl_3$, or $OCH_3$. $R_1$-$R_7$ other than the polymerizable group $Z_1$ or $Z_2$ may be the same or different.

Concrete examples of C1-20 linear, branched, or cyclic alkyl groups include methyl, ethyl, n-propyl, 2-propyl, n-butyl, 1-methylpropyl, 2-methylpropyl, tert-butyl, n-pentyl, 1-methylbutyl, 1-ethylpropyl, tert-pentyl, 2-methylbutyl, 3-methylbutyl, 2,2-dimethylpropyl, n-hexyl, 1-methylpentyl, 1-ethylpentyl, 2-methylpentyl, 3-methylpentyl, 4-methylpentyl, 2-methylpentan-3-yl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl, 2-ethylbutyl, heptyl, octyl, nonyl, decyl, undecyl, dodecyl, tridecyl, tetradecyl, pentadecyl, hexadecyl, heptadecyl, octadecyl, nonadecyl, eicosyl, cyclopropyl, cyclobutyl, cyclopentyl, or cyclohexyl. C1-16 alkyl groups are preferred among the abovementioned alkyl groups.

Concrete examples of C6-20 aryl groups include phenyl, indenyl, pentalenyl, naphthyl, azulenyl, fluorenyl, phenanthrolenyl, anthracenyl, acenaphthylenyl, biphenylenyl, naphthacenyl, or pyrenyl.

The polymerizable groups $Z_1$ and $Z_2$ are not particularly restricted as long as they can bond with the substituent $Y_1$ or $Y_2$ and crosslink with a polymer chain. Examples include radical polymerizable monomers, metathesis ring-opening polymerizable monomers, click reaction monomers, bifunctional monomers, and the like.

Polymerizable groups represented by formula (3) below can be given as examples of radical polymerizable monomers.

[Chemical formula 18]

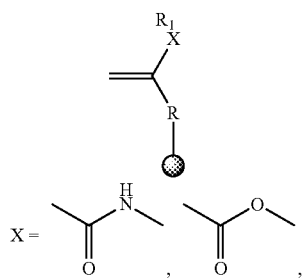

(3)

None

In the above formula (3), X represents an amide or ester, but may be absent. R represents a C1-20 linear, branched, or cyclic alkyl group or a C6-20 aryl group, but R may be absent. $R_1$ represents H, a C1-20 linear, branched, or cyclic alkyl group, C6-20 aryl group, F, Cl, Br, I, $CF_3$, $CCl_3$, or $OCH_3$. Furthermore, ● in formula (3) represents $Y_1$ or $Y_2$; the same is true in formulas (4)-(13) below. Examples of radical polymerizable monomers represented by the above formula (3) include methyl (meth)acrylamide, ethyl (meth)acrylamide, n-propyl (meth)acrylamide, 2-propyl (meth)acrylamide, n-butyl (meth)acrylamide, 1-methylpropyl (meth)acrylamide, 2-methylpropyl (meth)acrylamide, tert-butyl (meth)acrylamide, n-pentyl (meth)acrylamide, 1-methylbutyl (meth)acrylamide, 1-ethylpropyl (meth)acrylamide, tert-pentyl (meth)acrylamide, 2-methylbutyl (meth)acrylamide, 3-methylbutyl (meth)acrylamide, 2,2-dimethylpropyl (meth)acrylamide, n-hexyl (meth)acrylamide, and other such alkyl (meth)acrylamides; methyl (meth)acrylate, ethyl (meth)acrylate, n-propyl (meth)acrylate, 2-propyl (meth)acrylate, n-butyl (meth)acrylate, 1-methylpropyl (meth)acrylate, 2-methylpropyl (meth)acrylate, tert-butyl (meth)acrylate, n-pentyl (meth)acrylate, 1-methylbutyl (meth)acrylate, 1-ethylpropyl (meth)acrylate, tert-pentyl (meth)acrylate, 2-methylbutyl (meth)acrylate, 3-methylbutyl (meth)acrylate, 2,2-dimethylpropyl (meth)acrylate, n-hexyl (meth)acrylate, 1-methylpentyl (meth)acrylate, 1-ethylbutyl (meth)acrylate, 2-methylpentyl (meth)acrylate, 3-methylpentyl (meth)acrylate, 4-methylpentyl (meth)acrylate, 2-methylpentan-3-yl (meth)acrylate, 3,3-dimethylbutyl (meth)acrylate, 2,2-dimethylbutyl (meth)acrylate, 1,1-dimethylbutyl (meth)acrylate, 1,2-dimethylbutyl (meth)acrylate, 1,3-dimethylbutyl (meth)acrylate, 2,3-dimethylbutyl (meth)acrylate, 1-ethylbutyl (meth)acrylate, 2-ethylbutyl (meth)acrylate, heptyl (meth)acrylate, and other such alkyl (meth)acrylates; propylene, 2-methyl-1-propylene, 1-butene, 2-methyl-1-butene, 3-methyl-1-butene, 3,3-dimethyl-1-butene, 3-methyl-2-ethyl-1-butene, 2,3-dimethyl-1-butene, 2-tert-butyl-3,3-dimethyl-1-butene, 1-pentene, 2-methyl-1-pentene, 3-methyl-1-pentene, 4-methyl-1-pentene, 2-methyl-3-ethyl-1-pentene, 2,4,4-trimethyl-1-pentene, 1-hexene, and other such cyclopentenes or cyclohexenes; vinylbenzene (styrene), 1-vinylindene, 5-vinylindene, 1-vinylpentalene, 1-vinylnaphthalene, 2-vinylnaphthalene, 2-vinylazulene, 9-vinyl-9H-fluorene, 2-vinyl-9H-fluorene, 1-vinylphenanthrolene, 2-vinylphenanthrolene, 3-vinylphenanthrolene, 6-vinylphenanthrolene, 8-vinylphenanthrolene, 1-vinylanthracene, 2-vinylanthracene, 9-vinylanthracene, 1-vinylacenaphthylene, 2-vinylbiphenylene, 1-vinylnaphthacene, 2-vinylnaphthacene, 1-vinylpyrene, 4-vinylpyrene, and other such vinylaryls; and the like.

Polymerizable groups represented by formula (4) below can be given as examples of metathesis ring-opening polymerizable monomers.

[Chemical formula 19]

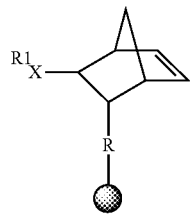

(4)

In the above formula (4), X, $R_1$, and R are the same as in formula (3). Examples of metathesis ring-opening polymerizable monomers represented by formula (4) above include norbornene, acetyl norbornene, 5-methyl norbornene, 5-ethyl norbornene, 5-butyl norbornene, 5-phenyl norbornene, 5-benzyl norbornene, 5-acetyl norbornene, 5-acetyloxy norbornene, 5-methoxycarbonyl norbornene, 5-ethoxycarbonyl norbornene, 5-methyl-5-methoxycarbonyl norbornene, and the like.

Polymerizable groups represented by formulas (5)-(8) below can be given as examples of click reaction monomers.

[Chemical formula 20]

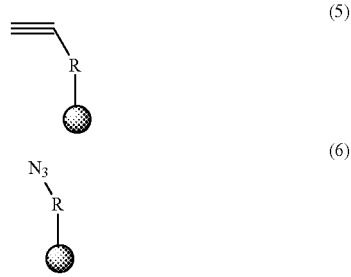

(5)

(6)

-continued

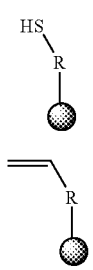

(7)

(8)

In the above formulas (5)-(8), R is the same as R in formula (3). Examples of monomers represented by formula (5) above include methylacetylene, ethylacetylene, propylacetylene, butylacetylene, pentylacetylene, hexylacetylene, cyclopropylacetylene, phenylacetylene, and the like. Examples of monomers represented by formula (6) above include methyl azide, ethyl azide, propyl azide, butyl azide, pentyl azide, hexyl azide, cyclopropyl azide, phenyl azide, and the like. Examples of monomers represented by formula (7) above include methyl thiol, ethyl thiol, propyl thiol, butyl thiol, pentyl thiol, hexyl thiol, cyclopropyl thiol, thiophenol, and the like. Examples of monomers represented by formula (8) above include vinyl, ethyl vinyl, propyl vinyl, butyl vinyl, pentyl vinyl, hexyl vinyl, cyclopropyl vinyl, phenyl vinyl, and the like. Furthermore, an azide and alkyne, and a vinyl and thiol react in the case of a click reaction. Therefore, when monomers of formula (5) are used as polymerizable groups $Z_1$ or $Z_2$, a monomer having an azide may be used as the polymerizable monomer that constructs the polymer chain described below. Similarly, a polymerizable monomer having an alkyne may be used when monomers of formula (6) are used as polymerizable groups $Z_1$ or $Z_2$; a polymerizable monomer having a vinyl may be used when monomers of formula (7) are used as polymerizable groups $Z_1$ or $Z_2$; and a polymerizable monomer having a thiol may be used when monomers of formula (8) are used as polymerizable groups $Z_1$ or $Z_2$.

Polymerizable groups represented by formulas (9)-(13) below can be given as examples of bifunctional monomers.

Chemical formula 21]

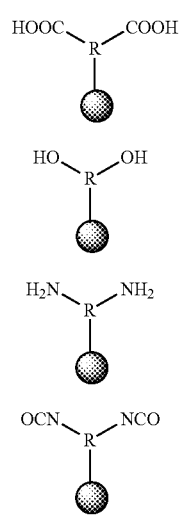

(9)

(10)

(11)

(12)

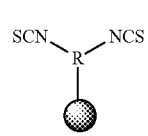

(13)

In the above formulas (9)-(13), R is the same as R in formula (3). Examples of monomers represented by formula (9) above include methyl dicarboxylic acid, ethyl dicarboxylic acid, propyl dicarboxylic acid, butyl dicarboxylic acid, pentyl dicarboxylic acid, hexyl dicarboxylic acid, cyclopropyl dicarboxylic acid, phenyl dicarboxylic acid, and the like. Examples of monomers represented by formula (10) above include methyl diol, ethyl diol, propyl diol, butyl diol, pentyl diol, hexyl diol, cyclopropyl diol, phenyl diol, and the like. Examples of monomers represented by formula (11) above include methyldiamine, ethyldiamine, propyldiamine, butyldiamine, pentyldiamine, hexyldiamine, cyclopropyldiamine, phenyldiamine, and the like. Examples of monomers represented by formula (12) above include methyl dicyanate, ethyl dicyanate, propyl dicyanate, butyl dicyanate, pentyl dicyanate, hexyl dicyanate, cyclopropyl dicyanate, phenyl dicyanate, and the like. Examples of monomers represented by formula (13) include methyl dithiocyanate, ethyl dithiocyanate, propyl dithiocyanate, butyl dithiocyanate, pentyl dithiocyanate, hexyl dithiocyanate, cyclopropyl dithiocyanate, phenyl dithiocyanate, and the like. As with a click reaction, a polymerizable monomer capable of reacting with the bifunctional monomer may be selected as is appropriate as a polymerizable monomer for the polymer chain when a bifunctional monomer is used as well. For example, when the polymerizable group includes a dicarboxylic acid, a polymerizable monomer including a diamine or diol may be selected.

A mechanochromic luminescent material represented by formula (1) or formula (2) above can be synthesized, for example, by the following procedures. Furthermore, the following synthesis methods are merely examples; other methods are also acceptable.

[Chemical formula 22]

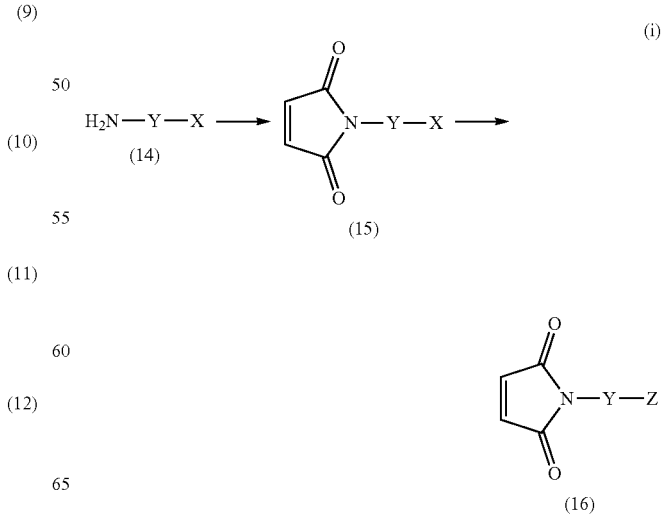

(i)

(14)

(15)

(16)

-continued (ii)

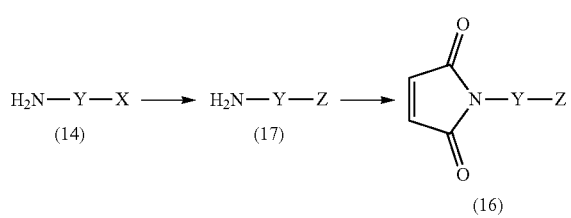

(iii)

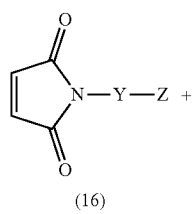

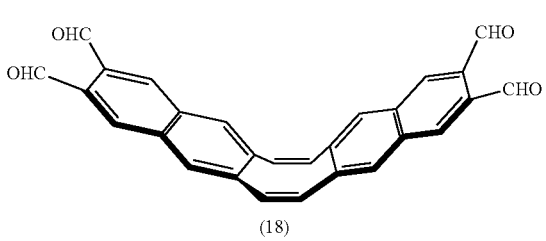
(18)

or

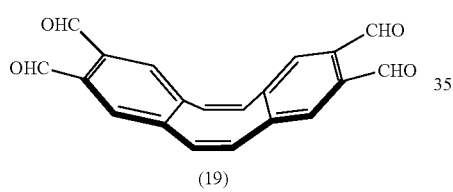
(19)

First, (i) a compound of formula (14) in which the moiety of a polymerizable group Z ($Z_1$ and $Z_2$ are collectively termed Z) bonded to a substituent Y ($Y_1$ and $Y_2$ are collectively termed Y) for inhibiting aggregation of the mechanochromic luminescent material is X (I, Br, Cl, or other such halogen) is reacted with maleic anhydride and imidated to obtain a compound of formula (15). Next, a compound of formula (16) in which X is substituted by the polymerizable group Z is obtained by a coupling reaction. (ii) As another method, a compound of formula (17) in which X is substituted by a polymerizable group Z is obtained first by a coupling reaction using a compound of formula (14). Next, the compound of formula (17) may be reacted with maleic anhydride and imidated to obtain a compound of formula (16). (iii) A mechanochromic luminescent material represented by formula (1) or formula (2) of the present invention to be used to produce a mechanochromic resin can be obtained by reacting a compound of formula (16) with a compound of formula (18) or a compound of formula (19) by Wittig olefination followed by an acene elongation reaction by Knoevenagel condensation.

Furthermore, compounds represented by the above formulas (18) and (19) can be synthesized by the following procedure described in the Supporting Information S3 of Non-patent Document 5.

[Chemical formula 23]

As shown by the above procedure, a compound (9 above) represented by formula (18) can be synthesized by adding a benzene ring to a compound (6 above) represented by formula (19) by the procedure of 6→7→8→9. Therefore, since the number of benzene rings can be adjusted by repeating the above procedure of 6→7→8→9, compounds that serve as the raw material of the mechanochromic luminescent materials of the present invention can be represented by formula (25) below.

[Chemical formula 24]

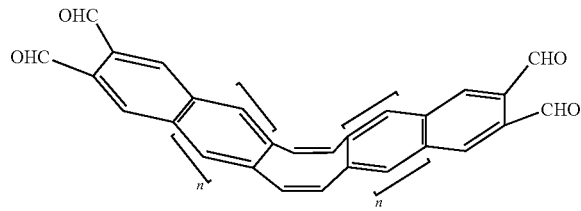

(25)

In the above formula, n represents an integer of 0-3.

Thus, a mechanochromic luminescent material represented by formula (26) can be synthesized by reacting with a compound represented by formula (16) in the same way as above, regardless of the n number, when a compound represented by formula (25) is used as the raw material as well.

[Chemical formula 25]

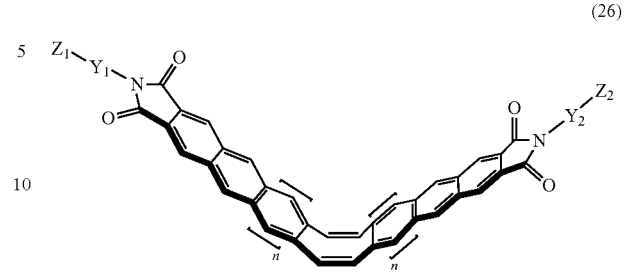

(26)

In the above formula, n represents an integer of 0-3. $Y_1$, $Y_2$, $Z_1$, and $Z_2$ are the same as above.

Concrete examples of mechanochromic luminescent materials included in formula (26) are given below, but the following examples are intended only to deepen understanding; compounds are not limited to the mechanochromic luminescent materials given as examples.

[Chemical formula 26]

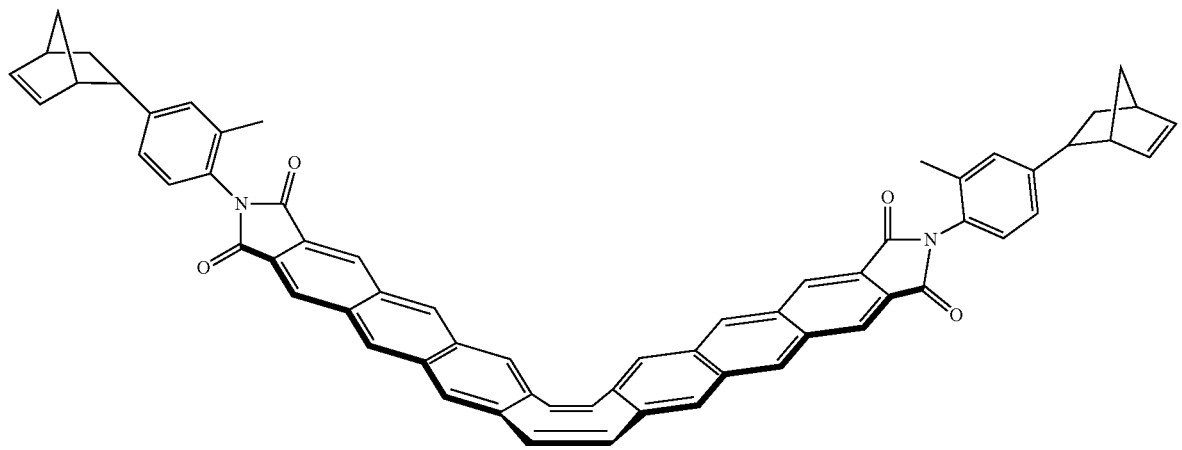

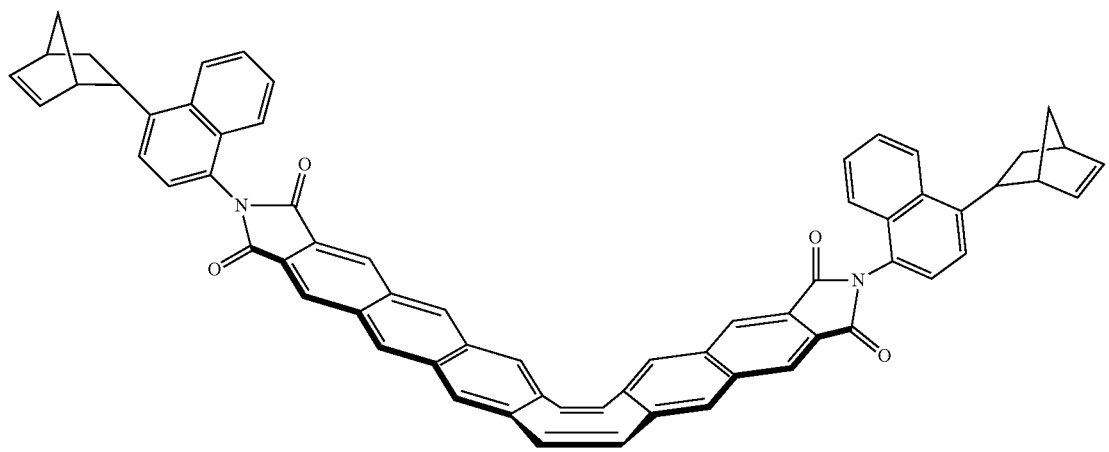

-continued
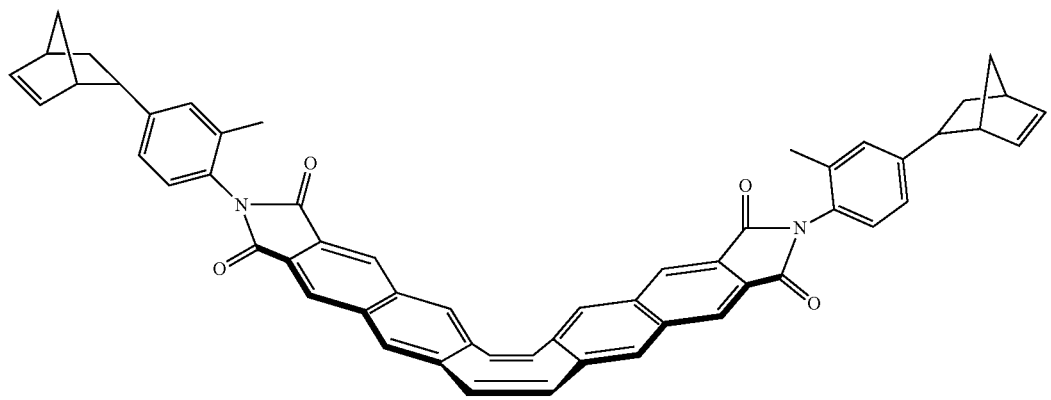
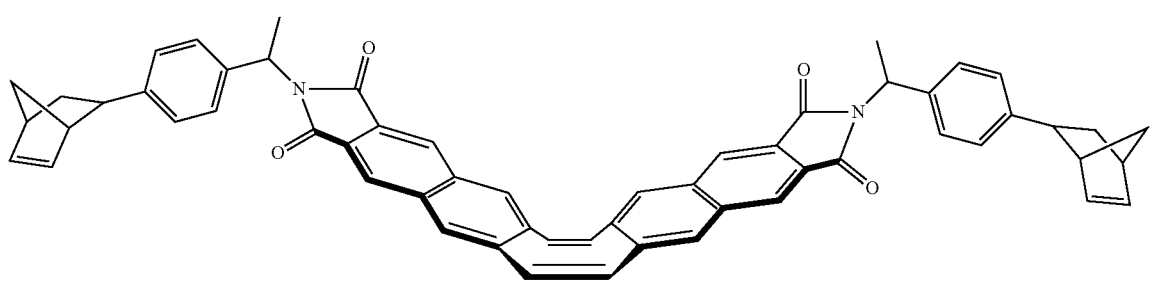
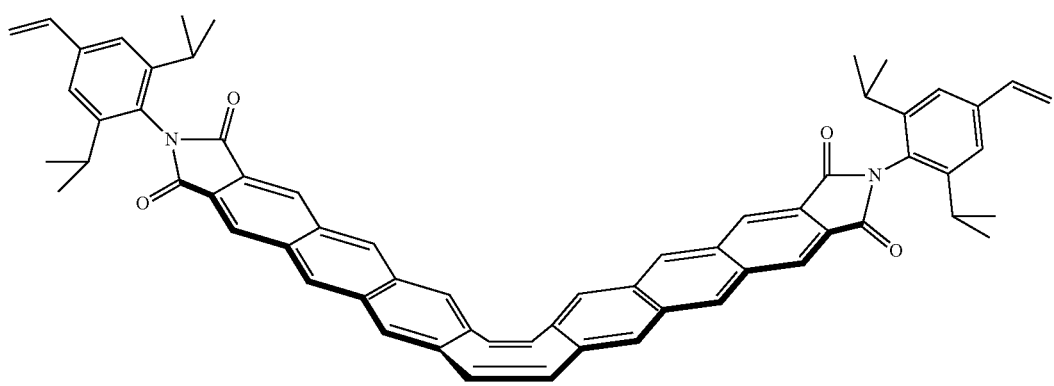
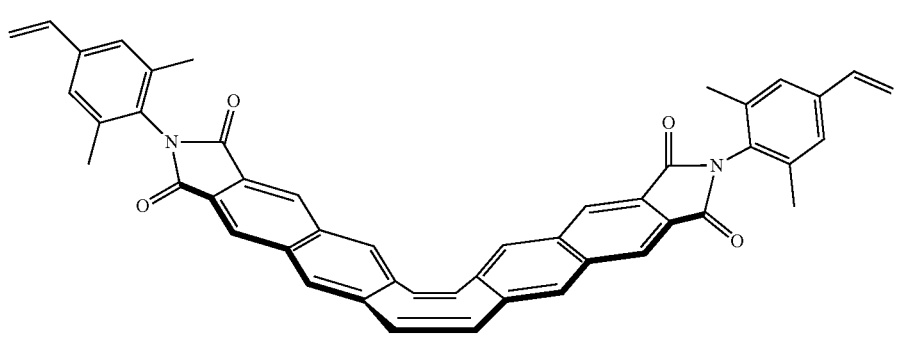

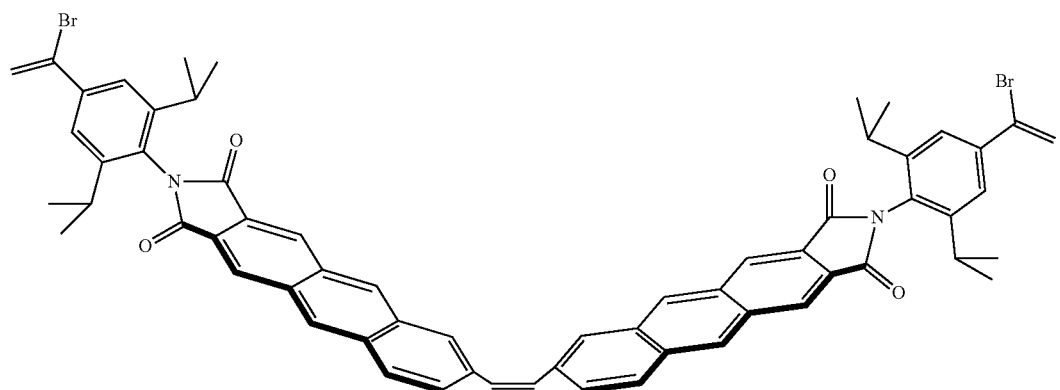
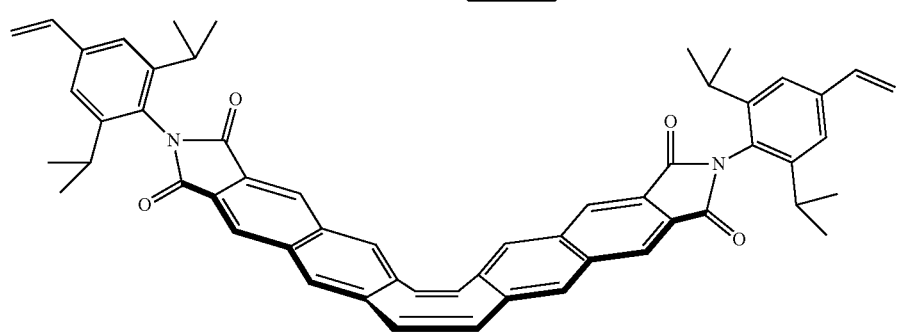
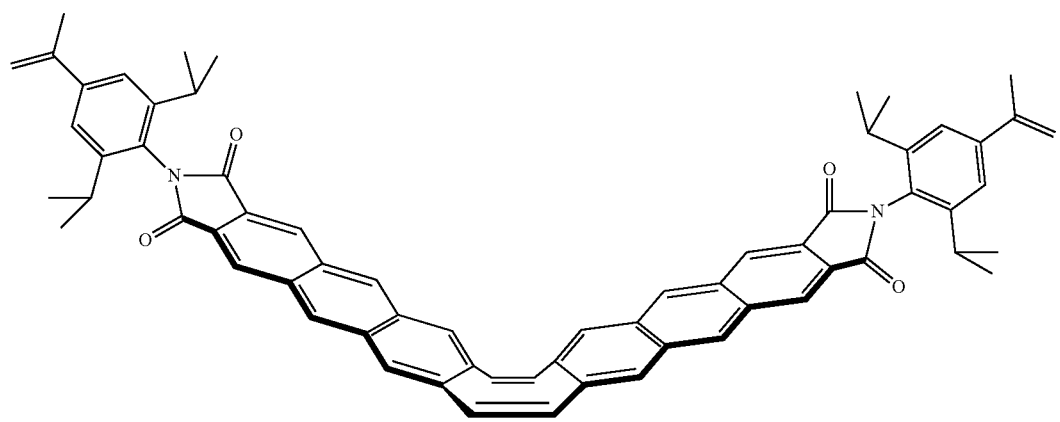
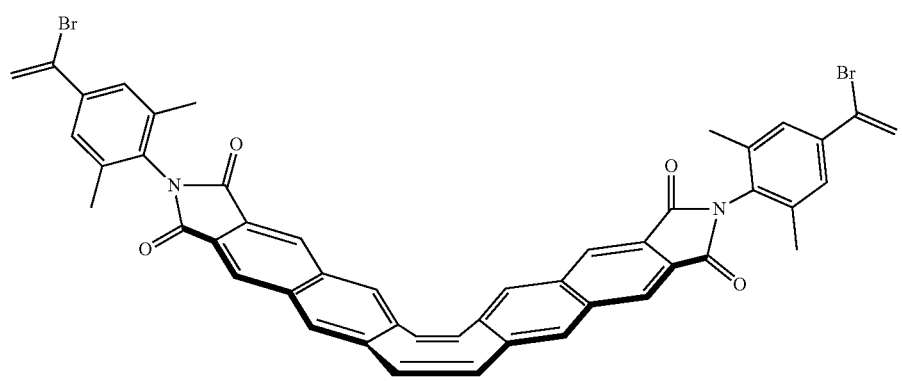

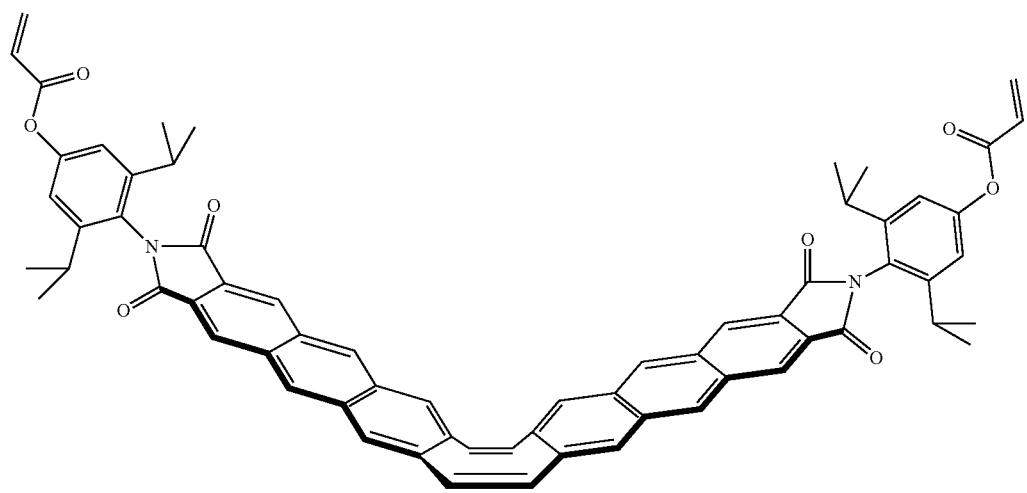
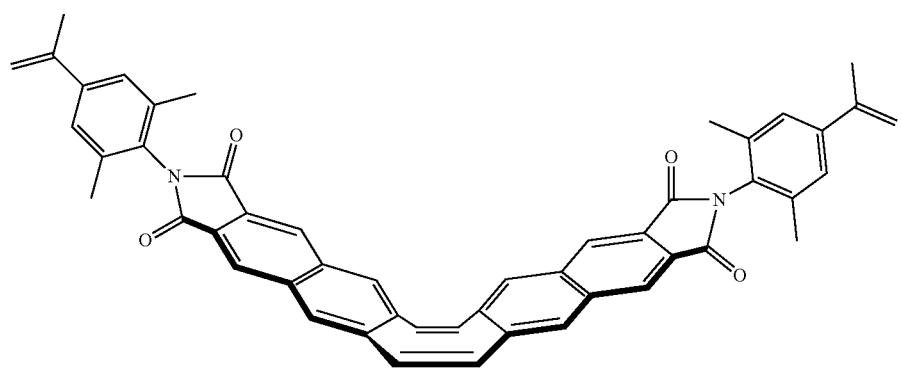
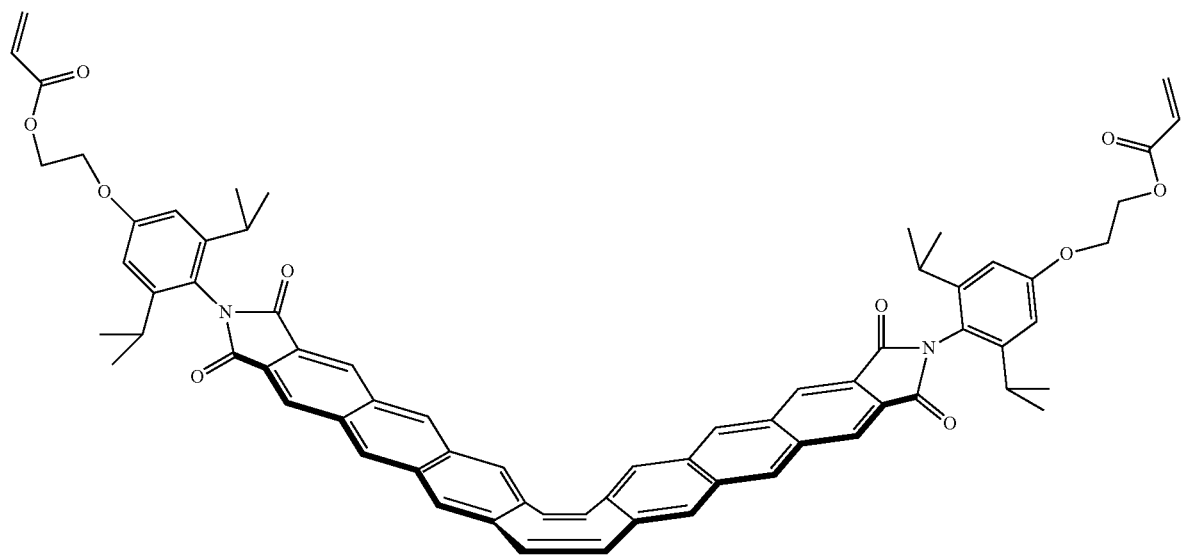

-continued
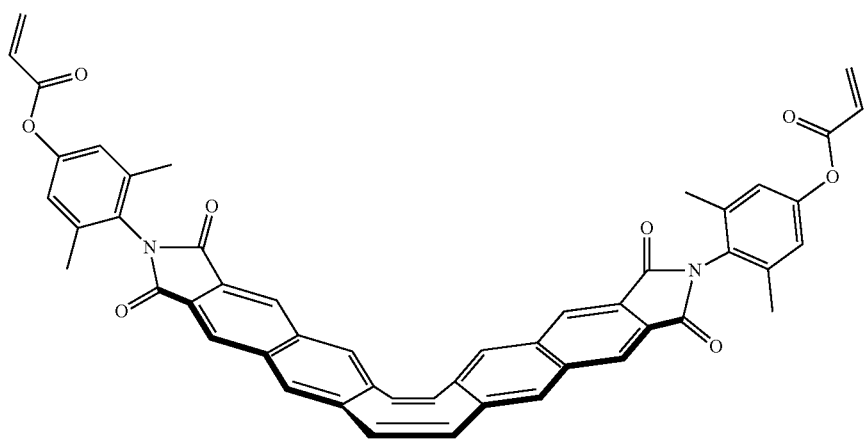
[Chemical formula 27]
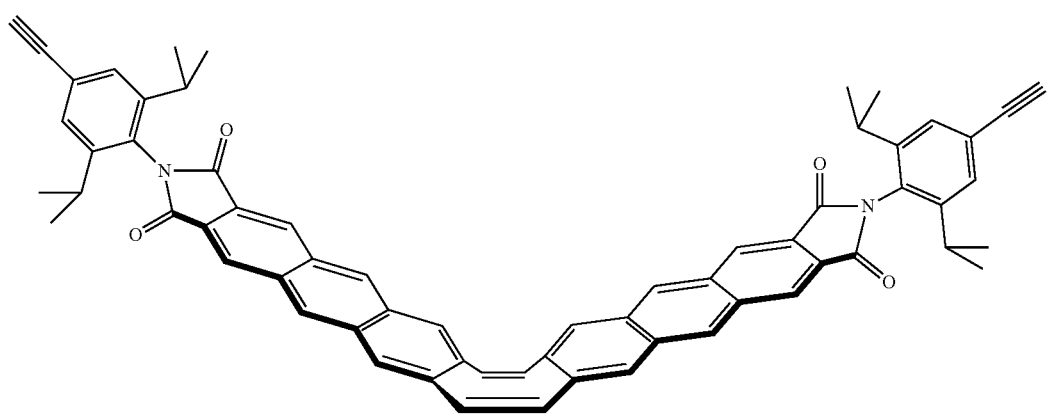
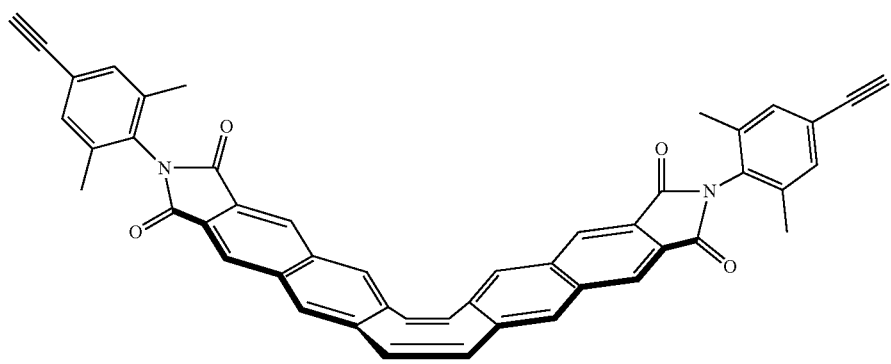
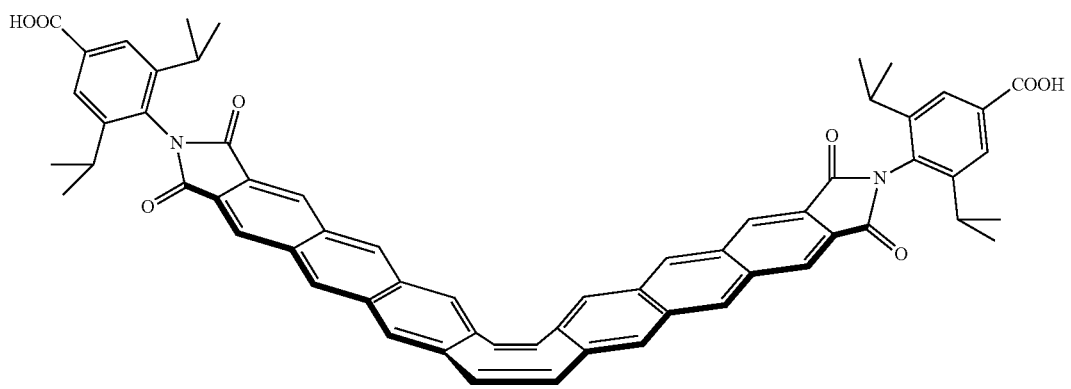

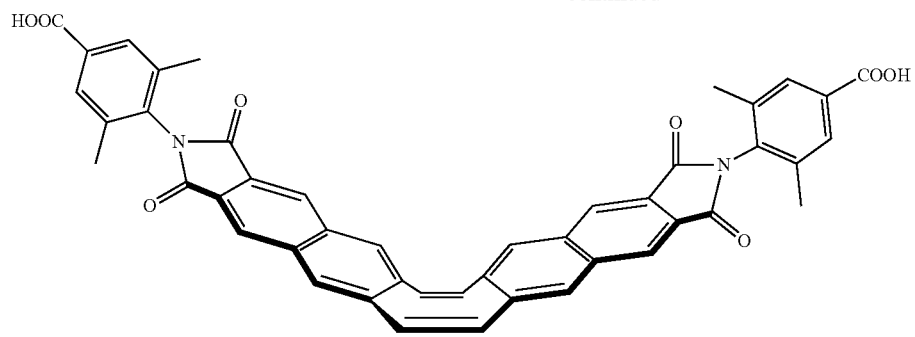
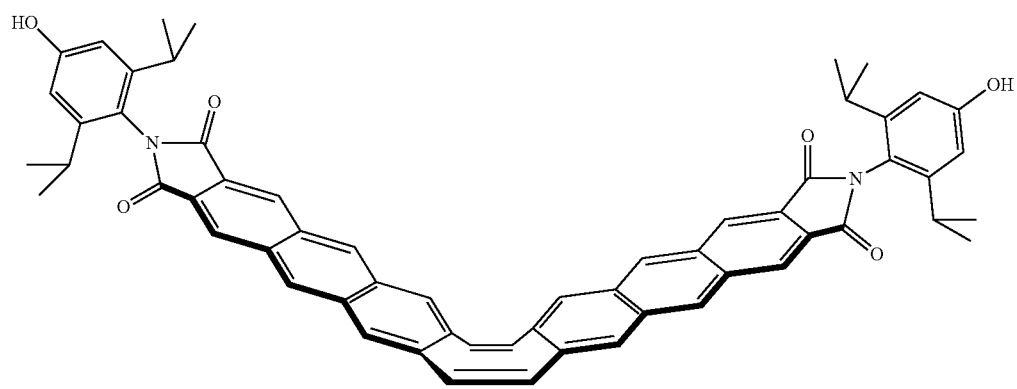
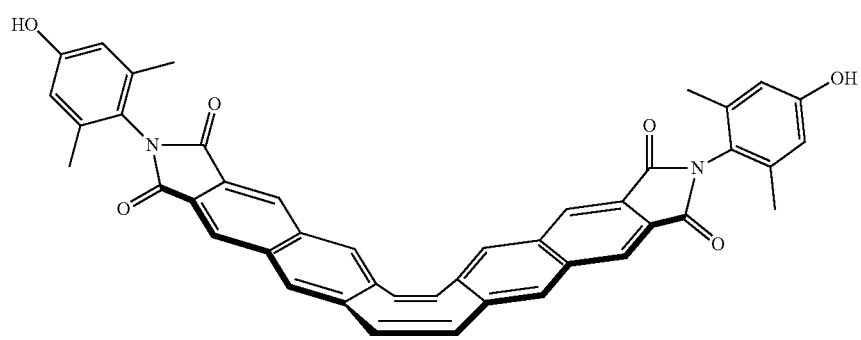
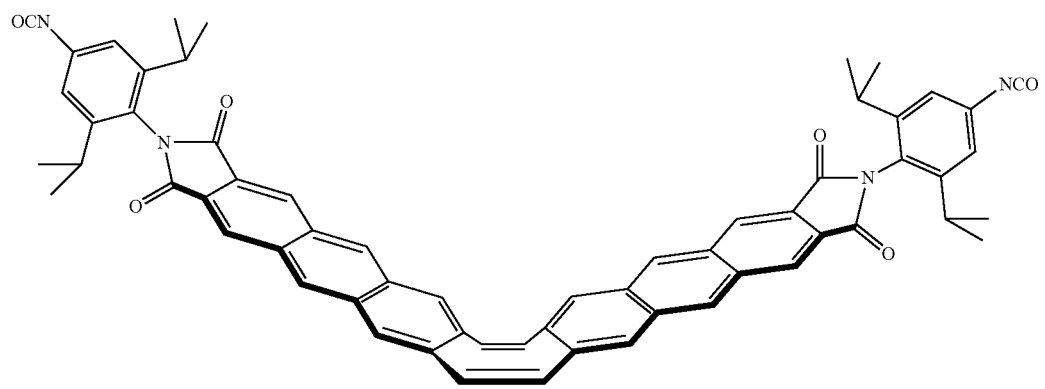

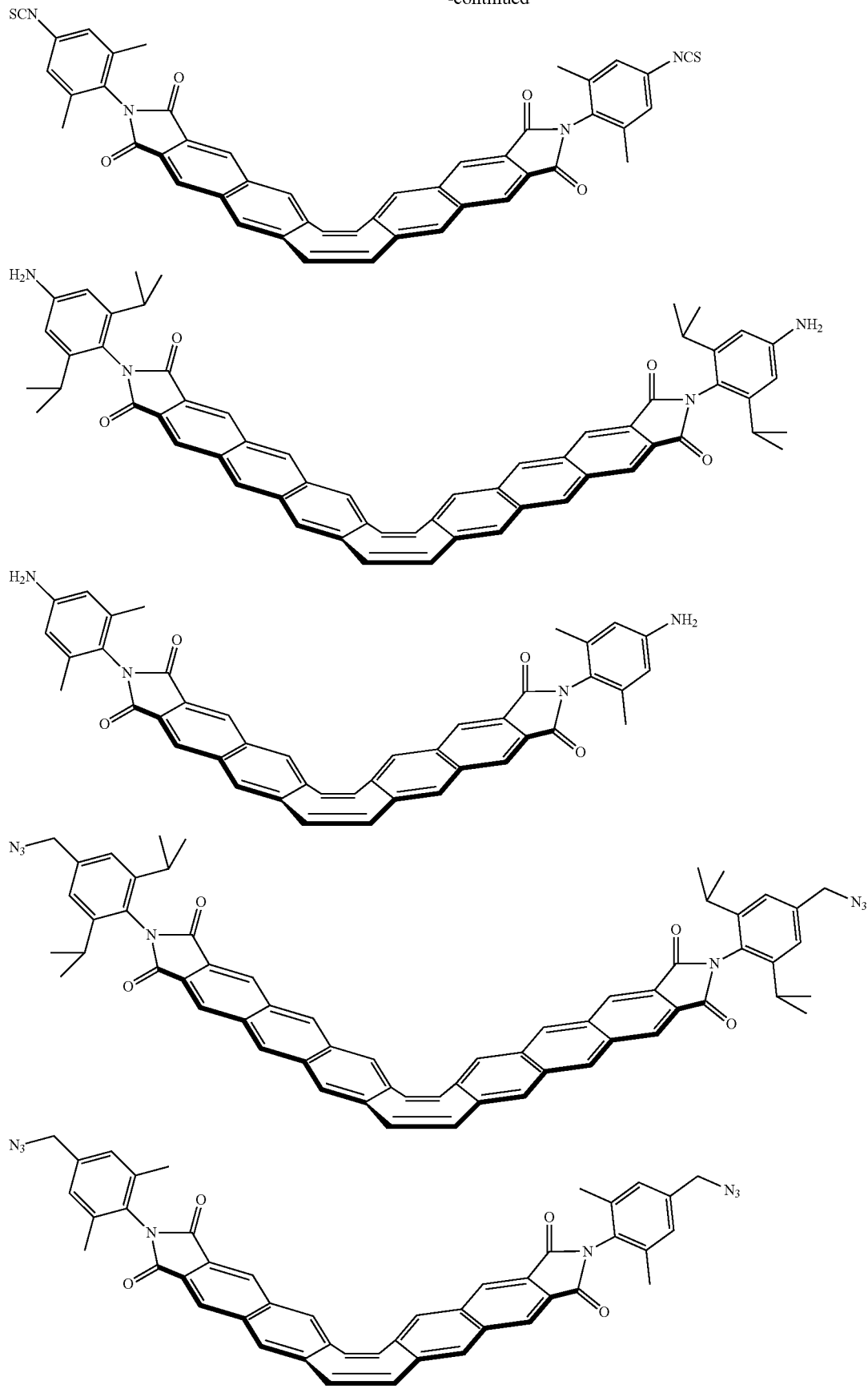

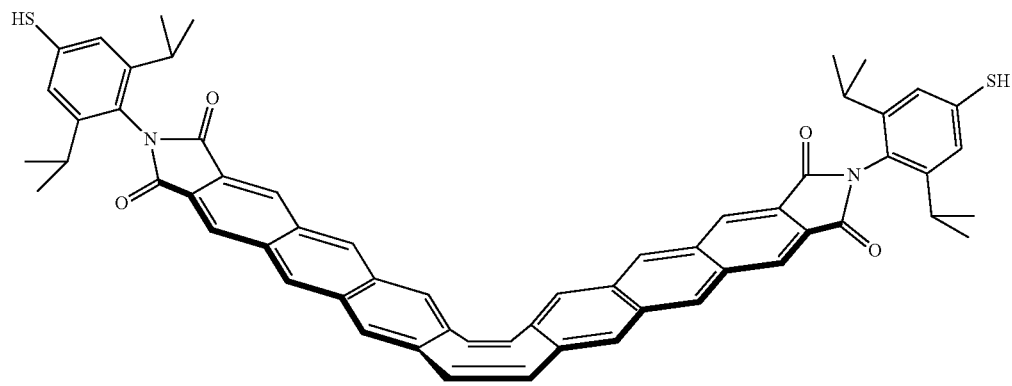
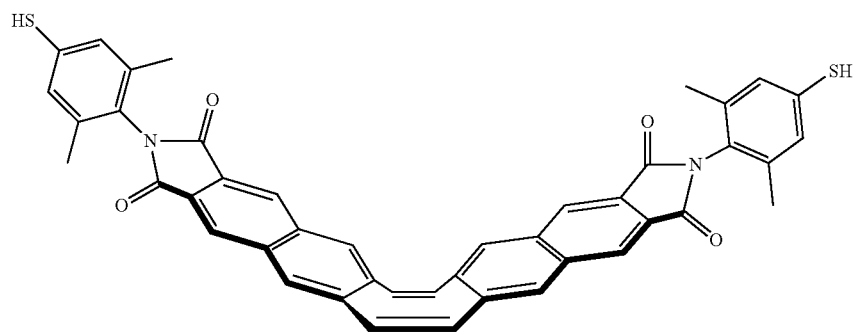
[Chemical formula 28]
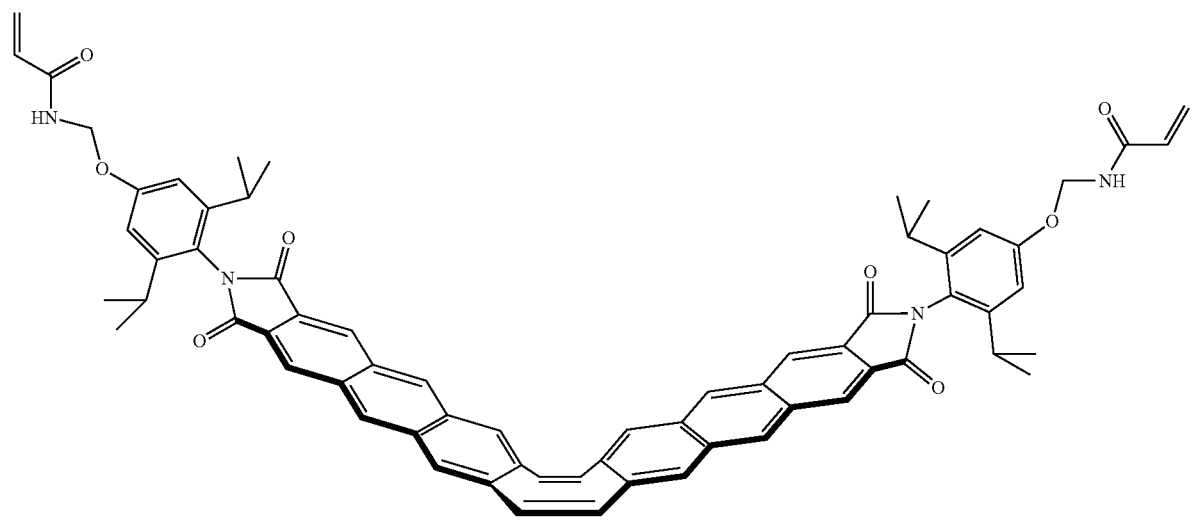

-continued
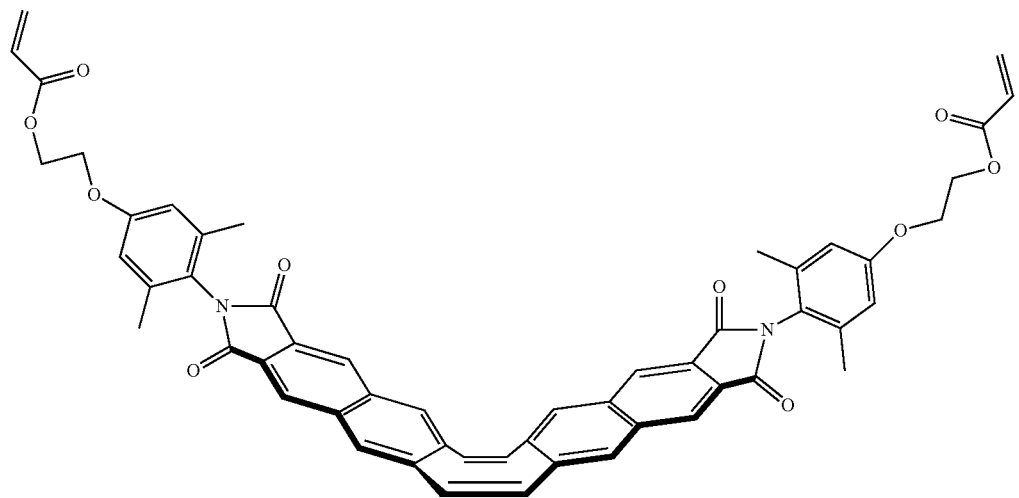
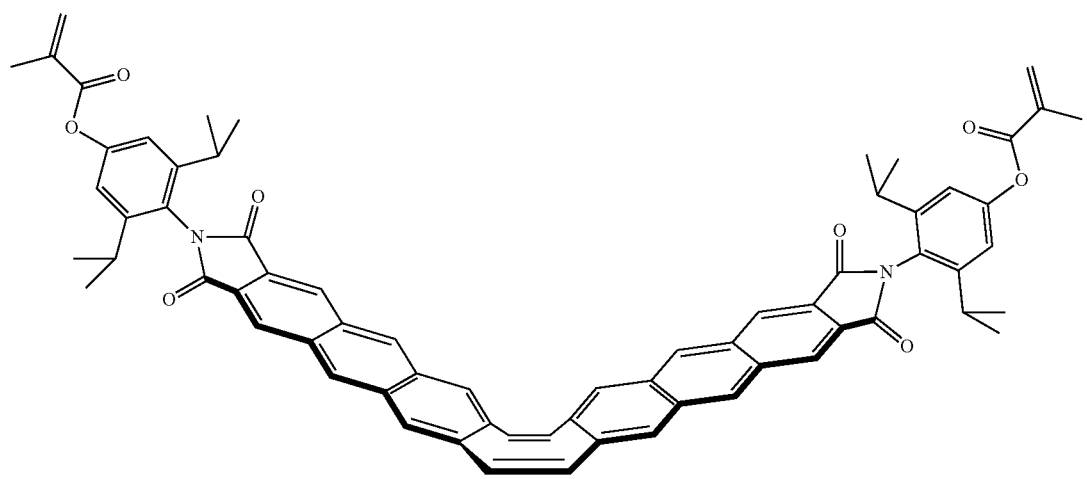
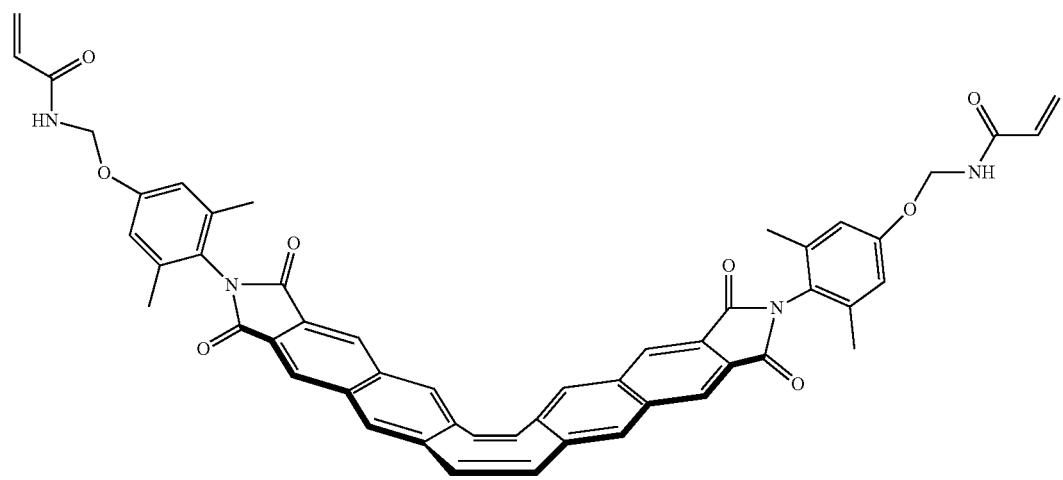

-continued
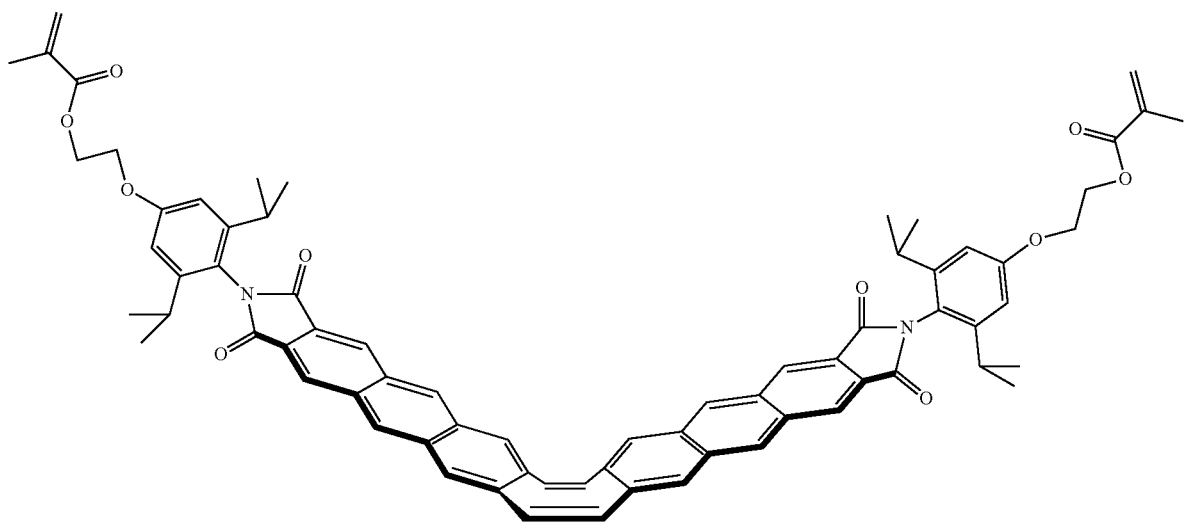
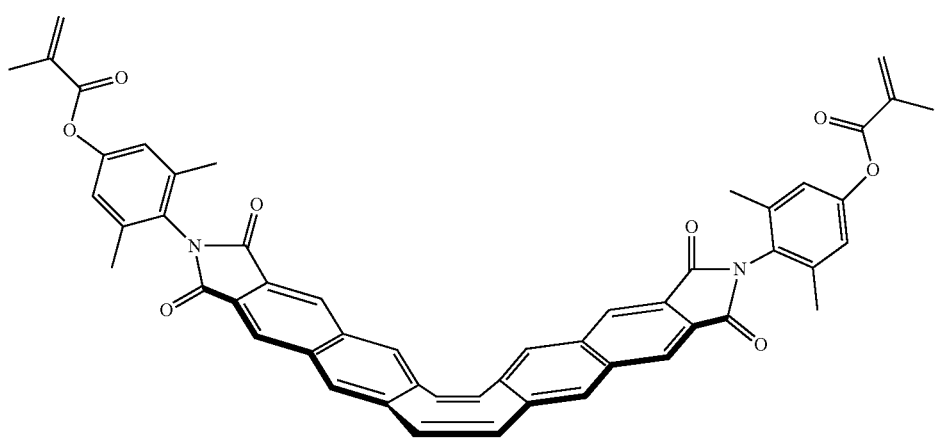
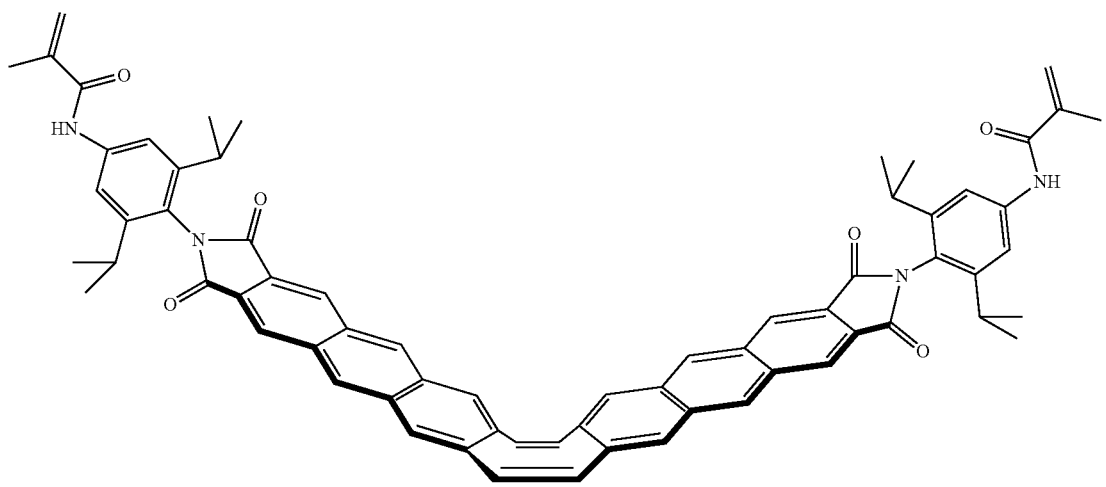

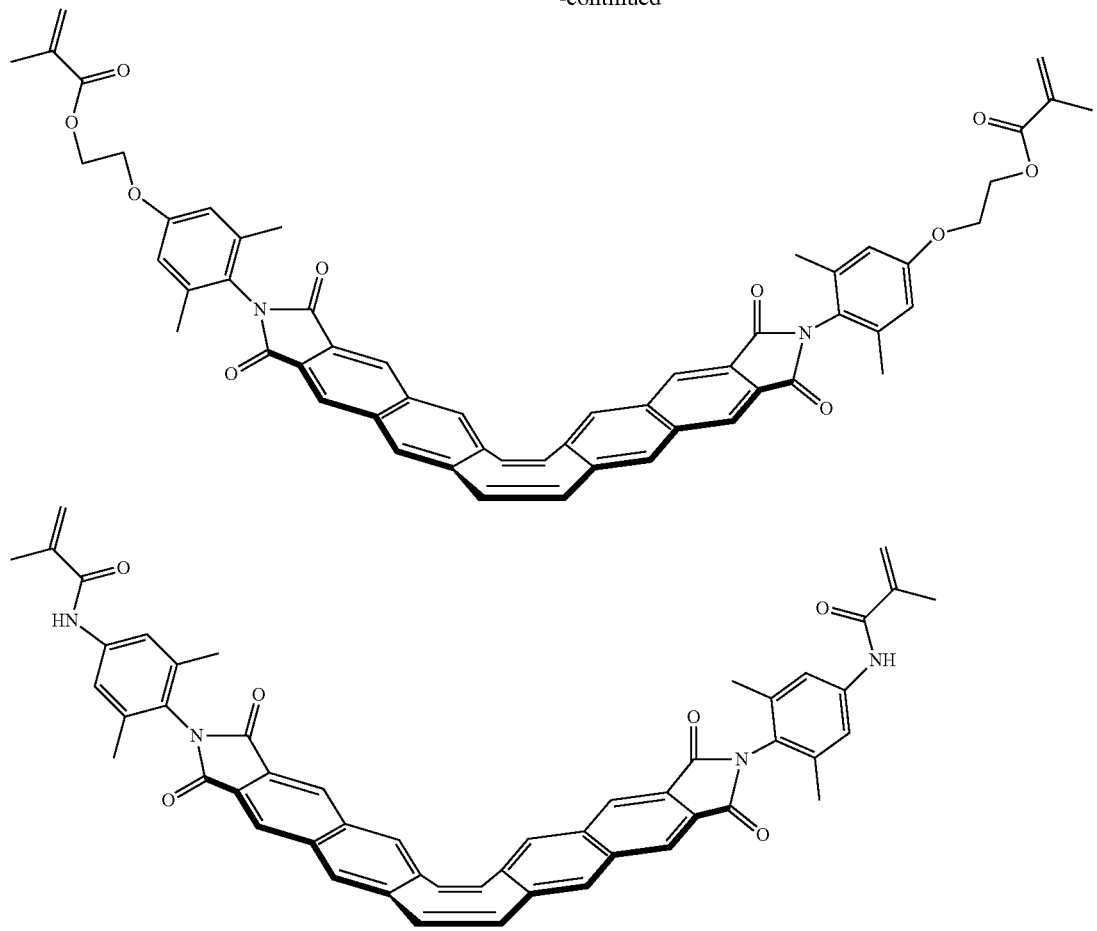

A mechanochromic resin of the present invention can be synthesized by mixing a mechanochromic luminescent material represented by the above formula (26), a polymerizable monomer, and a catalyst or initiator in an organic solvent.

The polymerizable monomer that constitutes the polymer chain is not particularly restricted as long as the monomer can crosslink the mechanochromic luminescent material of the present invention and the mechanochromic resin can expand and contract after synthesis. Examples of polymerizable monomers include monomers capable of ring-opening polymerization, radical polymerization, condensation polymerization, and click reaction.

Examples of monomers capable of ring-opening polymerization include norbornene, acetyl norbornene, ethylene oxide, propylene oxide, ethylene imine, trimethylene oxide, tetrahydrofuran, β-propiolactone, γ-butyrolactone, ε-caprolactone, and the like.

Examples of monomers capable of radical polymerization include ethylene, vinyl aromatic monomers, for example, styrene, α-methylstyrene, o-chlorostyrene, or vinyl toluene, esters of vinyl alcohol and monocarboxylic acids having 1-18 carbon atoms, for example, vinyl acetate, vinyl propionate, vinyl-n-butyrate, vinyl laurate, and vinyl stearate, advantageously, esters of α,β-monoethylenic unsaturated monocarboxylic acids and dicarboxylic acids having 3-6 carbon atoms, especially acrylic acid, methacrylic acid, maleic acid, fumaric acid, and itaconic acid, and alkanols generally having 1-12, advantageously having 1-8, and especially having 1-4 carbon atoms, for example, especially methyl acrylate, methyl methacrylate, ethyl acrylate, ethyl methacrylate, n-butyl acrylate, n-butyl methacrylate, isobutyl acrylate, isobutyl methacrylate, and 2-ethylhexyl acrylate, 2-ethylhexyl methacrylate, dimethyl maleate, di-n-butyl maleate, nitriles of α,β-monoethylenic unsaturated carboxylic acids, for example, acrylonitrile, and C4-C8 conjugated dienes, for example, 1,3-butadiene and isoprene, and the like.

Examples of monomers capable of condensation polymerization include monomers including polymerizable groups given as examples for the above formulas (9)-(13). Polymerizable monomers having an azide may be used as monomers capable of a click reaction when a monomer of formula (5) is used as the polymerizable group $Z_1$ or $Z_2$, as described above. Similarly, polymerizable monomers having an alkyne may be used when a monomer of formula (6) is used as the polymerizable group $Z_1$ or $Z_2$; polymerizable monomers having a vinyl may be used when a monomer of formula (7) is used as the polymerizable group $Z_1$ or $Z_2$; and polymerizable monomers having a thiol may be used when a monomer of formula (8) is used as the polymerizable group $Z_1$ or $Z_2$.

The above monomers may be used individually or a random copolymer may be made by using two or more types during synthesis.

The catalyst or initiator is not particularly restricted as long as a mechanochromic resin can be synthesized from the polymerizable monomer and mechanochromic luminescent material. Examples of catalysts include a Grubb's catalyst, Hoveyda-Grubb's catalyst, Ru complexes, tungsten chloride, tetramethyl tin, and the like. Examples of initiators include azobisisobutyronitrile, benzoyl peroxide, di-tert-butyl peroxide, hydrogen peroxide-iron(II) salt, persulfate-sodium bisulfite, triethylborane, and the like.

The mechanochromic resin synthesized can be represented, for example, by formula (20) below.

[Chemical fromula 29]

(20)

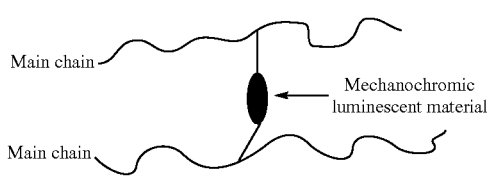

For the main chain, the above-mentioned polymerizable monomer may be selected as is appropriate to obtain the desired resin properties. For example, when one wishes to synthesize a hard mechanochromic resin (high Tg/high yield stress/low elongation), a polymerizable monomer that gives a main chain such as polystyrene, polymethyl methacrylate, or the like may be used. When one wishes to synthesize a soft mechanochromic resin (low Tg/low yield stress/high elongation), a polymerizable monomer that gives a main chain such as polyurethane, polybutadiene, polyacetyl norbornene, polydimethylsiloxane, or the like may be used.

The mechanochromic resin of the present invention changes color reversibly and instantaneously due to expansion or contraction. The changed luminescent color also lasts for a long time while a load is applied. Therefore, the mechanochromic resin can be made into a film shape and used as a tension sensor by adhering the end portion of the film to the object to be measured. It is also possible to instantaneously observe which part of a structure is under load by applying the resin in the form of a thin film to the surface of structures such as buildings, bridge piers, and the like.

The mechanochromic resin may also be made into fibers. It can be used as a tension sensor since which parts of the garment are under load during exercise can be observed, for example, if it is woven into the fabric of sportswear. It can also be used for fashion since the color of the clothing can change in accordance with the movement of the body when woven into the fabric of ordinary clothes. The distribution of pressure in a filter can also be examined if it is woven into industrial air filters, filtration filters, and the like.

The present invention is described concretely below through examples. These examples, however, are provided merely as a reference to concrete embodiments to explain the present invention. These examples are intended to explain specific concrete embodiments of the present invention, but do not represent any limitation or restriction of the scope of the invention disclosed in this application.

EXAMPLES

Synthesis of a Mechanochromic Luminescent Material

Example 1

A n-conjugated compound (compound A1) of anthraceneimide dimer and norbornene crosslinked by 2-methylphenyl groups was synthesized by the procedure described below.

[Chemical formula 30]

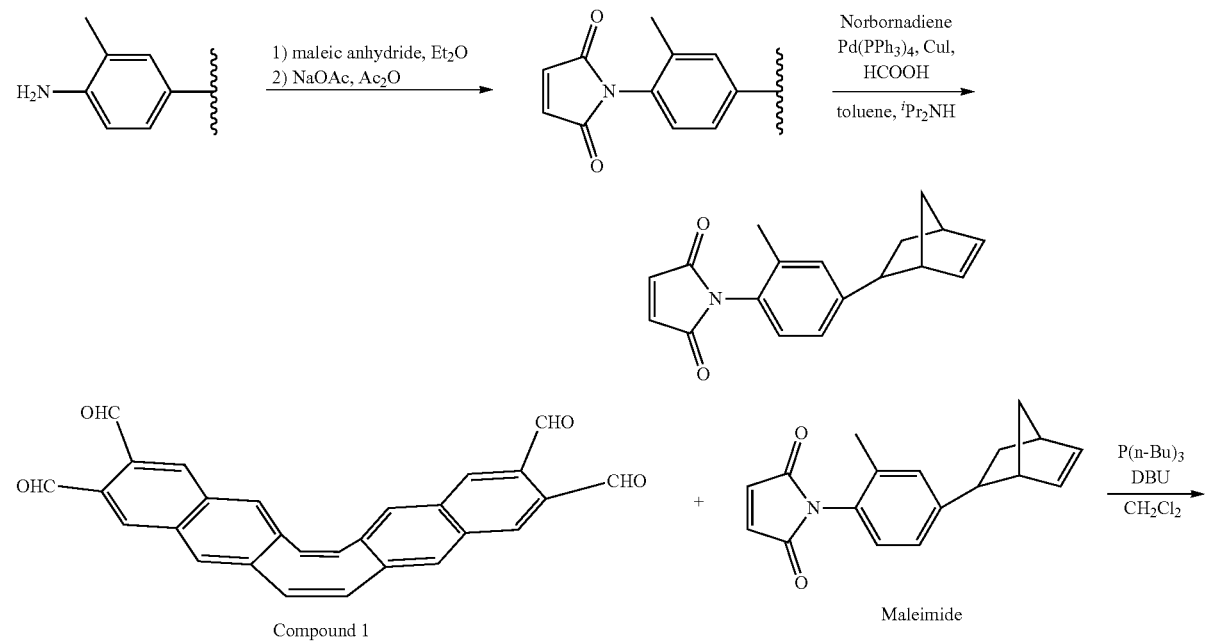

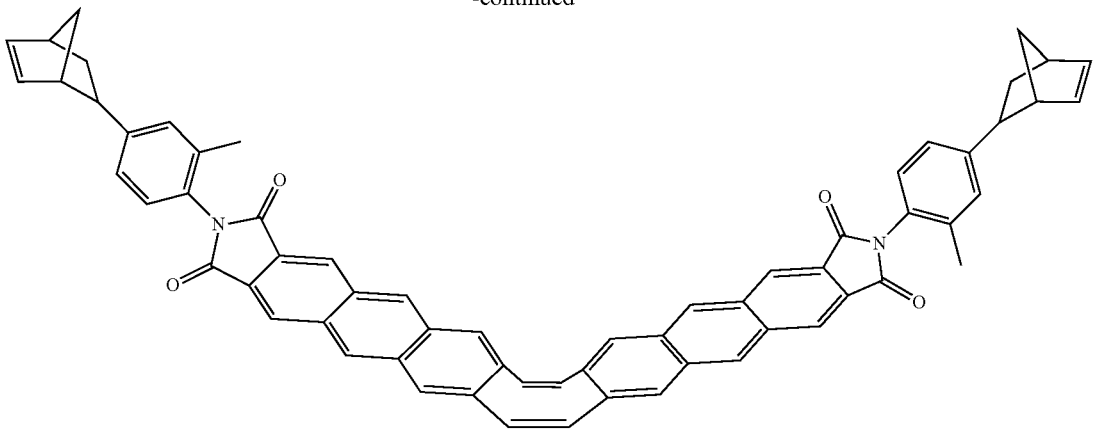

Compound A1

First, N-(4-(2,5-bicyclo[2.2.1]heptenyl)-2-methylphenyl)maleimide was synthesized in two stages. 4-Iodo-2-methylaniline (5.33 g, 22.9 mmol) was dissolved in diethyl ether (20 mL), and slowly added dropwise at 0° C. to a diethyl ether solution (20 mL) of maleic anhydride (1.87 g, 19.1 mmol) in a nitrogen atmosphere. After stirring for two hours thereafter at room temperature, the precipitated solid was filtered out and washed with diethyl ether. The solid filtered out and sodium acetate (302 mg) were dissolved in acetic anhydride (30 mL) and stirred for three hours at 140° C. The solvent was distilled off under reduced pressure, water was added, and the solution was extracted by methylene chloride. The organic layer was dried using anhydrous magnesium sulfate, and the solvent was distilled off under reduced pressure. The residue was purified by silica gel column chromatography using chloroform-hexane mixed solvent (mixture ratio 1:1) as the developing solvent, and N-(4-iodo-2-methylphenyl)maleimide (4.20 g, 13.4 mmol, 74%) was obtained as a white solid. The spectral data of N-(4-iodo-2-methylphenyl)maleimide were as follows.

$^1$H NMR (400 MHz, CDCl$_3$): δ 7.70 (s, 1H), 7.62 (d, J=8.4 Hz, 1H), 6.87 (s, 1H), 6.84 (d, J=8.4 Hz, 1H), 2.11 (s, 3H); $^{13}$C NMR (100 MHz, CDCl$_3$): δ 169.0, 140.0, 138.8, 136.0, 134.4, 130.3, 129.8, 95.1, 17.6; HRMS (APCI, positive): [M$^+$] calcd. for C$_{11}$H$_8$INO$_2$, 312.9600; found 312.9606.

N-(4-iodo-2-methylphenyl)maleimide (2.50 g, 7.98 mmol), tetrakis(triphenylphosphine)palladium (185 mg, 0.160 mmol), copper iodide (61.0 mg, 0.320 mmol), and formic acid (1.20 mL) were dissolved in toluene (30 mL) and diisopropylamine (10 mL) and heated for six hours at 80° C. in a nitrogen atmosphere. After allowing it to cool room temperature, water was added, and the solution was extracted by methylene chloride. The organic layer was dried using anhydrous magnesium sulfate, and the solvent was distilled off under reduced pressure. A crude product was obtained by separating the residue by silica gel column chromatography using chloroform-hexane mixed solvent (mixture ratio 1:1) as the developing solvent. N-(4-(2,5-bicyclo[2.2.1]heptenyl)-2-methylphenyl)maleimide (379 mg, 1.36 mmol, 17%) was obtained by further separation by size exclusion column chromatography using chloroform as the developing solvent. The spectral data of N-(4-(2,5-bicyclo[2.2.1]heptenyl)-2-methylphenyl)maleimide were as follows.

$^1$H NMR (400 MHz, CDCl$_3$): δ 7.22 (s, 1H), 7.20 (d, J=8.0 Hz, 1H), 7.02 (d, J=8.0 Hz, 1H), 6.85 (s, 2H), 6.26-6.24 (m, 1H), 6.18-6.16 (m, 1H), 2.97-2.92 (m, 2H), 2.72-2.69 (m, 1H), 2.14 (s, 3H), 1.76-1.71 (m, 1H), 1.66-1.56 (m, 2H), 1.45-1.43 (m, 1H); $^{13}$C NMR (100 MHz, CDCl$_3$): δ 170.0, 147.5, 137.4, 137.1, 135.9, 134.3, 130.4, 128.3, 127.2, 126.0, 48.0, 45.7, 43.4, 42.2, 33.6, 17.9; HRMS (APCI, positive): [M$^+$] calcd. for C$_{11}$H$_{17}$NO$_2$, 279.1259; found 279.1266.

Next, tributylphosphine (320 μL, 1.28 mmol) was added dropwise at 0° C. to a methylene chloride solution (10 mL) of N-(4-(2,5-bicyclo[2.2.1]heptenyl)-2-methylphenyl)maleimide (336 mg, 1.20 mmol) in a nitrogen atmosphere, and the reaction solution was stirred for 20 minutes at room temperature. The reaction solution was then slowly added dropwise at 0° C. to a methylene chloride solution (160 mL) of compound 1 (208 mg, 0.500 mmol) (see [Chemical formula 30] above) in a nitrogen atmosphere, and diazabicycloundecene (5.0 μL, 34 μmol) was added. After stirring for 15 hours at room temperature, water was added, and the reaction was stopped, and the solution was extracted by methylene chloride. The organic layer was dried using anhydrous magnesium sulfate, and the solvent was distilled off under reduced pressure. The residue was purified by silica gel column chromatography using methylene-chloride-hexane mixed solvent (mixture ratio 9:1) as the developing solvent, and compound A1 (104 mg, 0.115 mmol, 23%) (see [Chemical formula 30] above) was obtained as a yellow solid by washing the solid remaining after distilling off the solvent under reduced pressure by acetone. The spectral data of compound A1 were as follows.

$^1$H NMR (400 MHz, CDCl$_3$): δ 8.54 (s, 8H), 7.92 (s, 4H), 7.26 (s, 2H), 7.24 (d, J=8.0 Hz, 2H), 7.13 (d, J=8.0 Hz, 2H), 6.27-6.24 (m, 2H), 6.19-6.16 (m, 2H), 2.99-2.95 (m, 4H), 2.75-2.70 (m, 2H), 2.20 (s, 6H), 1.81-1.43 (m, 8H); HRMS (APCI, positive): [M$^+$] calcd. for C$_{64}$H$_{46}$N$_2$O$_6$, 906.3458; found 906.3461.

Comparative Example 1

A n-conjugated compound (compound A2) of anthraceneimide dimer and norbornene crosslinked by methylene groups was synthesized by the procedure described below.

[Chemical formula 31]

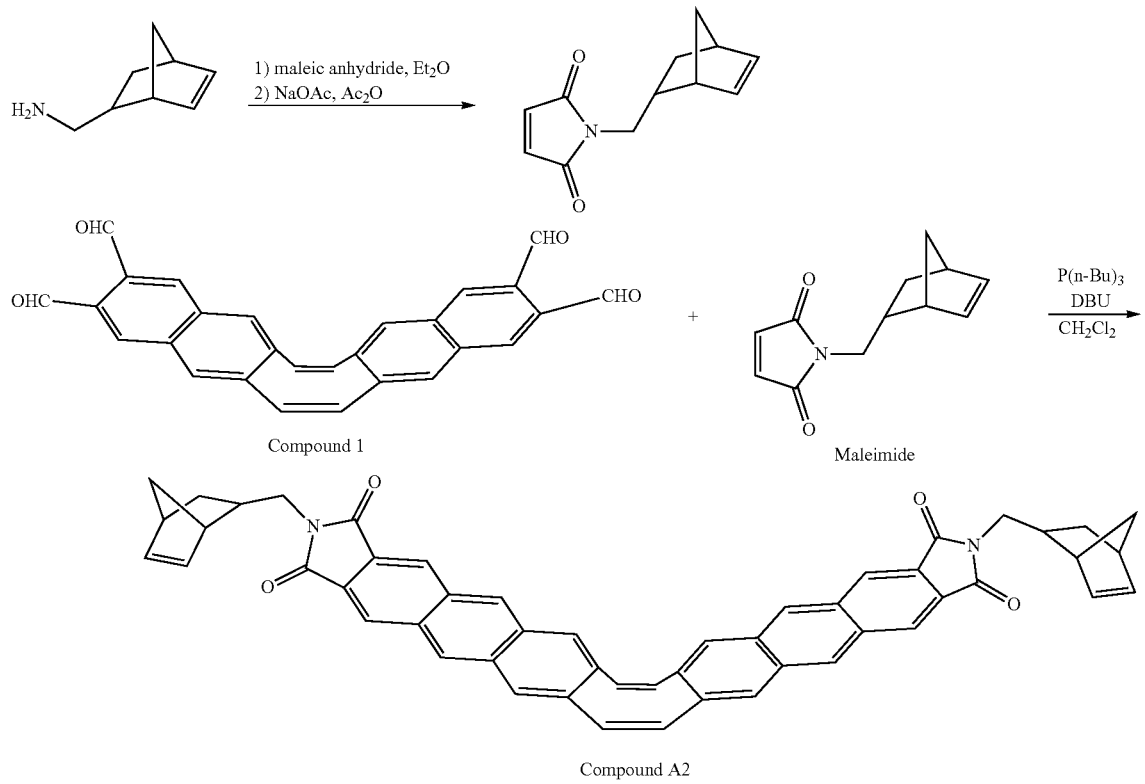

Compound 1

Maleimide

Compound A2

First, N-((2,5-bicyclo[2.2.1]heptenyl)methyl) maleimide was synthesized. 2,5-Bicyclo[2.2.1]heptenylmethaneamine (5.10 g, 41.4 mmol) was dissolved in diethyl ether (50 mL), and slowly added dropwise at 0° C. to a diethyl ether solution (50 mL) of maleic anhydride (3.62 g, 36.9 mmol). The reaction solution was stirred for two hours at room temperature, and the solid that precipitated was filtered out and washed several times with diethyl ether. The solid filtered out and sodium acetate (800 mg) were dissolved in acetic anhydride (80 mL), and stirred for four hours at 140° C. The solvent was distilled off under reduced pressure, water was added, and the solution was extracted by methylene chloride. The organic layer was dried using anhydrous magnesium sulfate, and the solvent was distilled off under reduced pressure. The residue was purified by silica gel column chromatography using chloroform-hexane mixed solvent (mixture ratio 3:2) as the developing solvent, and N-((2,5-bicyclo[2.2.1]heptenyl)methyl)maleimide (6.60 g, 32.5 mmol, 88%) was obtained as a white solid. The spectral data of N-((2,5-bicyclo[2.2.1]heptenyl)methyl)maleimide were as follows.

$^1$H NMR (400 MHz, CDCl$_3$): δ 6.68 (s, 2H), 6.23-6.21 (m, 1H), 6.10-6.07 (m, 1H), 3.30-3.17 (m, 2H), 2.80 (s, 1H), 2.66 (s, 1H), 2.46-2.40 (m, 1H), 1.86-1.80 (m, 1H), 1.57 (s, 1H), 1.43-1.40 (m, 1H), 1.20 (d, J=7.6 Hz, 1H), 0.62-0.58 (m, 1H); $^{13}$C NMR (100 MHz, CDCl$_3$): δ 170.7, 137.5, 133.8, 132.4, 49.3, 44.0, 42.3, 41.6, 37.9, 28.9; HRMS (APCI, positive): [M$^+$] calcd. for C$_{12}$H$_{13}$NO$_2$, 203.0946; found 203.0953.

Next, tributylphosphine (160 μL, 0.641 mmol) was added dropwise at 0° C. to a methylene chloride solution (8 mL) of N-((2,5-bicyclo[2.2.1]heptenyl)methyl)maleimide (122 mg, 0.600 mmol) in a nitrogen atmosphere, and the reaction solution was stirred for 20 minutes at room temperature. The reaction solution was then slowly added dropwise at 0° C. to a methylene chloride solution (120 mL) of compound 1 (104 mg, 0.250 mmol) (see [Chemical formula 31] above) in a nitrogen atmosphere, and diazabicycloundecene (4.0 μL, 27 μmol) was added. After stirring for 10 hours at room temperature, water was added, and the reaction was stopped, and the solution was extracted by methylene chloride. The organic layer was dried using anhydrous magnesium sulfate, and the solvent was distilled off under reduced pressure. The residue was purified by silica gel column chromatography using methylene chloride as the developing solvent, and compound A2 (39.6 mg, 52.5 μmol, 21%) (see [Chemical formula 31] above) was obtained as a yellow solid. Furthermore, since the solubility in the deuterated chloroform solvent was low and adequate signal intensity could not be obtained in $^1$H-NMR measurement of compound A2, measurement was conducted at room temperature after dissolution by heating in a deuterated tetrachloroethane solvent. The spectral data of compound A2 were as follows.

$^1$H NMR (400 MHz, 1,1,2,2-tetrachloroethane-d$_2$): δ 8.49 (s, 4H), 8.39 (s, 4H), 7.90 (s, 4H), 7.20 (s, 4H), 6.26-6.24 (m, 2H), 6.18-6.16 (m, 2H), 3.49-3.36 (m, 4H), 2.80 (s, 2H), 2.72 (s, 2H), 2.56-2.54 (m, 2H), 1.88-1.85 (m, 2H), 1.40-1.19 (m, 4H), 0.69-0.66 (m, 2H); HRMS (APCI, positive): [M$^+$] calcd. for C$_{52}$H$_{38}$N$_2$O$_4$, 754.2832; found 754.2843.

Figure 2:
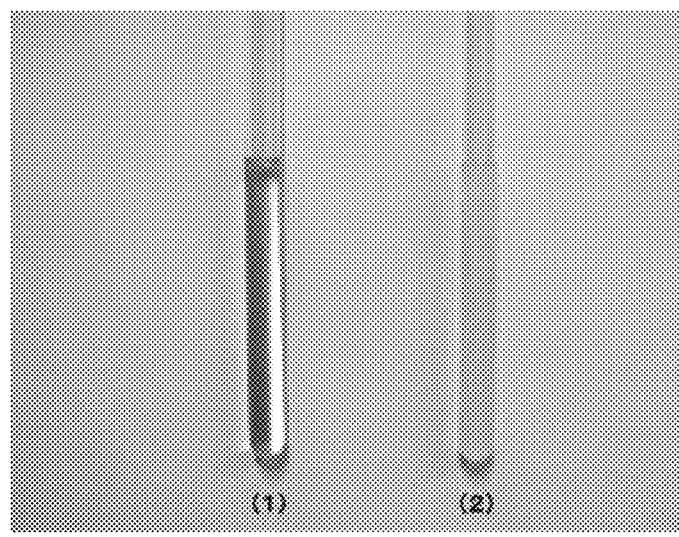
FIG. 2 is a photograph substituted for a drawing.

FIG. 2(1) is a photograph of compound A1 (1 μmol) synthesized in Example 1 dissolved in chloroform (0.6 mL). FIG. 2(2) is a photograph of when compound A2 synthesized in Comparative Example 1 was added to chloroform under the same conditions as compound A1. As is evident from FIGS. 2(1) and (2), compound A1 synthesized in Example 1 exhibited good solubility in the organic solvent, and it was confirmed that film synthesis by the polymerization reaction described later can be carried out without problem. On the other hand, compound A2 synthesized in Comparative Example 1 had low solubility in the organic solvent. It became a suspension, as shown in FIG. 2(2), and film synthesis by polymerization reaction was difficult.

Example 2

A n-conjugated compound (compound A3) of naphthaleneimide dimer and norbornene crosslinked at the 1-position and 4-position of the naphthalene ring was synthesized by the procedure described below.

[Chemical formula 32]

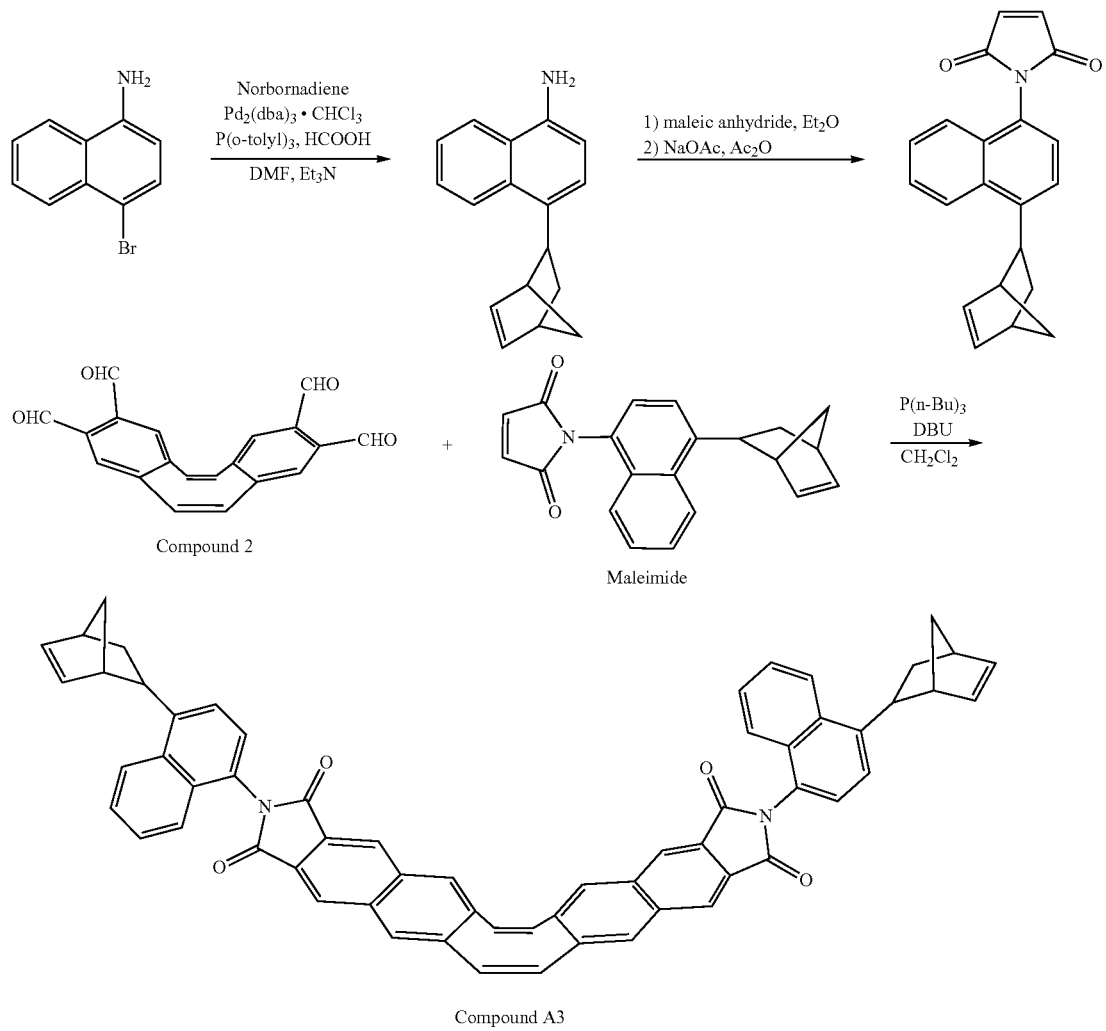

Compound A3

First, N-(4-(2,5-bicyclo[2.2.1]heptenyl)-1-naphthyl)maleimide was synthesized in two stages.

4-Bromo-1-naphthylamine (4.22 g, 19.1 mmol), tris (dibenzylideneacetone)dipalladium-chloroform complex (198 mg, 0.191 mmol), tris(o-tolyl)phosphine (232 mg, 0.762 mmol), and formic acid (2.90 mL, 76.9 mmol) were dissolved in dimethylformamide (24 mL) and triethylamine (6 mL), and heated for five hours at 60° C. in a nitrogen atmosphere. After allowing to cool to room temperature, water was added, and the solution was extracted by methylene chloride. The organic layer was dried using anhydrous magnesium sulfate, and the solvent was distilled off under reduced pressure. 4-(2,5-Bicyclo[2.2.1]heptenyl)-1-naphthylamine (2.96 g, 12.6 mmol, 66%) was obtained as a colorless oil by separating the residue by silica gel column chromatography using chloroform-hexane mixed solvent (mixture ratio 4:1) as the developing solvent. The spectral data of 4-(2,5-bicyclo[2.2.1]heptenyl)-1-naphthylamine were as follows.

$^1$H NMR (400 MHz, CDCl$_3$): δ 8.12-8.03 (m, 2H), 7.53-7.48 (m, 2H), 6.86-6.80 (m, 2H), 6.38-6.36 (m, 1H), 6.31-6.30 (m, 1H), 4.01 (s, 2H), 2.97-2.92 (m, 2H), 2.72-2.69 (m, 1H), 1.76-1.71 (m, 1H), 1.66-1.56 (m, 2H), 1.45-1.43 (m, 1H); $^{13}$C NMR (100 MHz, CDCl$_3$): δ 141.9, 139.2, 135.9, 133.2, 131.3, 125.8, 125.5, 124.5, 124.3, 124.4, 124.3, 121.3, 111.4, 53.3, 50.6, 42.8, 33.9, 32.0; HRMS (APCI, positive): [M$^+$] calcd. for C$_{17}$H$_{17}$N, 235.1361; found 235.1372.

4-(2,5-Bicyclo[2.2.1]heptenyl)-1-naphthylamine (3.96 g, 16.8 mmol) was dissolved in diethyl ether (30 mL), and slowly added dropwise at 0° C. to a diethyl ether solution (50 mL) of maleic anhydride (1.10 g, 11.2 mmol). The reaction solution was stirred for two hours at room temperature, and the solid that precipitated was filtered out and washed several times with diethyl ether. The solid filtered out and sodium acetate (602 mg) were dissolved in acetic anhydride (60 mL), and stirred for three hours at 140° C. The solvent was distilled off under reduced pressure, water was added, and the solution was extracted by methylene chloride. The organic layer was dried using anhydrous magnesium sulfate, and the solvent was distilled off under reduced pressure. The residue was purified by silica gel column chromatography using chloroform-hexane mixed solvent (mixture ratio 3:2) as the developing solvent, and N-(4-(2, 5-bicyclo[2.2.1]heptenyl)-1-naphthyl)maleimide (2.80 g, 8.88 mmol, 79%) was obtained as a white solid. The spectral data of N-(4-(2,5-bicyclo[2.2.1]heptenyl)-1-naphthyl)maleimide were as follows.

$^1$H NMR (400 MHz, CDCl$_3$): δ 8.21-8.11 (m, 1H), 7.60-7.46 (m, 4H), 7.33-7.27 (m, 1H), 6.96 (s, 2H), 6.38-6.36 (m, 1H), 6.31-6.30 (m, 1H), 3.50-3.03 (m, 2H), 2.60-1.10 (m, 5H) (mixture of isomers); 13C NMR (100 MHz, CDCl$_3$): δ 176.53, 176.50, 144.53, 144.49, 140.02, 139.99, 137.8, 136.6, 133.2, 132.7, 129.1, 128.9, 127.0, 126.5, 126.2, 126.0, 125.9, 125.8, 125.5, 125.3, 124.7, 124.2, 123.7, 122.2, 121.3, 46.2, 46.1, 45.9, 42.2, 39.6, 34.8, 34.6, 29.0, 28.3, 13.7, 11.0, 10.3 (mixture of isomers); HRMS (APCI, positive): [M$^+$] calcd. for C$_{21}$H$_{17}$NO$_2$, 315.1259; found 315.1266.

Next, tributylphosphine (130 μL, 0.520 mmol) was added dropwise at 0° C. to a methylene chloride solution (10 mL) of N-((2,5-bicyclo[2.2.1]heptenyl)methyl)maleimide (153 mg, 0.485 mmol) in a nitrogen atmosphere, and the reaction solution was stirred for 20 minutes at room temperature. The reaction solution was then slowly added dropwise at 0° C. to a methylene chloride solution (50 mL) of compound 2 (63.2 mg, 0.200 mmol) (see [Chemical formula 32] above) in a nitrogen atmosphere, and diazabicycloundecene (5.0 μL, 34 μmol) was added. After stirring for 14 hours at room temperature, water was added, and the reaction was stopped, and the solution was extracted by methylene chloride. The organic layer was dried using anhydrous magnesium sulfate, and the solvent was distilled off under reduced pressure. Compound A3 (31.6 mg, 35.9 μmol, 18%) (see [Chemical formula 32] above) was obtained as a yellow solid by purifying the residue by silica gel column chromatography using chloroform-hexane mixed solvent (mixture ratio 4:1) as the developing solvent. Compound A3 exhibited good solubility in organic solvents such as chloroform, and it was confirmed that film production by a polymerization reaction could be performed without a problem. The spectral data of compound A3 were as follows.

$^1$H NMR (400 MHz, CDCl$_3$): δ 7.38 (s, 4H), 8.22-8.12 (m, 2H), 7.90 (s, 4H), 7.64-7.39 (m, 10H), 7.20 (s, 4H), 6.39-6.37 (m, 2H), 6.32-6.29 (m, 2H), 3.51-3.04 (m, 4H), 2.42-1.24 (m, 10H); HRMS (APCI, positive): [M$^+$] calcd. for C$_{62}$H$_{42}$N$_2$O$_4$, 878.3145; found 878.3152.

Example 3

A n-conjugated compound (compound A4) of naphthaleneimide dimer and norbornene crosslinked by (l-phenyl)ethyl groups was synthesized by the procedure described below.

[Chemical formula 33]

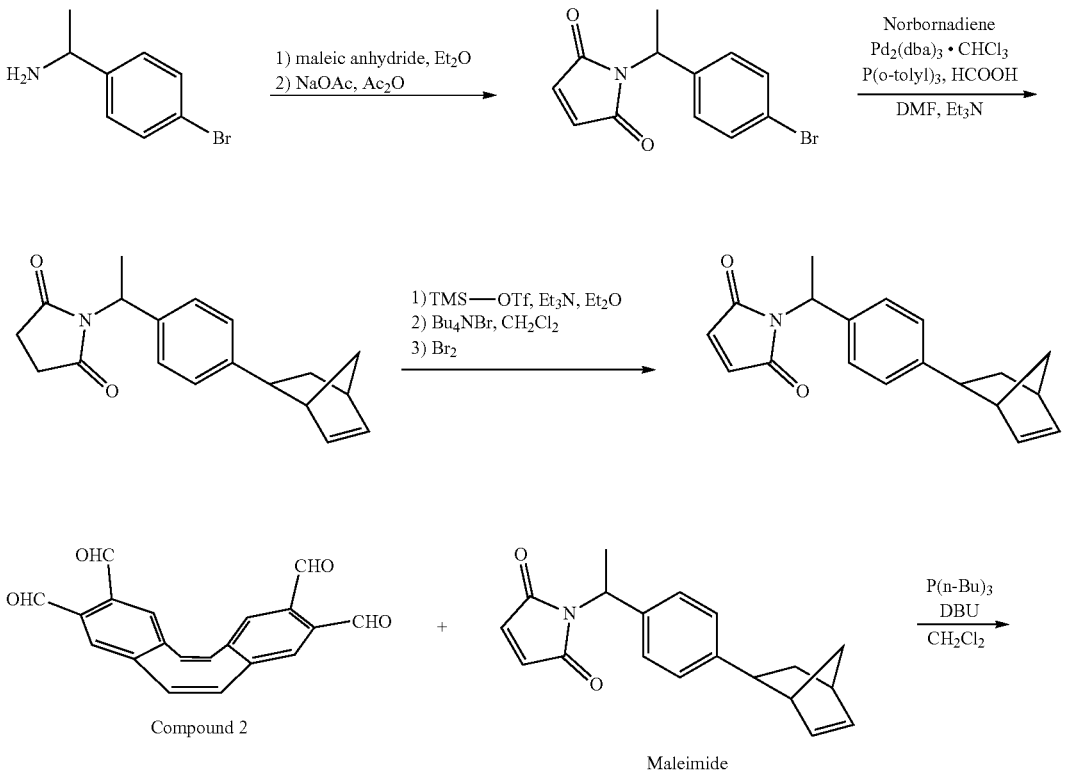

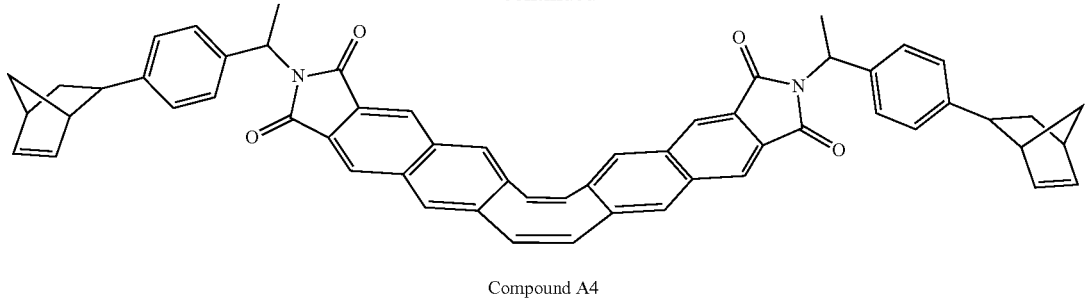

Compound A4

First, N-(1-(4-(2,5-bicyclo[2.2.1]heptenyl) phenyl)ethyl) maleimide was synthesized in three stages.

1-(4-Bromophenyl)ethylamine (25.1 g, 0.125 mol) was dissolved in diethyl ether (100 mL), and slowly added dropwise at 0° C. to a diethyl ether solution (200 mL) of maleic anhydride (10.4 g, 0.106 mol). The reaction solution was stirred for two hours at room temperature, and the solid that precipitated was filtered out and washed several times by diethyl ether. The solid filtered out and sodium acetate (1.20 g) were dissolved in acetic anhydride (120 mL), and stirred for four hours at 140° C. The solvent was distilled off under reduced pressure, water was added, and the solution was extracted by methylene chloride. The organic layer was dried using anhydrous magnesium sulfate, and the solvent was distilled off under reduced pressure. The residue was purified by silica gel column chromatography using chloroform-hexane mixed solvent (mixture ratio 4:1) as the developing solvent, and N-(1-(4-bromophenyl)ethyl)maleimide (23.5 g, 84.0 mmol, 79%) was obtained as a white solid. The spectra data of N-(1-(4-bromophenyl)ethyl)maleimide were as follows.

$^1$H NMR (400 MHz, CDCl$_3$): δ 7.46-7.43 (m, 2H), 7.31-7.28 (m, 2H), 6.64 (s, 2H), 5.30 (q, J=7.6 Hz, 1H), 1.79 (d, J=7.6 Hz, 3H); 13C NMR (100 MHz, CDCl$_3$): δ 170.3, 139.1, 140.0, 131.5, 129.0, 121.6, 48.9, 17.4; HRMS (APCI, positive): [M$^+$] calcd. for C$_{12}$H$_{10}$BrNO$_2$, 278.9895; found 278.9904.

N-(1-(4-bromophenyl)ethyl)maleimide (5.60 g, 20.0 mmol), tris(dibenzylideneacetone)dipalladium-chloroform complex (205 mg, 0.198 mmol), tris(o-tolyl)phosphine (243 mg, 0.798 mmol), and formic acid (3.00 mL, 79.5 mmol) were dissolved in dimethylformamide (40 mL) and triethylamine (10 mL), and heated for five hours at 60° C. in a nitrogen atmosphere. After allowing to cool to room temperature, water was added, and the solution was extracted by methylene chloride. The organic layer was dried using anhydrous magnesium sulfate, and the solvent was distilled off under reduced pressure. N-(1-(4-(2,5-bicyclo[2.2.1]heptenyl) phenyl)ethyl)-2,5-pyrrolidinedione (3.71 g, 12.4 mmol, 63%) was obtained as a white solid by purifying the residue by silica gel column chromatography using chloroform-hexane mixed solvent (mixture ratio 4:1) as the developing solvent. The spectral data of N-(1-(4-(2,5-bicyclo[2.2.1]heptenyl) phenyl)ethyl)-2,5-pyrrolidinedione were as follows.

$^1$H NMR (400 MHz, CDCl$_3$): δ 7.39-7.36 (m, 2H), 7.23-7.21 (m, 2H), 6.24-6.22 (m, 1H), 6.16-6.14 (m, 1H), 5.40 (q, J=7.2 Hz, 1H), 2.95-2.87 (m, 2H), 2.66-2.63 (m, 1H), 2.63 (s, 2H), 1.80 (d, J=7.2 Hz, 3H), 1.80-1.40 (m, 4H); $^{13}$C NMR (100 MHz, CDCl$_3$): δ 176.9, 145.6, 137.2, 137.1, 136.8, 127.5, 127.4, 50.0, 48.1, 45.6, 43.3, 42.2, 33.5, 28.0, 16.5; HRMS (APCI, positive): [M$^+$] calcd. for C$_{19}$H$_{21}$NO$_2$, 295.1572; found 295.1580.

N-(1-(4-(2,5-bicyclo[2.2.1]heptenyl)phenyl)ethyl)-2,5-pyrrolidinedione (3.40 g, 11.5 mmol) and triethylamine (3.40 mL, 24.4 mmol) were dissolved in diethyl ether (60 mL), and trimethylsilyl trifluoromethanesulfonate (4.40 mL, 24.3 mmol) was slowly added dropwise at 0° C. After stirring for two hours at room temperature, the solution was again cooled to 0° C., and tributylammonium bromide (37.2 mg, 0.115 mmol) and methylene chloride (60 mL) were added. After stirring for five minutes at 0° C., bromine (620 µL, 12.0 mmol) was added, and stirred for 20 minutes at 0° C. The solvent was distilled off under reduced pressure, diethyl ether was added to the residue, and the undissolved residue was removed. The solvent was distilled off under reduced pressure, and N-(1-(4-(2,5-bicyclo[2.2.1]heptenyl) phenyl)ethyl)maleimide (1.42 g, 4.84 mmol, 42%) was obtained as a colorless oil by purifying the residue by silica gel column chromatography using chloroform-hexane mixed solvent (mixture ratio 4:1) as the developing solvent. The spectral data of N-(1-(4-(2,5-bicyclo[2.2.1]heptenyl) phenyl)ethyl)maleimide were as follows.

$^1$H NMR (400 MHz, CDCl$_3$): δ 7.35-7.31 (m, 2H), 7.24-7.20 (m, 2H), 6.62 (s, 2H), 6.24-6.22 (m, 1H), 6.16-6.14 (m, 1H), 5.33 (q, J=7.2 Hz, 1H), 2.95 (s, 1H), 2.87 (s, 1H), 2.69-2.66 (m, 1H), 1.93-1.20 (m, 3H), 1.81 (d, J=7.2 Hz, 3H), 0.80-0.75 (m, 1H); $^{13}$C NMR (100 MHz, CDCl$_3$): δ 17.05, 142.5, 139.2, 137.1, 135.9, 135.8, 126.6, 125.0, 56.0, 52.9, 50.6, 35.6, 42.8, 31.6, 17.7; HRMS (APCI, positive): [M$^+$] calcd. for C$_{19}$H$_{19}$NO$_2$, 293.1416; found 293.1419.

Next, tributylphosphine (130 µL, 0.520 mmol) was added dropwise at 0° C. to a methylene chloride solution (10 mL) of N-(1-(4-(2,5-bicyclo[2.2.1]heptenyl)phenyl)ethyl)maleimide (143 mg, 0.487 mmol) in a nitrogen atmosphere, and the reaction solution was stirred for 20 minutes at room temperature. The reaction solution was then slowly added dropwise at 0° C. to a methylene chloride solution (50 mL) of compound 2 (63.2 mg, 0.200 mmol) (see [Chemical formula 33] above) in a nitrogen atmosphere, and diazabicycloundecene (6.0 µL, 40 µmol) was added. After stirring for 16 hours at room temperature, water was added, and the reaction was stopped, and the solution was extracted by methylene chloride. The organic layer was dried using anhydrous magnesium sulfate, and the solvent was distilled off under reduced pressure. Compound A4 (48.0 mg, 57.5 mmol, 29%) (see [Chemical formula 33] above) was obtained as a yellow solid by purifying the residue by silica gel column chromatography using methylene chloride as the developing solvent. Compound A4 exhibited good solubility in organic solvents such as chloroform, and it was confirmed that film production by a polymerization reaction could be performed without a problem. The spectral data of compound A4 were as follows.

$^1$H NMR (400 MHz, CDCl$_3$): δ 8.12 (s, 4H), 7.76 (s, 4H), 7.41-7.39 (m, 4H), 7.22-7.19 (m, 4H), 7.10 (s, 4H), 6.21-6.18 (m, 2H), 6.13-6.09 (m, 2H), 5.58 (q, J=7.2 Hz, 2H), 2.91-2.83 (m, 4H), 2.63-2.60 (m, 2H), 1.92 (d, J=7.2 Hz, 6H), 1.85-1.20 (m, 8H); HRMS (APCI, positive): [M$^+$] calcd. for C$_{58}$H$_{46}$N$_2$O$_4$, 834.3458; found 834.3463.

Synthesis of Mechanochromic Resin 1

Example 4

First, a dichloromethane solution of norbornene (manufactured by Aldrich Co.) represented by formula (21) below was prepared in a concentration of 200 g/L. A 2.0 g/L dichloromethane solution of the compound A1 synthesized in Example 1 above was also prepared.

Next, after mixing 100 μL of the dichloromethane solution of norbornene and 250 μL of the dichloromethane solution of compound A1, a dichloromethane solution (10 g/L) of a third generation Grubb's catalyst (manufactured by Aldrich Co.) represented by formula (22) below was added and stirred. After catalyst addition, the solution viscosity increased rapidly, and a gel-form solid was obtained. This is believed to be the result of polymerization of the norbornene by ring-opening metathesis polymerization to form polynorbornene as well as the incorporation of compound A1 as crosslinking points. The gel-form solid was dissolved in chloroform and, after removing the excess monomer by centrifugation, again dissolved in chloroform. A yellow solid was obtained by reprecipitation in methanol. A dried film was also obtained by casting the chloroform solution on a glass substrate and drying.

[Chemical formula 34]

(21)

[Chemical formula 35]

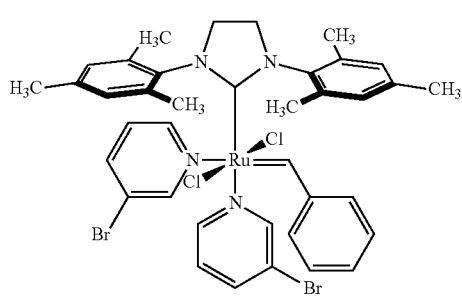

(22)

[S-S Curve]

Figure 3:
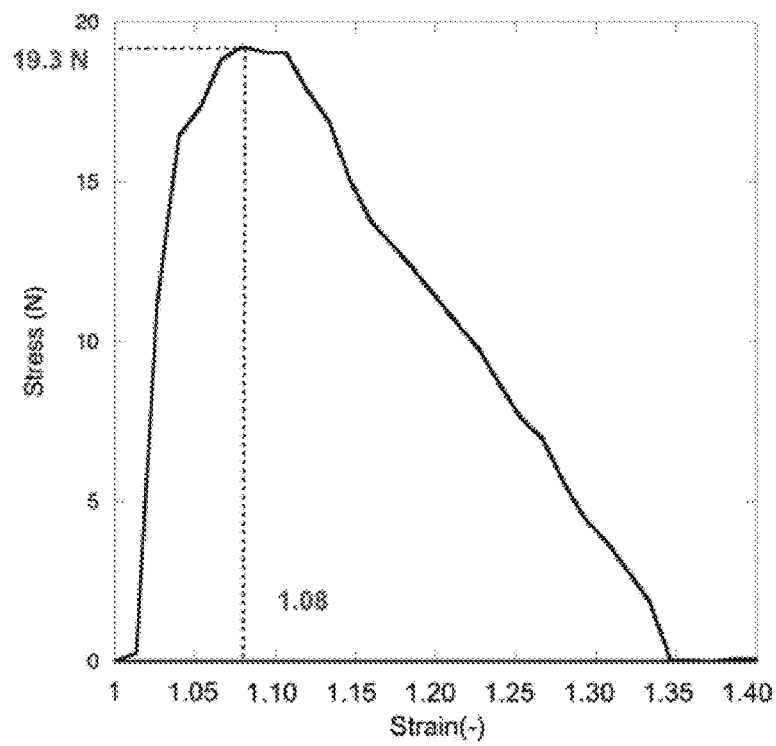
FIG. 3 shows a stress-strain (S-S) curve of a film (20 mm×10 mm) obtained in Example 4 measured using a tensile tester (DPU, Imada)

FIG. 3 shows the results obtained by measuring the stress-strain (S-S) curve of a film (20 mm×10 mm) obtained in Example 4 by a tensile tester (DPU, Imada). The film obtained in Example 4 exhibited a yield point, and the yield stress was about 19.3 N and the yield elongation about 1.1.

The stress decreased rapidly after yielding, and the film broke at an elongation of about 1.3. This suggested that the film obtained was a hard, glassy polymer.

[Fluorescence Spectrum]

Figure 4:
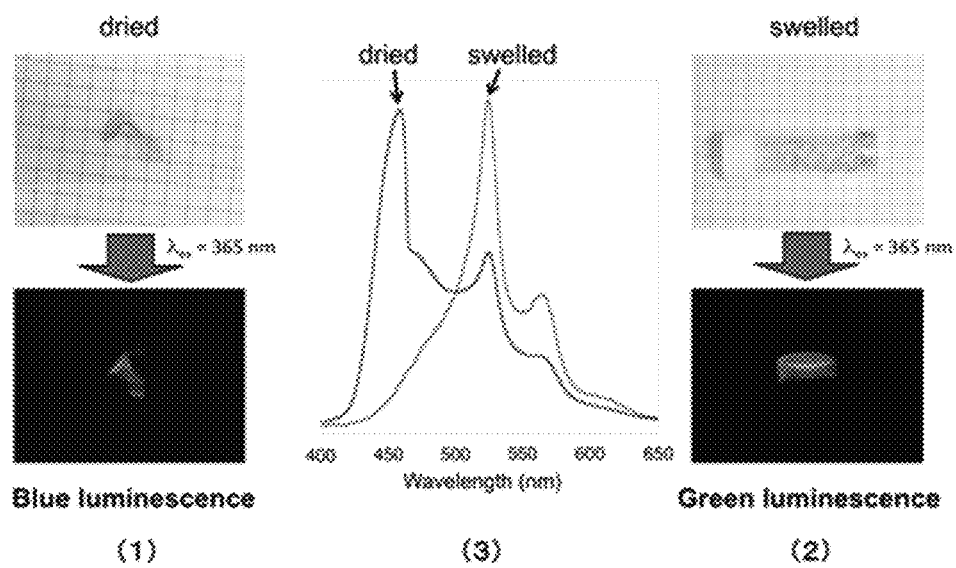
FIG. 4(1) is a photograph substituted for a drawing and is a photograph of a dry solid of a film synthesized in Example 4.

FIG. 4(1) is a photograph of a dry solid of a film synthesized in Example 4. FIG. 4(2) is a photograph of a gel-form solid of a film synthesized in Example 4 swollen by chloroform. FIG. 4(3) is a graph showing the emission spectra of each. Furthermore, the emission spectrum was measured at an excitation wavelength of 365 nm using an FP-650 manufactured by JASCO Corporation. While the gel-form solid of FIG. 4(2) exhibited green fluorescence upon ultraviolet excitation, the dry solid of FIG. 4(1) exhibited blue fluorescence. This is consistent with the fluorescence of an anthraceneimide dimer in solution and in a polymer solid, respectively. In addition, the fluorescence obtained is the fluorescence of the mechanochromic resin itself synthesized in Example 4 since the excess monomer not involved in resin synthesis was removed, as was mentioned above. Therefore, the mechanochromic resin synthesized in Example 4 was shown to have obtained polynorbornene with anthraceneimide dimer incorporated into the main chain.

[Mechanochromic Luminescence]

Figure 5:
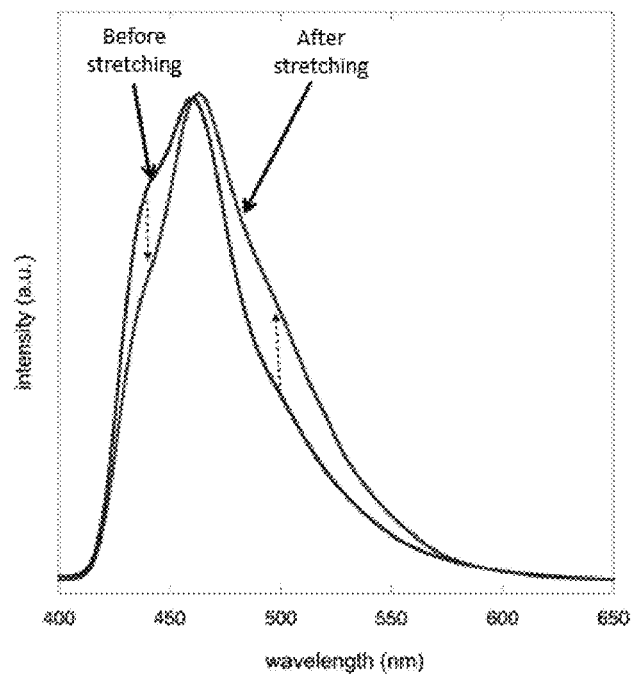
FIG. 5 shows the fluorescence spectrum of a film synthesized in Example 4 before and after stretching.

Both ends of the film synthesized in Example 4 were fixed to glass substrates by adhesive tape, and the film was stretched by moving the glass substrates apart. FIG. 5 shows the fluorescence spectra of the film before and after stretching. A red shift was evident in the spectrum after stretching. This proved that the film of the mechanochromic resin produced in Example 4 exhibits mechanochromic luminescence. It was also confirmed that the mechanochromic luminescence returns immediately to its original color when the force stretching the film is released and the film returns to its original state.

Synthesis of Mechanochromic Resin 2 and Comparative Example

Example 5

First, a dichloromethane solution of 5-acetyl-2-norbornene (manufactured by Aldrich Co.) represented by formula (23) below was prepared in a concentration of 625 mM. A dichloromethane solution of compound A1 synthesized in Example 1 was also prepared in a concentration of 0.25 mM, and a dichloromethane solution of a third generation Grubb's catalyst represented by formula (22) above was prepared in a concentration of 1.3 mM. A gel-form solid was obtained by mixing 4 mL of the dichloromethane solution of 5-acetyl-2-norbornene, 4 mL of the dichloromethane solution of compound A1, and 1 mL of the dichloromethane solution of the third generation Grubb's catalyst represented by formula (22). The solid obtained was dissolved in chloroform, and washed with a hexane/toluene (1:1) mixed solution. A film was obtained by casting the chloroform solution on a glass substrate.

[Chemical formula 36]

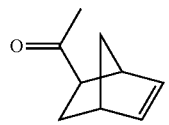

(23)

Comparative Example 2

Polymerization was conducted under the same conditions as in Example 5 except that the dichloromethane solution of compound A1 was removed, and a homopolymer of polyacetyl norbornene was also synthesized. The number-average molecular weight was 300,000 when the molecular weight of the homopolymer synthesized was measured by gel filtration chromatography (HLC-8230, Tosoh Corporation). Therefore, the mechanochromic resin synthesized in Example 5 is assumed to have a number-average molecular weight of 300,000 or higher given the length of the main chain.

[S-S Curve]

Figure 6:
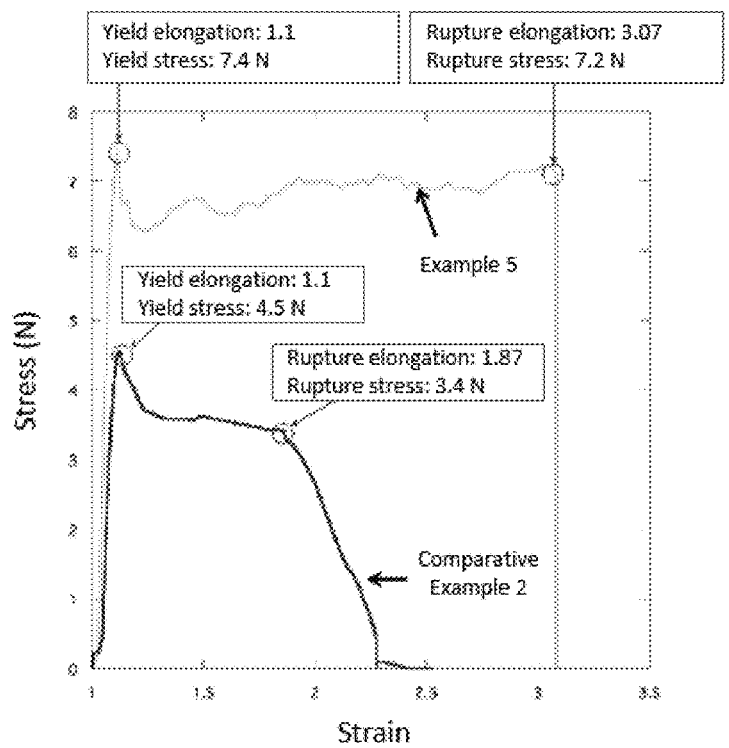
FIG. 6 shows the S-S curve of films (16 mm×10 mm) of Example 5 and Comparative Example 2.

The stress-strain (S-S) curves of the films obtained in Example 5 and Comparative Example 2 above were measured using a tensile tester (DPU, Imada). FIG. 6 shows the S-S curves of the films (16 mm×10 mm) of Example 5 and Comparative Example 2. The film of Comparative Example 2 had a yield stress of 4.5 N, yield elongation of 1.1, rupture stress of 3.4 N, and rupture elongation of 1.87. On the other hand, the film of Example 5 crosslinked by compound A1 had a similar yield elongation, but the yield stress rose to 7.4 N, and the rupture stress and elongation were 7.2 N and 3.07, respectively. This illustrates the characteristics of the crosslinked rubber well.

[Fluorescence Spectrum]

Figure 7:
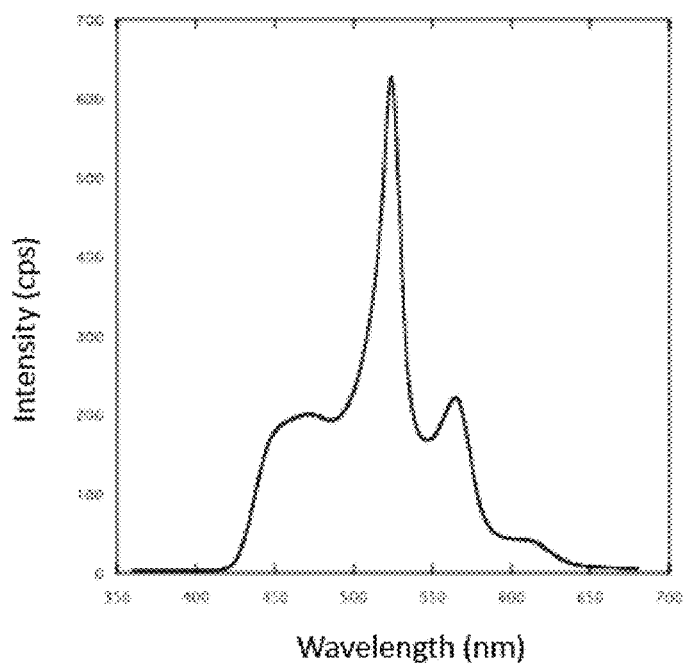
FIG. 7 shows the emission spectrum of a gel-form solid of a film synthesized in Example 5 swollen by chloroform.

FIG. 7 shows the emission spectrum of a gel-form solid of a film synthesized in Example 5 swollen by chloroform. The emission spectrum was measured at an excitation wavelength of 365 nm using an FP-650 manufactured by JASCO Corporation. The gel-form solid exhibited green fluorescence upon ultraviolet excitation. This is consistent of an anthraceneimide dimer in solution. This showed that polyacetyl norbornene with an anthraceneimide dimer incorporated into the main chain had been synthesized.

[Mechanochromic Luminescence]

Figure 8:
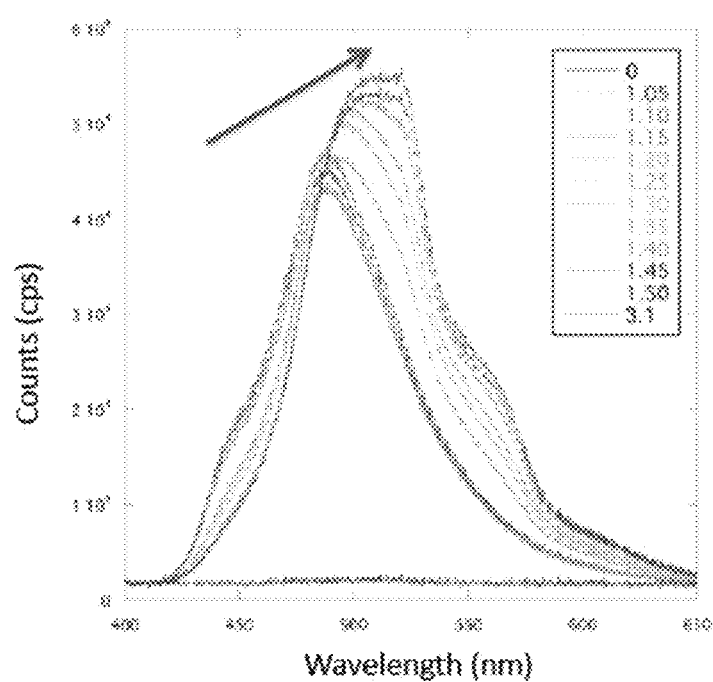
FIG. 8 shows the fluorescence spectrum in each elongation when a film synthesized in Example 5 was positioned in a tensile tester, irradiated with 365 nm excitation light, and the changes in fluorescence emission were measured using a probe-type fluorescence spectrophotometer (USB 4000, manufactured by Ocean Photonics)

The film synthesized in Example 5 was positioned in a tensile tester, irradiated with 365 nm excitation light, and the changes in fluorescence emission were measured by a probe-type fluorescence spectrophotometer (USB 4000, manufactured by Ocean Photonics). FIG. 8 shows the fluorescence spectrum in each elongation. As shown in FIG. 8, the fluorescence of the film was red-shifted as shown by the arrow beyond the yield point (1.1 in FIG. 8), and a change from blue to green was clearly observed. This proved that the film exhibits mechanochromic luminescence. It was also confirmed that the mechanochromic luminescence returns immediately to its original color when the force stretching the film is released and the film returns to its original state.

[Repeated Study]

Figure 9:
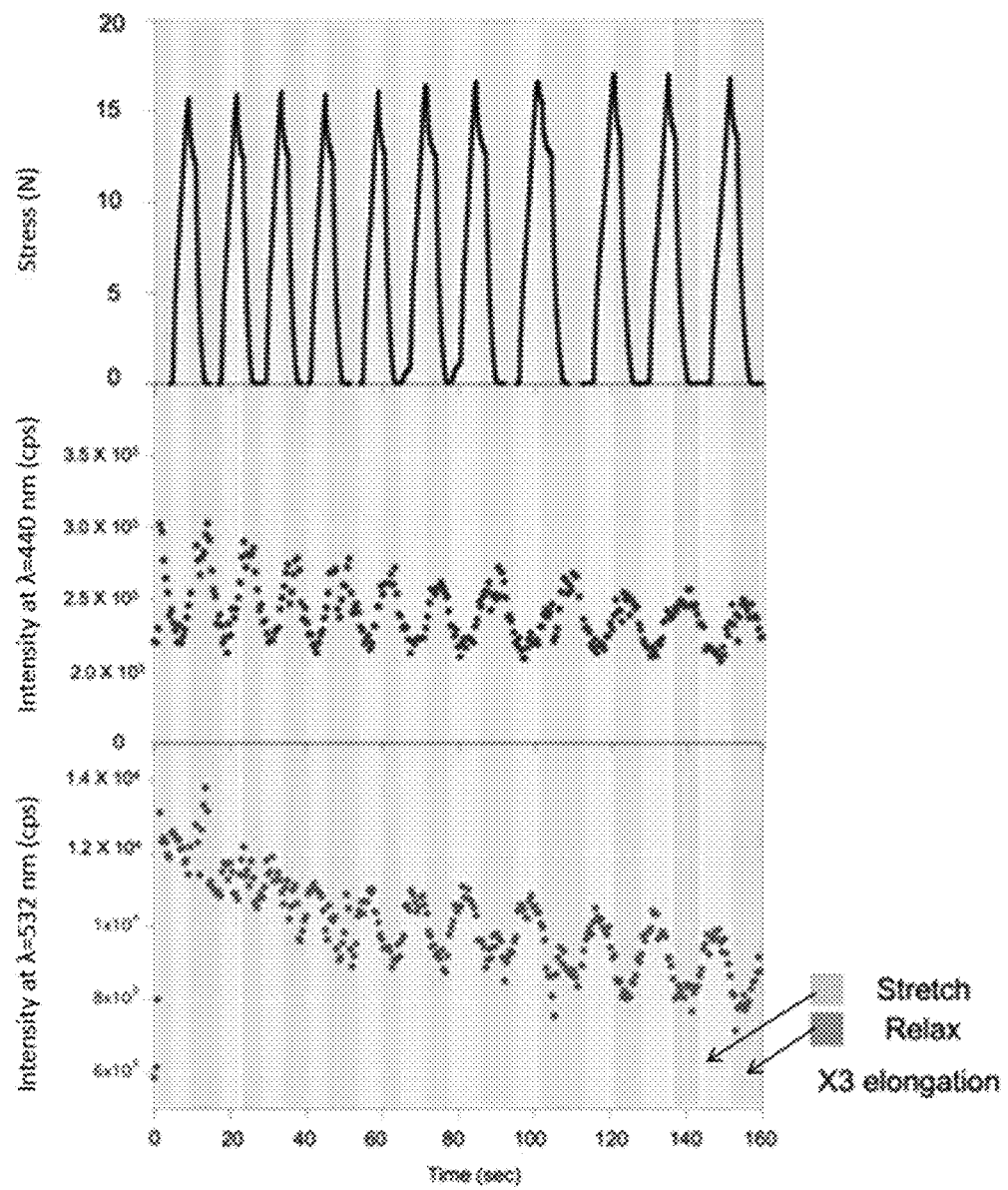
FIG. 9 is a graph plotting the film stress and changes in intensity at a fluorescence wavelength of 440 nm (blue) and 532 nm (green) when a film synthesized in Example 5 was repeatedly stretched and contracted.

The film synthesized in Example 5 was positioned in a tensile tester, irradiated by 365 nm excitation light, and the changes in fluorescence emission were measured by a probe-type fluorescence spectrophotometer (USB 4000, manufactured by Ocean Photonics). In this study, the film was stretched up to 3× by the tensile tester, returned to its original length after about five seconds, then again stretched 3×. FIG. 9 is a graph plotting the film stress and changes in intensity at a fluorescence wavelength of 440 nm (blue) and 532 nm (green) during the repeated study. As shown in FIG. 9, we are able to see that while the blue fluorescence intensity decreased and the green fluorescence intensified as the stress rose during stretching, the intensity of the green fluorescence decreased and the blue fluorescence intensified rapidly as the stress decreased during contraction. The above results confirmed that changes in fluorescence color occur rapidly in response to stress.

[Formation of Fibers]

Figure 10:
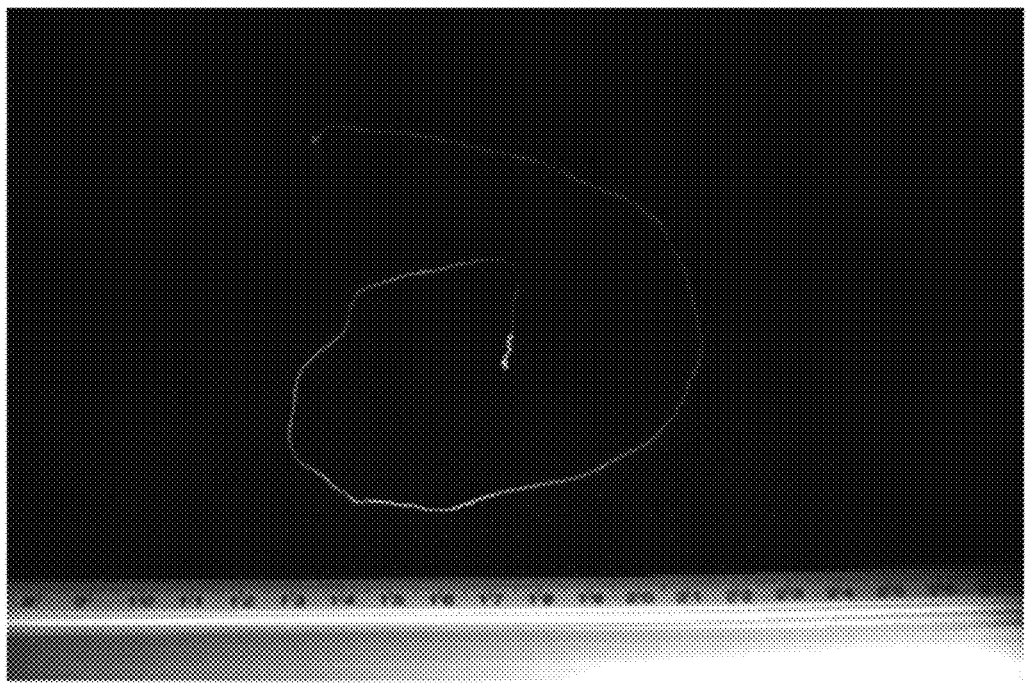
FIG. 10 is a photograph substituted for a drawing and is a fluorescent photograph of a fiber produced by a resin obtained in Example 5 when excited by an ultraviolet lamp (wavelength 365 nm).

Fibers about 200 m in diameter were obtained when the polymer obtained in Example 5 was dissolved in chloroform and slowly precipitated in methanol using a Pasteur pipette. FIG. 10 is a fluorescent photograph of a fiber produced by a resin obtained in Example 5 when excited by an ultraviolet lamp (wavelength 365 nm). We were able to confirm that the entire fiber shines blue, and the fluorescence color changes when the fiber is pulled.

Synthesis of Mechanochromic Resin 3

Example 6

Synthesis was conducted under the same conditions as in Example 5 except that the compound A4 synthesized in Example 3 was used instead of compound A1. A film could also be produced in Example 6, and the luminescence was confirmed to weaken when the film was stretched and to return immediately to a blue luminescent state when the film returned to its original state.

Comparative Example 3

Fifty-seven milligrams of Takeda Industries' stretchable polyurethane film was dissolved in 6.0 mL of tetrahydrofuran. After adding 0.3 mg of a compound of formula (24) below, the solution was poured into a dog bone-shaped Teflon (registered trademark) mold, and a resin film containing a mechanochromic luminescent material was obtained by drying naturally. Whether the film changed luminescent color while being stretched was observed thereafter, but no change in luminescent color could be seen from the initial state until the film ruptured. This showed that no change in luminescent color is obtained in response to stress when a resin is merely doped by a mechanochromic luminescent material and that stress can be visualized for the first time when the mechanochromic luminescent material is introduced into the polymer chain as crosslinking points via chemical bonds.

[Chemical formula 37]

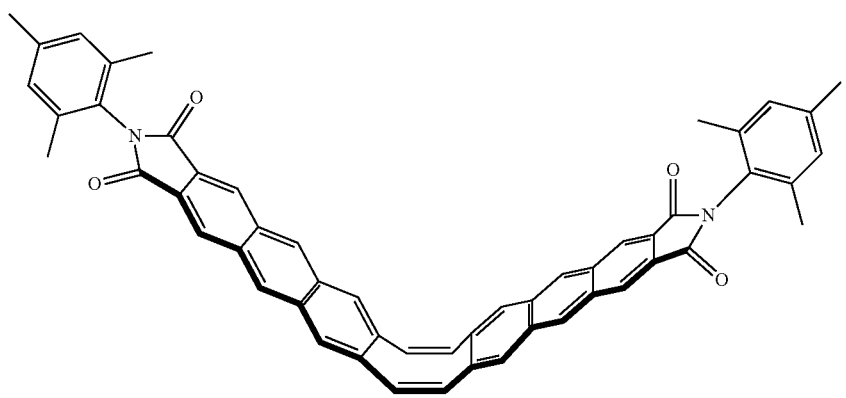

(24)

INDUSTRIAL APPLICABILITY

The mechanochromic resin of the present invention makes it possible to visualize the stress placed on a material in real time because its color changes rapidly due to stretching/contraction. Therefore, it can be expected to find application in coating materials, sports materials, and the like in addition to sensors such as damage sensor and pressure sensors.

What is claimed is:

1. A mechanochromic luminescent material represented by formula (1) or formula (2) below:

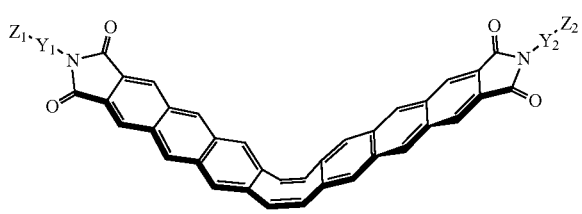

(1)

in the formula, $Y_1$ and $Y_2$ represent substituents that inhibit aggregation of a mechanochromic luminescent material represented by formula (1), and may be the same or different, $Z_1$ and $Z_2$ represent polymerizable groups, and may be the same or different,

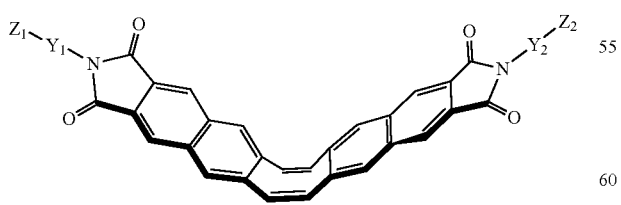

(2)

in the formula, $Y_1$ and $Y_2$ represent substituents that inhibit aggregation of a mechanochromic luminescent material represented by formula (2), and may be the same or different, $Z_1$ and $Z_2$ represent polymerizable groups, and may be the same or different, wherein $Y_1$ and $Y_2$ are selected from the following substituents: represented by Chemical formula 3

[Chemical formula 3]

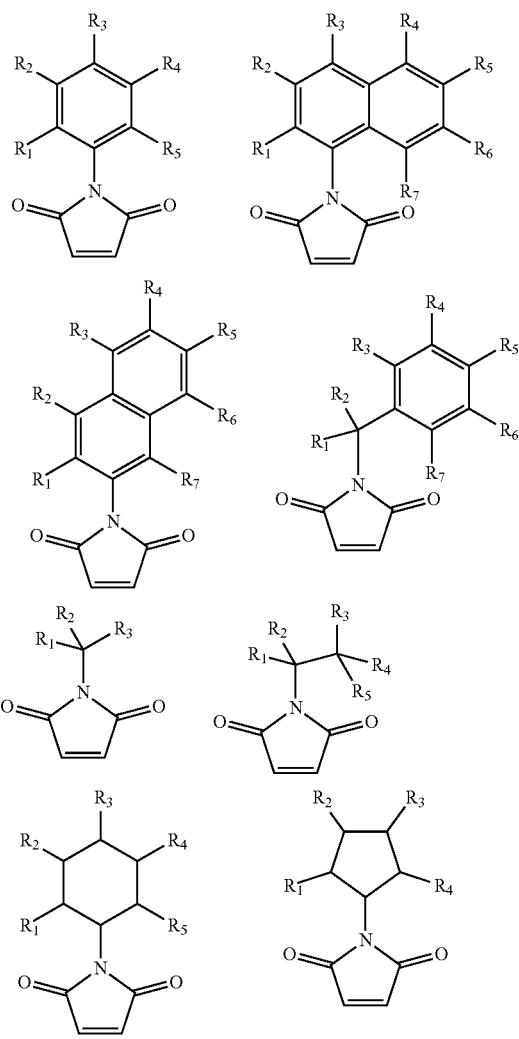

-continued

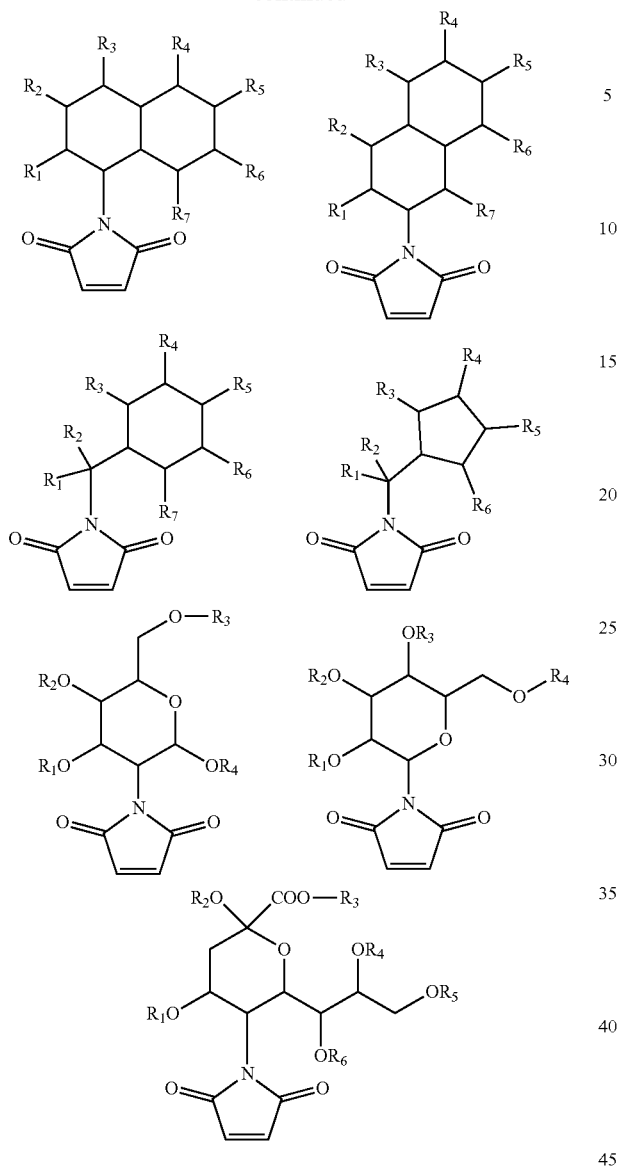

any one of the substituents $R_1$-$R_7$ represents a polymerizable group $Z_1$ or $Z_2$; $R_1$-$R_7$ other than the polymerizable group $Z_1$ or $Z_2$ represent H, a C1-20 linear, branched, or cyclic alkyl group, C6-20 aryl group, F, Cl, Br, I, $CF_3$, $CCl_3$, or $OCH_3$; and $R_1$-$R_7$ other than the polymerizable group $Z_1$ or $Z_2$ may be the same or different, wherein the polymerizable groups $Z_1$ and $Z_2$ are selected from the following substituents:

(3)

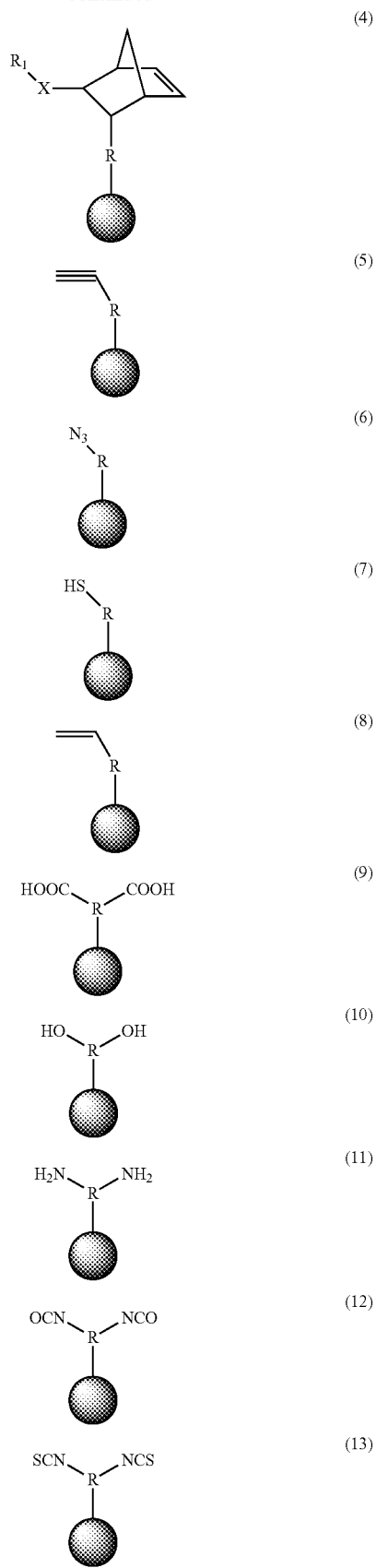

in the above formulas (3) and (4), X represents an amide or ester, but may be absent; in the above formulas (3) and (4), $R_1$ is the same as $R_1$ in [Chemical formula 3]; in the above formulas (3) to (13), R represents a C1-20 linear, branched, or cyclic alkylene group or a C6-20 arylene group, but R may be absent; and ● represents $Y_1$ or $Y_2$, and wherein when:

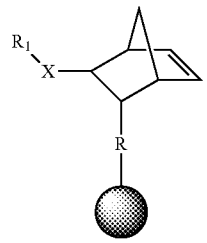

(i)

is selected as $Z_1$ and $Z_2$, R is absent, X is absent, and $R_1$ is H, and

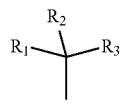

(ii)

is selected as $Y_1$ and $Y_2$, and $R_2$ is $Z_1$ and $Z_2$, $R_1$ and $R_3$ are selected from C1-20 linear, branched, or cyclic alkyl group, C6-20 aryl group, F, Cl, Br, I, $CF_3$, $CCl_3$, or $OCH_3$.

2. A mechanochromic resin in which the mechanochromic luminescent material according to claim 1 is crosslinked to a polymer chain.

3. The mechanochromic resin according to claim 2, wherein the mechanochromic resin is in the form of a film or a fiber.

4. A tension sensor comprising the mechanochromic resin according to claim 3.

5. A method for producing a mechanochromic luminescent material represented by formula (26) below, comprising a step of reacting a compound represented by formula (16) below and a compound represented by formula (25) below:

in the formula, $Y_1$ and $Y_2$ represent substituents that inhibit aggregation of a mechanochromic luminescent material represented by formula (26), and may be the same or different, $Z_1$ and $Z_2$ represent polymerizable groups, and may be the same or different, n represents an integer of 0-3,

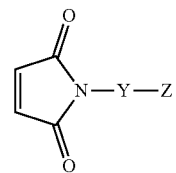

(16)

in the formula, Y is the same as $Y_1$ or $Y_2$; and Z is the same as $Z_1$ or $Z_2$,

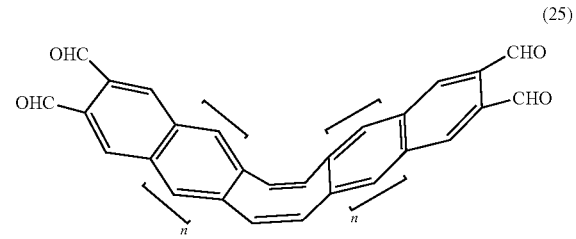

(25)

in the formula, n represents an integer of 0-3, wherein $Y_1$ and $Y_2$ are selected from the following substituents: represented by Chemical formula 3

[Chemical formula 3]

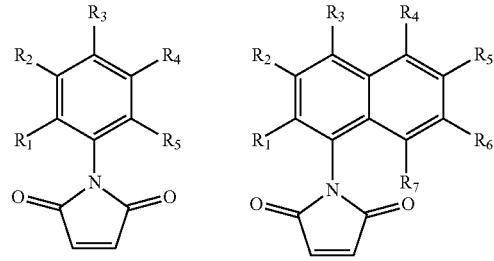

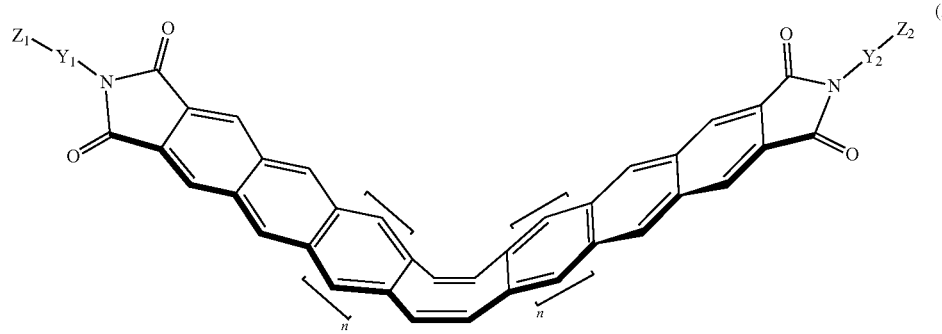

(26)

-continued

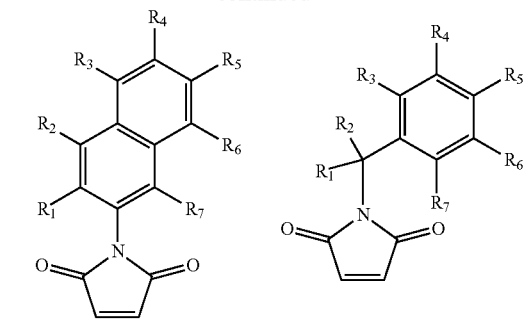
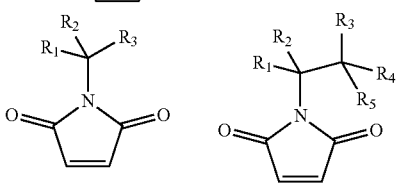
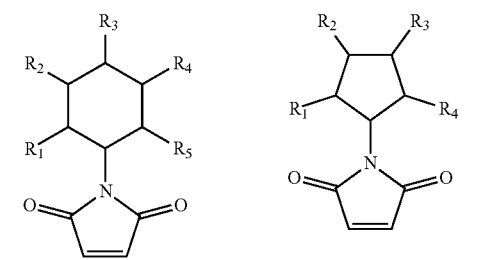
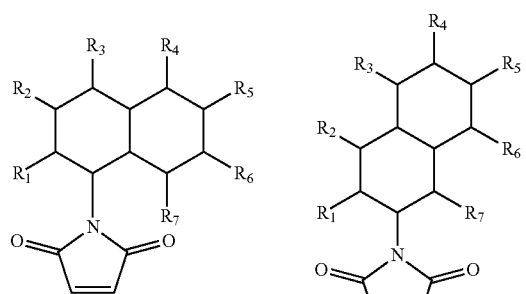
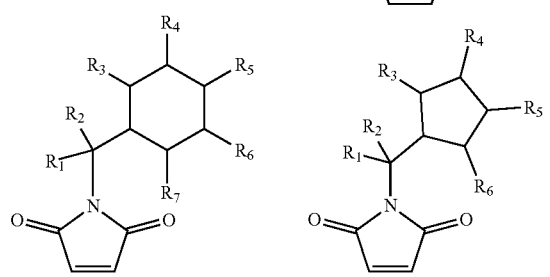
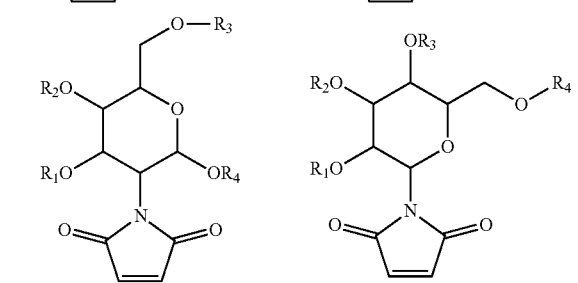

-continued

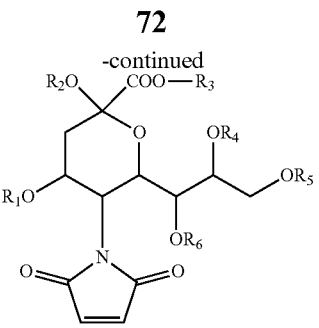

any one of the substituents $R_1$-$R_7$ represents a polymerizable group $Z_1$ or $Z_2$; $R_1$-$R_7$ other than the polymerizable group $Z_1$ or $Z_2$ represent H, a C1-20 linear, branched, or cyclic alkyl group, C6-20 aryl group, F, Cl, Br, I, $CF_3$, $CCl_3$, or $OCH_3$; and $R_1$-$R_7$ other than the polymerizable group $Z_1$ or $Z_2$ may be the same or different, wherein the polymerizable groups $Z_1$ and $Z_2$ are selected from the following substituents:

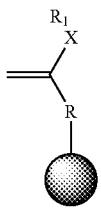

(3)

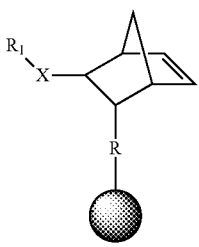

(4)

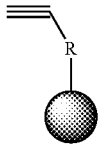

(5)

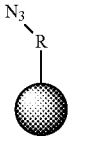

(6)

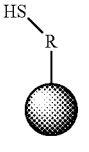

(7)

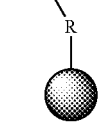

(8)

-continued (9)
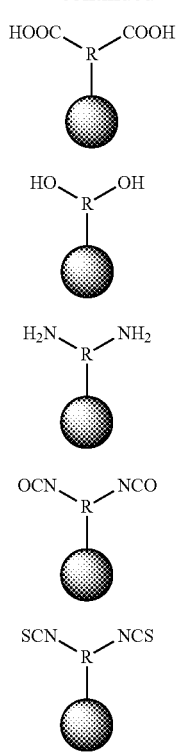
(10)
(11)
(12)
(13)

in the above formulas (3) and (4), X represents an amide or ester, but may be absent; in the above formulas (3) and (4), $R_1$ is the same as $R_1$ in [Chemical formula 3]; in the above formulas (3) to (13), R represents a C1-20 linear, branched, or cyclic alkylene group or a C6-20 arylene group, but R may be absent; and ● represents $Y_1$ or $Y_2$, and
wherein when:

(i)
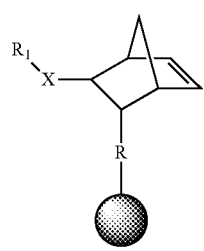

is selected as $Z_1$ and $Z_2$, R is absent, X is absent, and $R_1$ is H, and (ii)

is selected as $Y_1$ and $Y_2$, and $R_2$ is $Z_1$ and $Z_2$,
$R_1$ and $R_3$ are selected from C1-20 linear, branched, or cyclic alkyl group, C6-20 aryl group, F, Cl, Br, I, $CF_3$, $CCl_3$, or $OCH_3$.

6. The method for producing a mechanochromic luminescent material according to claim 5, wherein n is 0 or 1.

7. A method for producing a mechanochromic resin comprising
a step of mixing a mechanochromic luminescent material represented by formula (26) below, a polymerizable monomer, and a catalyst or initiator in an organic solvent,

(26)
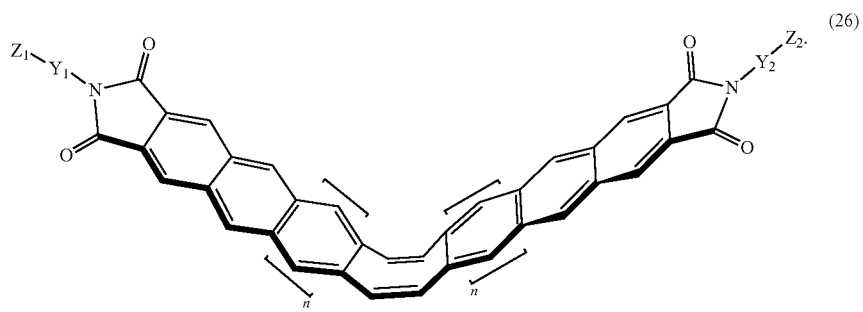

in the formula, $Y_1$ and $Y_2$ represent substituents that inhibit aggregation of a mechanochromic luminescent material represented by formula (26), and may be the same or different, $Z_1$ and $Z_2$ represent polymerizable groups, and may be the same or different, n represents an integer of 0-3,
wherein $Y_1$ and $Y_2$ are selected from the following substituents: represented by Chemical formula 3

[Chemical formula 3]

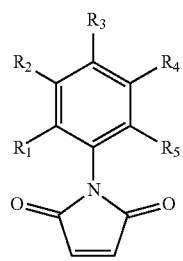 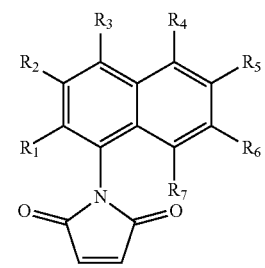

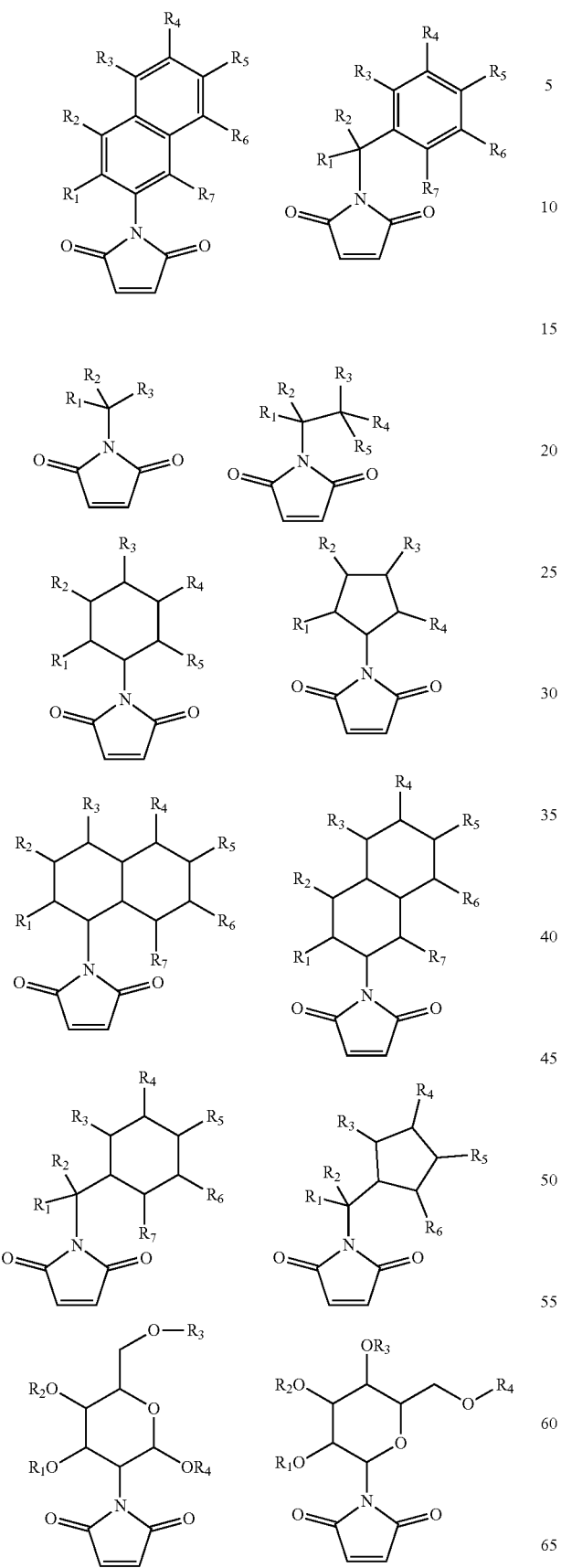
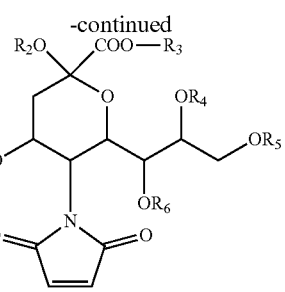

any one of the substituents $R_1$-$R_7$ represents a polymerizable group $Z_1$ or $Z_2$; $R_1$-$R_7$ other than the polymerizable group $Z_1$ or $Z_2$ represent H, a C1-20 linear, branched, or cyclic alkyl group, C6-20 aryl group, F, Cl, Br, I, $CF_3$, $CCl_3$, or $OCH_3$; and $R_1$-$R_7$ other than the polymerizable group $Z_1$ or $Z_2$ may be the same or different, wherein the polymerizable groups $Z_1$ and $Z_2$ are selected from the following substituents:

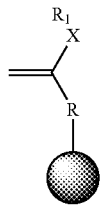

(3)

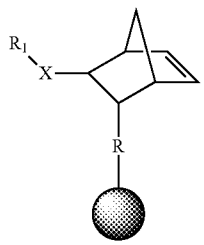

(4)

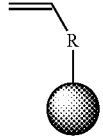

(5)

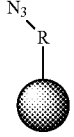

(6)

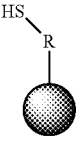

(7)

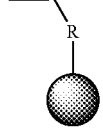

(8)

-continued

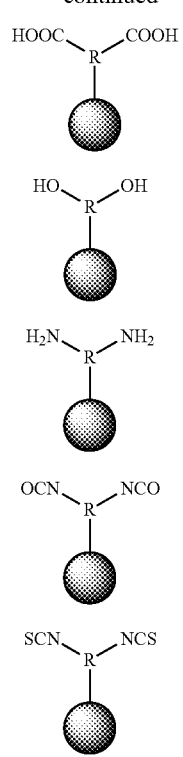

(9)
(10)
(11)
(12)
(13)

in the above formulas (3) and (4), X represents an amide or ester, but may be absent; in the above formulas (3) and (4), $R_1$ is the same as $R_1$ in [Chemical formula 3]; in the above formulas (3) to (13), R represents a C1-20 linear, branched, or cyclic alkylene group or a C6-20 arylene group, but R may be absent; and ● represents $Y_1$ or $Y_2$, and wherein when:

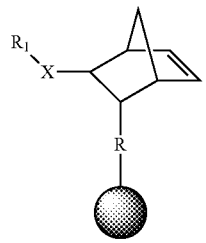

(i)

is selected as $Z_1$ and $Z_2$, R is absent, X is absent, and $R_1$ is H, and

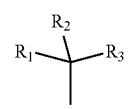

(ii)

is selected as $Y_1$ and $Y_2$, and $R_2$ is $Z_1$ and $Z_2$, $R_1$ and $R_3$ are selected from C1-20 linear, branched, or cyclic alkyl group, C6-20 aryl group, F, Cl, Br, I, $CF_3$, $CCl_3$, or $OCH_3$.

8. The method for producing a mechanochromic resin according to claim 7, wherein n is 0 or 1.

* * * * *

UNITED STATES PATENT AND TRADEMARK OFFICE
CERTIFICATE OF CORRECTION

PATENT NO.          : 10,442,886 B2
APPLICATION NO.     : 15/527639
DATED               : October 15, 2019
INVENTOR(S)         : Hiroshi Yabu et al.

Page 1 of 1

It is certified that error appears in the above-identified patent and that said Letters Patent is hereby corrected as shown below:

On the Title Page

Item (54), "MECHANOCHROMIC LUMINESCENT MATERIAL, MECHANOCHROMIC RESIN OBTAINED BY CROSSLINKING MECHANOCHROMIC LUMINESCENT MATERIAL, METHOD FOR PRODUCING MECHANOCHROMIC LUMINESCENT MATERIAL, AND METHOD FOR PRODUCING MECHANOCHROMIC" should read -- "MECHANOCHROMIC LUMINESCENT MATERIAL, MECHANOCHROMIC RESIN OBTAINED BY CROSSLINKING MECHANOCHROMIC LUMINESCENT MATERIAL, METHOD FOR PRODUCING MECHANOCHROMIC LUMINESCENT MATERIAL, AND METHOD FOR PRODUCING MECHANOCHROMIC RESIN --

Signed and Sealed this
Twenty-sixth Day of November, 2019

Andrei Iancu
*Director of the United States Patent and Trademark Office*